US012600740B2

(12) United States Patent
Yong et al.

(10) Patent No.: US 12,600,740 B2
(45) Date of Patent: Apr. 14, 2026

(54) FLUORINATED N-ACETYL GLUCOSAMINE ANALOGS AND XYLOSE DERIVATIVES

(71) Applicant: UTI Limited Partnership, Calgary (CA)

(72) Inventors: Voon Wee Yong, Calgary (CA); Chang-Chun Ling, Calgary (CA); Erin Laurel Stephenson, Calgary (CA); Ping Zhang, Calgary (CA); Michael Bradley Keough, Edmonton (CA); Khalil Sherali Rawji, Cambridge (GB)

(73) Assignee: UTI Limited Partnership, Calgary (CA)

( * ) Notice: Subject to any disclaimer, the term of this patent is extended or adjusted under 35 U.S.C. 154(b) by 808 days.

(21) Appl. No.: 17/843,818

(22) Filed: Jun. 17, 2022

(65) Prior Publication Data

US 2022/0332746 A1 Oct. 20, 2022

Related U.S. Application Data

(63) Continuation-in-part of application No. 17/059,318, filed as application No. PCT/CA2019/050754 on May 31, 2019, now Pat. No. 11,365,212.

(60) Provisional application No. 62/678,580, filed on May 31, 2018.

(51) Int. Cl.
*C07H 5/06* (2006.01)
*A61P 25/00* (2006.01)

(52) U.S. Cl.
CPC ................ *C07H 5/06* (2013.01); *A61P 25/00* (2018.01)

(58) Field of Classification Search
CPC ........ C07H 13/04; C07H 15/04; C07H 15/08; A61K 31/7024
See application file for complete search history.

(56) References Cited

U.S. PATENT DOCUMENTS

2003/0148997 A1 8/2003 Sackstein et al.

FOREIGN PATENT DOCUMENTS

| | | | |
|---|---|---|---|
| EP | 0527042 | A3 | 1/1994 |
| JP | 2009029770 | A | 2/2009 |
| WO | WO-199532955 | A1 | 12/1995 |
| WO | WO-2016200759 | A1 | 12/2016 |
| WO | WO-2019/227228 | A1 | 12/2019 |

OTHER PUBLICATIONS

Albler, et al., "From Amino Acids to Fluorine-Containing Carbohydrates: De Novo Synthesis of 2-Amino-4-Fluoroxylose and -lyxose," European Journal of Organic Chemistry, Jan. 2015, pp. 1314-1319 (6 pages).

Albler, et al., "Synthetic Routes towards Fluorine-Containing Amino Sugars: Synthesis of Fluorinated Analogues of Tomosamine and 4-Amino-4-deoxyarabinose," European Journal of Organic Chemistry, Jan. 2014, pp. 2451-2459 (9 pages).

Aspinall, et al., "The hex-5-enose degradation: zinc dust cleavage of 6-deoxy-6-iodo-α-D-galactopyranosidic linkages in methylated di- and trisaccharides," Department of Chemistry, Apr. 1984, pp. 2728-2735 (8 pages).

Beddows et al., "Pathogenic Hypothalamic Extracellular Matrix Promotes Metabolic Disease," Nature, Sep. 2024, vol. 633(8031), pp. 914-922 (35 pages).

Bowering, et al., "Synthesis and Characterization of 2-O-(β-D-Glucopyranosyluronic Acid)-D-xylopyranose," Journal of the American Chemical Society, Jun. 1960, vol. 82, pp. 2827-2830 (4 pages).

Chizhov, et al., "Mass-spectrometric Characterization of 3,6-anhydrogalactose Derivatives," Carbohydrate Research, 1971, vol. 16, pp. 29-38 (10 pages).

Clingman, et al., "Red-seaweed Polysaccharides. Part I. Gracilaria confervoides," Jan. 1957, National Chemical Research Laborat, pp. 197-203 (7 pages).

Collins, et al., The Photochemistry of Carbohydrate Derivatives. Part 7. The Synthesis of Methyl 3,4-Di-O-(β-D-glucopyranosyl)-α-L-rhamnopyranoside from Photolabile Methyl 2,3-O-(2-Nitrobenzylidene)-α-L-rhamnopyranoside, Journal of the Chemical Society, Jan. 1983, pp. 1879-1884 (6 pages).

Ghorbani et al., "Versican Promotes T helper 17 Cytotoxic inflammation and Impedes Oligodendrocyte Precursor Cell Remyelination," Nature Communication, May 2022, vol. 13(1), pp. 1-8 (18 pages).

Gray, et al., "Bottom-Up Elucidation of Glycosidic Bond Stereochemistry," Analytical Chemistry, Mar. 2017, vol. 89, pp. 4540-4549 (10 pages).

Hall, et al., "The Epoxide-Episulphide Transformation," University of Calgary, Jan. 1961, pp. 1537-1545 (9 pages).

Hartlieb, et al., "Chemoenzymatic Synthesis of CMP-N-acetyl-7-fluoro-7-deoxy-neuraminic Acid," Carbohydrate Research, Feb. 2008, pp. 2075-2082 (8 pages).

Hough, et al., "Synthesis of fluoro Derivatives of 2-amino-2-deoxy-D-galactose and-D-glucose," Can. J. Chem., National Research Council of Canada, Jan. 1981, pp. 396-405 (10 pages).

Kajihara, et al., "Novel Features of Acceptor Recognition by B-(1→4)-galactosyltransferase," Carbohydrate Research, Jan. 1998, vol. 306, pp. 361-378 (18 pages).

Kovacik, et al., "Structural Analysis by Mass Spectrometry of Oligosaccharides Related to Xylans," Carbohydrate Research, Jan. 1981, vol. 88, pp. 189-201 (13 pages).

Mendonca, et al., "Synthesis of Sterically Crowded Derivatives of Anomeric Pairs of D-glucose Disaccharides," Carbohydrate Research, Jul. 2005, vol. 340, pp. 2055-2059 (5 pages).

Sorg, et al., "Synthesis and NMR Characterization of Hydroxyurea and Mesylglycol Glycoconjugates as Drug Candidates for Targeted Cancer Chemotherapy," Carbohydrate Research, Jan. 2005, vol. 340, pp. 181-189 (9 pages).

Non-Final Office Action for U.S. Appl. No. 17/059,318, dated Sep. 15, 2021 (12 pages).

(Continued)

*Primary Examiner* — Jonathan S Lau
(74) *Attorney, Agent, or Firm* — Clark & Elbing LLP

(57) ABSTRACT

The present disclosure relates generally to fluorinated glucosamine analogs and uses thereof, including analogs of N-acetyl glucosamine fluorinated at 4- and/or 6-position(s) and derivatives of xylose at anomeric position for the treatment of a neurological disease, such as multiple sclerosis; inflammation; cancer; central nervous system injury; or conditions associated with up-regulation of an extracellular matrix, such as chondroitin sulfate proteoglycans.

19 Claims, 29 Drawing Sheets

(56) References Cited

OTHER PUBLICATIONS

Notice of Allowance for U.S. Appl. No. 17/059,318, dated Feb. 9, 2022 (10 pages).
Zheng, et al., "Complete Relative Stereochemistry of Maitotoxin," Journal of the American Chemical Society, Apr. 1996, vol. 118, pp. 7946-7968 (23 pages).
Stephenson et al., "Targeting the Chondroitin Sulfate Proteoglycans: Evaluating Fluorinated Glucosamines and Xylosides in Screens Pertinent to Multiple Sclerosis," ACS Cent Sci. 5(7):1223-1234 (Jul. 24, 2019).
Hornik et al., "Synthesis and in vitro cytotoxicity of acetylated 3-fluoro, 4-fluoro and 3,4-difluoro analogs of D-glucosamine and D-galactosamine," Beilstein J Org Chem. 12:750-9 (2016).
Sharma et al, "Fluorinated carbohydrates as potential plasma membrane modifiers. Synthesis of 4- and 6-fluoro derivatives of 2-acetamido-2-deoxy-D-hexopyranoses," Carbohydr Res. 198(2):205-21 (1990).
Berkin et al., "Synthesis of 4-deoxy-4-fluoro analogues of 2-acetamido-2-deoxy-d-glucose and 2-acetamido-2-deoxy-d-galactose and their effects on cellular glycosaminoglycan biosynthesis"; Carbohydr Res. 326(4):250-63 (2000).
Millqvist-Fureby et al., "Regioselective synthesis of ethoxylated glycoside esters using beta-glucosidase m supersaturated solutions and lipases in organic solvents," Biotechnol Bioeng. 59(6):747-53 (1998).
De Bruyne et al., "Synthesis of beta-D-xylopyranosides of substituted and branched-chain aliphatic alcohols," Carbohydr Res. 5(1):95-97 (1967).
Sharkov et al., "Glycosides of alditols and glycols as glycerol substitutes," Sb. Tr., Gos. Nauchn.-Issled Inst. Gidrolizn. i Sul'fitno-Spirt. Prom. 9:138-152 (1961) (16 pages).
International Search Report and Written Opinion for International Application No. PCT/CA2019/050754, mailed Aug. 2, 2019 (16 pages).
"Medications," National Multiple Sclerosis Society, <www.nationalmssociety.org/Treating-MS/Medications>, retrieved Sep. 10, 2021 (6 pages).
"What are neurological disorders?" World Health Organization, <https://www.who.int>, dated May 3, 2016, retrieved Dec. 15, 2020 (2 pages).
International Preliminary Report on Patentability for International Application No. PCT/CA2019/050754, issued Dec. 1, 2020 (10 pages).
Asher et al., "Neurocan Is Upregulated in Injured Brain and in Cytokine-treated Astrocytes," J Neurosci. 20(7):2427-2438 (2000).
Baecher-Allan et al., "Multiple Sclerosis: Mechanisms and Immunotherapy," Neuron. 97(4):742-768 (Feb. 21, 2018).
Barthel et al., "Peracetylated 4-fluoro-glucosamine reduces the content and repertoire of N- and O-glycans without direct incorporation," J Biol Chem. 286(24):21717-21731 (2017).
Bellavance et al., "Patrolling monocytes play a critical role in CX3CR1-mediated neuroprotection during excitotoxicity," Brain Struct Funct. 220(3):1759-1776 (2015).
Bernacki et al., "Biochemical characteristics, metabolism, and antitumor activity of several acetylated hexosamines," J Supramol Struct. 7(2):235-250 (1977).
Burnside et al., "Manipulating the extracellular matrix and its role in brain and spinal cord plasticity and repair," Neuropathol Appl Neurobiol. 40(1):26-59 (2014).
Carulli et al., "Composition of Perineuronal Nets in the Adult Rat Cerebellum and the Cellular Origin of Their Components," J Comp Neurol. 494(4):559-577 (2006).
Chang et al., "Cortical Remyelination: A New Target for Repair Therapies in Multiple Sclerosis," Ann Neurol. 72(6):918-926 (2012).
Cua et al., "Overcoming Neurite-Inhibitory Chondroitin Sulfate Proteoglycans in the Astrocyte Matrix," Glia. 61(6):972-984 (2013).
Dyck et al., "Chondroitin sulfate proteoglycans: Key modulators in the developing and pathologic central nervous system," Exp Neurol. 269:169-187 (2015).
Dyck et al., "Perturbing chondroitin sulfate proteoglycan signaling through LAR and PTP(sigma) receptors promotes a beneficial inflammatory response following spinal cord injury," J Neuroinflammation. 15(1):90 (Mar. 20, 2018) (26 pages).
Glant et al., "Critical Roles of Glycosaminoglycan Side Chains of Cartilage Proteoglycan (Aggrecan) in Antigen Recognition and Presentation," J Immunol. 160(8):3812-3819 (1998) (9 pages).
Grigorian et al., "N-Acetylglucosamine Inhibits T-helper 1 (Th1)/T-helper 17 (Th17) Cell Responses and Treats Experimental Autoimmune Encephalomyelitis," J Biol Chem. 286(46):40133-40141 (2011).
Haas et al., "Entorhinal Cortex Lesion in Adult Rats Induces the Expression of the Neuronal Chondroitin Sulfate Proteoglycan Neurocan in Reactive Astrocytes," J Neurosci. 19(22):9953-9963 (1999).
Hara et al., "Interaction of reactive astrocytes with type I collagen induces astrocytic scar formation through the integrin-N-cadherin pathway after spinal cord injury," Nat Med. 23(7):818-828 (2017) (13 pages).
Haylock-Jacobs et al., "Chondroitin sulphate proteoglycans: Extracellular matrix proteins that regulate immunity of the central nervous system," Autoimmun Rev. 10(12):766-772 (2011) (8 pages).
Holmqvist et al., "Synthesis and biology of oligoethylene glycol linked naphthoxylosides," Bioorg Med Chem. 21(11):3310-3317 (2013).
Horssen et al., "Basement Membrane Proteins in Multiple Sclerosis-Associated Inflammatory Cuffs: Potential Role in Influx and Transport of Leukocytes," J Neuropathol Exp Neurol. 64(8):722-729 (2005).
Horssen et al., "Extensive extracellular matrix depositions in active multiple sclerosis lesions," Neurobiol Dis. 24(3):484-49 (2006).
Jones et al., "The chondroitin sulfate proteoglycans neurocan, brevican, phosphacan, and versican are differentially regulated following spinal cord injury," Exp Neurol. 182(2):399-411 (2003).
Karimi-Abdolrezaee et al., "Synergistic effects of transplanted adult neural stem/progenitor cells, chondroitinase, and growth factors promote functional repair and plasticity of the chronically injured spinal cord," J Neurosci. 30(5):1657-1676 (2010).
Keough et al., "An inhibitor of chondroitin sulfate proteoglycan synthesis promotes central nervous system remyelination," Nat Commun. 7:11312 (2016) (12 pages).
Lau et al., "Chondroitin Sulfate Proteoglycans in Demyelinated Lesions Impair Remyelination," Ann Neurol. 72(3):419-432 (2012).
Marathe et al., "Fluorinated per-acetylated GalNAc metabolically alters glycan structures on leukocyte PSGL-1 and reduces cell binding to selectins," Blood. 115(6):1303-1312 (2010).
Mayo et al., "Regulation of astrocyte activation by glycolipids drives chronic CNS inflammation," Nat Med. 20(10):1147-56 (2014) (13 pages).
McKeon et al., "The Chondroitin Sulfate Proteoglycans Neurocan and Phosphacan Are Expressed by Reactive Astrocytes in the Chronic CNS Glial Scar," J Neurosci. 19(24):10778-88 (1999).
O'Meara et al., "Derivation of Enriched Oligodendrocyte Cultures and Oligodendrocyte/Neuron Myelinating Co-cultures From Post-natal Murine Tissues," J Vis Exp. (54):e3324 (2011) (9 pages).
Medina-Rodriguez et al., "Protocol to Isolate a Large Amount of Functional Oligodendrocyte Precursor Cells from the Cerebral Cortex of Adult Mice and Humans," PLoS One. 8(11):e81620 (2013) (13 pages).
Mishra et al., "Myeloid cells—targets of medication in multiple sclerosis," Nat Rev Neurol. 12(9):539-51 (2016) (13 pages).
Nigro et al., "Regulation of Heparan Sulfate and Chondroitin Sulfate Glycosaminoglycan Biosynthesis by 4-Fluoro-glucosamine in Murine Airway Smooth Muscle Cells," J Biol Chem. 284(25):16832-16839 (2009).
Poole et al., "Chondrons From Articular Cartilage. (IV) Immunolocalization of Proteoglycan Epitopes in Isolated Canine Tibial Chondrons," J Histochem Cytochem. 39(9):1175-87 (1991).
Prydz et al., "Synthesis and sorting of proteoglycans," J Cell Sci. 113(Pt 2):193-205 (2000).
Pu et al., "The extracellular matrix: Focus on oligodendrocyte biology and targeting CSPGs for remyelination therapies," Glia. 66(9):1809-1825 (Sep. 2018).

(56) References Cited

OTHER PUBLICATIONS

Ransohoff et al., "The anatomical and cellular basis of immune surveillance in the central nervous system," Nat Rev Immunol. 12(9):623-35 (2012).
Reich et al., "Multiple Sclerosis," N Engl J Med. 378(2):169-180 (Jan. 11, 2018).
Rivera-Sagredo et al., "4-O-beta-D-Galactopyranosyl-D-xylose: A new synthesis and application to the evaluation of intestinal lactase," Carbohydr Res. 228(1):129-35 (1992).
Sharma et al., "General methods for modification of sialic acid at C-9. Synthesis of N-acetyl-9-deoxy-9-fluoroneuraminic acid," Carbohydr Res. 175(1):25-34 (1988).
Silver et al., "Regeneration beyond the glial scar," Nat Rev Neurosci. 5(2):146-56 (2004).
Sobel et al., "White Matter Extracellular Matrix Chondroitin Sulfate/Dermatan Sulfate Proteoglycans in Multiple Sclerosis," J Neuropathol Exp Neurol. 60(12):1198-207 (2001).
Sorokin, "The impact of the extracellular matrix on inflammation," Nat Rev Immunol. 10(10):712-23 (2010).
Stephenson et al., "Chondroitin sulfate proteoglycans as novel drivers of leucocyte infiltration in multiple sclerosis," Brain. 141(4):1094-1110 (Apr. 1, 2018).
Tang et al., "Changes in Distribution, Cell Associations, and Protein Expression Levels of NG2, Neurocan, Phosphacan, Brevican, Versican V2, and Tenascin-C During Acute to Chronic Maturation of Spinal Cord Scar Tissue," J Neurosci Res. 71(3):427-44 (2003).
Tsuzuki et al., "4-Deoxy-4-fluoro-xyloside derivatives as inhibitors of glycosaminoglycan biosynthesis," Bioorg Med Chem Lett. 20(24):7269-73 (2010).
Vecil et al., "Interleukin-1 Is a Key Regulator of Matrix Metalloproteinase-9 Expression in Human Neurons in Culture and Following Mouse Brain Trauma In Vivo," J Neurosci Res. 61(2):212-24 (2000).
Weaver et al., "An elevated matrix metalloproteinase (MMP) in an animal model of multiple sclerosis is protective by affecting Th1/Th2 polarization," FASEB J. 19(12):1668-70 (2005) (21 pages).
Van Wijk et al., "A common sugar-nucleotide-mediated mechanism of inhibition of (glycosamino)glycan biosynthesis, as evidenced by 6F-GalNAc ($Ac_3$)," FASEB J. 29(7):2993-3002 (2015).
Wu et al., "Endothelial basement membrane laminin alpha5 selectively inhibits T lymphocyte extravasation into the brain," Nat Med. 15(5):519-27 (2009).
Zhou et al., "Immune modulation by chondroitin sulfate and its degraded disaccharide product in the development of an experimental model of multiple sclerosis," J Neuroimmunol. 223(1-2):55-64 (2010).

a. N-Acetyl-D-glucosamine and derivatives

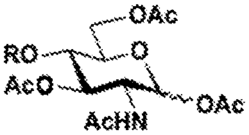

1 (R=Ac)
(Ac-GlcNAc)
2 (R=Me)
(Ac-4-Me-GlcNAc)

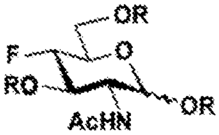

3 (R=Ac)
(Ac-4-F-GlcNAc)
4 (R=H)
(4-F-GlcNAc)

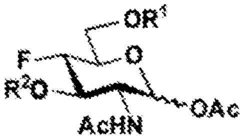

5 ($R^1$=$R^2$=Me)
(Me-4-F-GlcNAc)
6 ($R^1$=Ac, $R^2$=Me)
(MeAc-4-F-GlcNAc)

7 (R=$COCH_2CH_3$)
(Ac-4-F-GlcNAcOPr)
8 (R=$CO(CH_2)_2CH_3$)
(Ac-4-F-GlcNAcOBu)

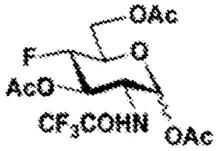

9
(Ac-4-F-GlcNTFA)

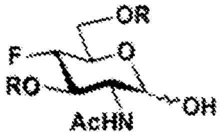

10 (R=Ac)
(Ac-4-F-GlcNAcOH)
11 (R=$COCH_2CH_3$)
(Pr-4-F-GlcNAcOH)
12 (R=$CO(CH_2)_2CH_3$)
(Bu-4-F-GlcNAcOH)

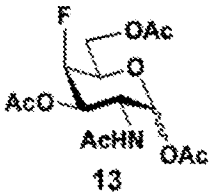

13
(Ac-4-F-GalNAc)

14 (R=H)
(Ac-4-Cl-GlcNAcOH)
15 (R=Ac)
(Ac-4-Cl-GlcNAc)

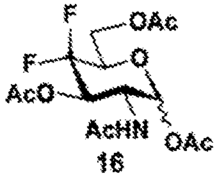

16
(Ac-4,4-diF-GlcNAc)

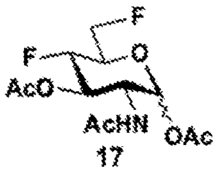

17
(Ac-4,6-diF-GlcNAc)

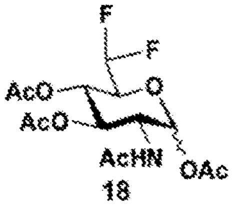

18
(Ac-6,6-diF-GlcNAc)

b. D-Xylose derivatives

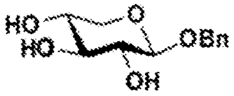

19
(bXyl-OBn)

20 (R=$CH_2CH_2OH$)
(Ac-bXyl-MEG)
21 (R=$(CH_2CH_2O)_4H$)
(Ac-bXyl-TEG)

22 (R=$(CH_2)_2SO_3^-Na^+$)
(Ac-bXyl-C2S)
23 (R=$(CH_2)_6SO_3^-Na^+$)
(Ac-bXyl-C6S)

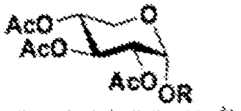

24 (R=$(CH_2)_6SO_3^-Na^+$)
(Ac-aXyl-C6S)

25 (R=$(CH_2)_2NMe_2$)
(Ac-bXyl-C2N)

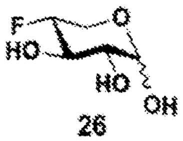

26
(4-F-Xyl)

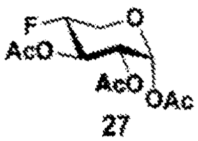

27
(Ac-4-F-aXyl)

28
(Ac-4-F-bXyl)

$R_4$, $R_4$'=F
$R_4$=F, $R_4$'=H (GlcNAc)
$R_4$=H, $R_4$'=F (GalNAc)

$R_1$=Ac
$R_1$=H
$R_1$=$CoCH_2CH_3$

MAB2030 (chondroitin sulfate GAG stubs)

2H6 (4-sulfated chondroitin sulfate GAGs)

MAB2030 (chondroitin sulfate GAG stubs)

2H6 (4-sulfated chondroitin sulfate GAGs)

10E4 (heparan sulfate side chain)

Toxicity of 100µM compounds on astrocytes

Toxicity of 100µM compounds on neurons

Top two compound structures

Cuffs per mouse spinal cord

DC45+ cells within 100μm of cuffs

Flow cytometry from the blood

Distribution of CD45+ cells around perivascular cuffs

Gating strategy for blood

Gating strategy for spinal cord

MAB2030 (chondroitin sulfate GAG stubs)

2H6 (4-sulfated chondroitin sulfate GAGs)

CS56 (4-, 6-sulfated chondroitin GAGs)

10E4(heparan sulfate side chain)

MAB2030 cell extract

Flow cytometry from the blood

Distribution of DC45+ cells around perivascular cuffs

FLUORINATED N-ACETYL GLUCOSAMINE ANALOGS AND XYLOSE DERIVATIVES

FIELD

The present disclosure relates generally to fluorinated glucosamine analogs and uses thereof.

INTRODUCTION

Multiple sclerosis (MS) is an inflammatory disorder of the central nervous system (CNS) accompanied by loss of neurons and oligodendrocytes and prominent demyelination. While several immunomodulators have altered the natural history of relapsing-remitting MS, treatment response in many patients remains inadequate; moreover, there are no current therapies to halt the progression of neurological disabilities of MS. There is a need to develop therapies that not only target the aberrant immune responses, but also to promote repopulation of oligodendrocytes and remyelination in demyelinated plaques.

As in other tissues, the CNS has an extracellular matrix (ECM) that normally serves important physiologic functions; when dysregulated in injury, however, the brain ECM components can directly influence inflammation and repair [Sorokin, L. The impact of the extracellular matrix on inflammation. Nature reviews. Immunology 10, 712-723 (2010); Haylock-Jacobs, S., Keough, M. B., Lau, L. & Yong, V. W. Chondroitin sulphate proteoglycans: extracellular matrix proteins that regulate immunity of the central nervous system. Autoimmunity reviews 10, 766-772 (2011); Pu, A., Stephenson, E. L. & Yong, V. W. The extracellular matrix: Focus on oligodendrocyte biology and targeting CSPGs for remyelination therapies. Glia (2018); Rolls, A. et al. Two faces of chondroitin sulfate proteoglycan in spinal cord repair: a role in microglia/macrophage activation. PLoS medicine 5(2008)]. For example, the presence of type I collagen can direct astrocyte fate from reactive to gliotic [Hara, M. et al. Interaction of reactive astrocytes with type I collagen induces astrocytic scar formation through the integrin-N-cadherin pathway after spinal cord injury. *Nature Medicine* 23, 818-828 (2017)] and the laminin composition of the basement membrane dictates where T lymphocytes infiltrate into the CNS [Wu, C. et al. Endothelial basement membrane laminin alpha5 selectively inhibits T lymphocyte extravasation into the brain. Nature medicine 15, 519-527 (2009)].

An emerging driver of inflammation in the brain is the chondroitin sulfate proteoglycans (CSPGs) [Haylock-Jacobs, S., Keough, M. B., Lau, L. & Yong, V. W. Chondroitin sulphate proteoglycans: extracellular matrix proteins that regulate immunity of the central nervous system. [Autoimmunity reviews 10, 766-772 (2011)]. CSPGs are upregulated in demyelinated plaques in brain specimens in MS [Sobel, R. A. & Ahmed, A. S. White matter extracellular matrix chondroitin sulfate/dermatan sulfate proteoglycans in multiple sclerosis. Journal of neuropathology and experimental neurology 60, 1198-1207 (2001)] and in perivascular cuffs where immune cells infiltrate into the brain parenchyma [Stephenson, E. L. et al. Chondroitin sulfate proteoglycans as novel drivers of leucocyte infiltration in multiple sclerosis. Brain: a journal of neurology 141, 1094-1110 (2018)]. Their presence in MS lesions is associated with enhanced activation and transmigratory capacity of macrophages [Stephenson, E. L. et al. Chondroitin sulfate proteoglycans as novel drivers of leucocyte infiltration in multiple sclerosis. Brain: a journal of neurology 141, 1094-1110 (2018)] as well as impaired remyelination [Chang, A. et al. Cortical remyelination: a new target for repair therapies in multiple sclerosis. Annals of neurology 72, 918-926 (2012)]. In both traumatic CNS injuries and MS, CSPGs inhibit regeneration by interfering with the migration of pro-regenerative neural and oligodendrocyte precursor cells (OPCs) into lesions [Lau, L. W. et al. Chondroitin sulfate proteoglycans in demyelinated lesions impair remyelination. Annals of neurology 72, 419-432 (2012); Silver, J. & Miller, J. H. Regeneration beyond the glial scar. Nature Reviews Neuroscience 5, 146 (2004); Dyck, S. M. & Karimi-Abdolrezaee, S. Chondroitin sulfate proteoglycans: Key modulators in the developing and pathologic central nervous system. Exp Neurol 269, 169-87 (2015)].

Given the above observations, it is considered pertinent to overcome CSPGs in neurological disorders including MS. In focal traumatic spinal cord injury, the enzyme chondroitinase ABC has been injected directly into the lesion to remove the glycosaminoglycan (GAGs) chains of CSPGs, which are a crucial component of their inhibitory action [Burnside, E. R. & Bradbury, E. J. Manipulating the extracellular matrix and its role in brain and spinal cord plasticity and repair. Neuropathology and applied neurobiology 40, 26-59 (2014); Dyck, S. et al. Perturbing chondroitin sulfate proteoglycan signaling through LAR and PTPσ receptors promotes a beneficial inflammatory response following spinal cord injury. Journal of Neuroinflammation 15, 90 (2018); Karimi-Abdolrezaee, S., Eftekharpour, E., Wang, J., Schut, D. & Fehlings, M. G. Synergistic Effects of Transplanted Adult Neural Stem/Progenitor Cells, Chondroitinase, and Growth Factors Promote Functional Repair and Plasticity of the Chronically Injured Spinal Cord. The Journal of Neuroscience 30, 1657-1676 (2010)]. The local injection would not be feasible for a condition such as MS, with multi-focal lesions throughout the brain and spinal cord. Moreover, it was found that once anchored onto a substrate, CSPG inhibition of the morphological differentiation of OPCs cannot be overcome by promising pro-remyelinating therapies [Keough, M. B. et al. An inhibitor of chondroitin sulfate proteoglycan synthesis promotes central nervous system remyelination. Nature communications 7, 11312 (2016)]. Thus, preventing deposition of CSPGs by interfering with their biosynthesis would be an effective approach to overcoming the problem.

SUMMARY

In an aspect described herein, there is provided compound according to any one of formula (62)-(68) or a pharmaceutically acceptable salt thereof:

62

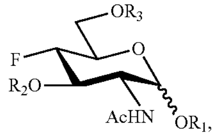

63

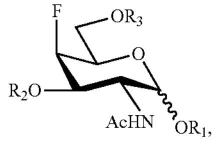

-continued

64

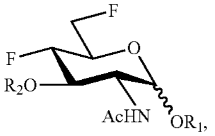

65

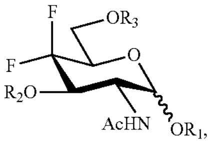

66

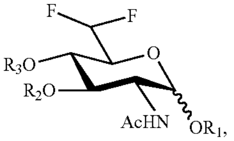

67

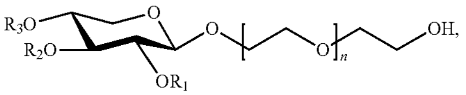

68

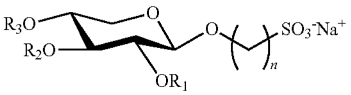

wherein: $R_1$, $R_2$ and $R_3$ are independently H or an acyl group, and at least one of $R_1$, $R_2$ and $R_3$ is an acyl group defined as R'CO— or R"XCO—, wherein: R' is a substituted or unsubstituted, branched or linear alkyl or heteroalkyl containing up to 20 carbons; R" is a substituted or unsubstituted, branched or linear alkyl or heteroalky containing up to 20 carbons; and X is a heteroatom selected from the group consisting of O, N, and S;

with the caveat that: when the compound is formula (62), R' cannot be $—CH_3$, $—CH_2CH_3$, or $—(CH_2)_2CH_3$; when the compound is formula (63), R' cannot be $—CH_3$, or $—CH_2CH_3$; and when the compound is formula (64) to (68), R' cannot be $—CH_3$.

In another aspect, the substituents of R' or R" can be selected from the group consisting of aryl, C1-C6 alkyl, and halogen; the heteroatoms of R' or R" are selected from the group consisting of O, N, and S; and/or R' or R" contain up to 12 carbons.

In still further aspects, R' or R" may be isopropyl or isobutyl.

In another aspect, the compound comprises formula (62) or a pharmaceutically acceptable salt thereof. Alternatively, the compound may comprise formula (65) or a pharmaceutically acceptable salt thereof.

In another aspect described herein, there is a pharmaceutical composition comprising a compound according to formula (62) to (68) and a pharmaceutically acceptable excipient.

According to another aspect described herein, these is provided a method of treating multiple sclerosis, a neurological disease or disorder associated with up-regulation of an extracellular matrix or chondroitin sulfate proteoglycans, an autoimmune disorder associated with up-regulation of an extracellular matrix such as chondroitin sulfate proteoglycans, or a tumour associated with up-regulation of an extracellular matrix such as chondroitin sulfate proteoglycans. The method comprising administering to a subject in need thereof an effective amount of a compound according to formula (62) to (68). For example, the method may be for treating multiple sclerosis in a subject having or suspected of having multiple sclerosis.

In an aspect described herein, there is provided a method for treating multiple sclerosis, a neurological disease or disorder associated with up-regulation of an extracellular matrix such as chondroitin sulfate proteoglycans, an autoimmune disorder associated with up-regulation of an extracellular matrix such as chondroitin sulfate proteoglycans, or a tumour associated with up-regulation of an extracellular matrix such as chondroitin sulfate proteoglycans. The method comprises administering to a subject in need thereof a therapeutically effective amount of a compound of formula (62) to (68), or a pharmaceutically acceptable salt thereof:

62

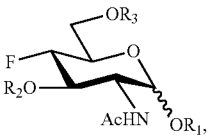

63

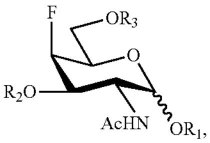

64

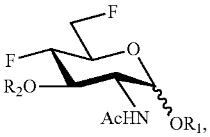

65

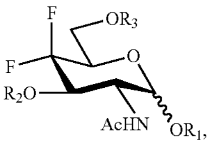

66

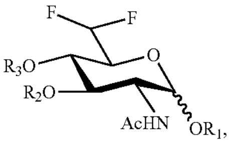

67

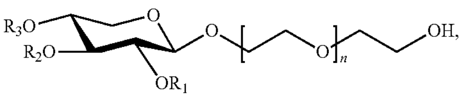

68

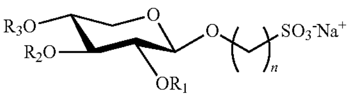

wherein: $R_1$, $R_2$ and $R_3$ are independently H or an acyl group, and at least one of $R_1$, $R_2$ and $R_3$ is an acyl group defined as R'CO— or R"XCO—, wherein: R' is a substituted or unsubstituted, branched or linear alkyl or heteroalkyl containing up to 20 carbons; R" is a substituted or unsubstituted, branched or linear alkyl or heteroalky containing up to 20 carbons; and X is a heteroatom selected from the group consisting of O, N, and S.

In a further aspect, substituents of R' or R" may be selected from the group consisting of aryl, C1-C6 alkyl, and halogen; the heteroatoms of R' or R" are selected from the group consisting of O, N, and S; and/or R' or R" contain up to 12 carbons.

In a further aspect, R' or R" may be isopropyl or isobutyl.

In yet a further aspect, the compound may comprise formula (62) or a pharmaceutically acceptable salt thereof; or the compound may comprise formula (65) or a pharmaceutically acceptable salt thereof.

Further aspects are described herein below.

In an aspect there is provided a compound of formula (62)

62

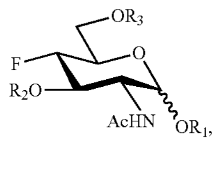

where any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an example, R2 and R3 are either an acetyl group or propanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (63)

63

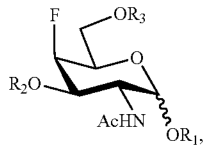

where any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an example R2 and R3 are either an acetyl group or propanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (64)

64

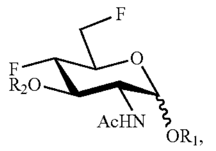

where any of the R1 and R2 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (65)

65

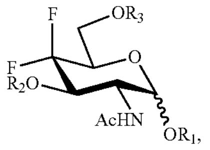

where any of the $R_1$, $R_2$ and $R_3$ groups of the formula can be a H or an acyl group, or a stereoisomer, a racemate, a tautomer, a pharmaceutically acceptable salt, a solvate, a prodrug, or a functional derivative thereof.

In an example R2 and R3 are either an acetyl group or propanoyl or butanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (66)

66

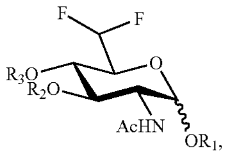

where any of the R1, R2 and R3 groups of the formula can be a H or an acyl group, a stereoisomer, a racemate, a tautomer, a pharmaceutically acceptable salt, a solvate, a prodrug, or a functional derivative thereof.

In an aspect there is provided a compound of formula (67)

67

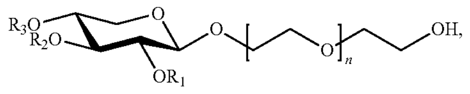

where n=0-20, any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (68)

68

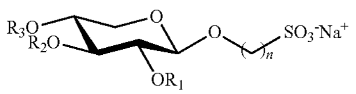

where n=2-12, and any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (7)

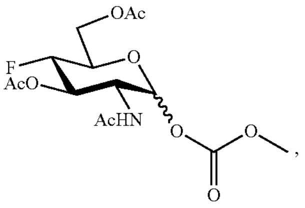

7 a compound of formula (8)

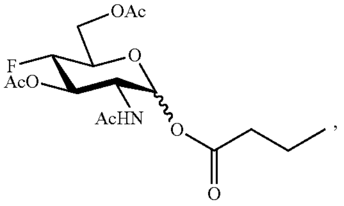

8 a compound of formula (10)

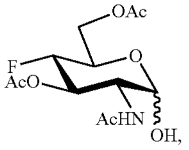

10 a compound of formula (11)

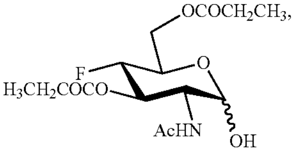

11 a compound of formula (17)

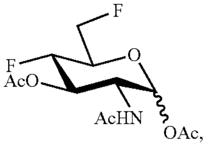

17 a compound of formula (18)

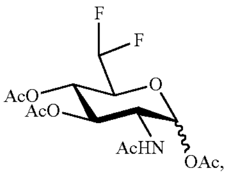

18 a compound of formula (21)

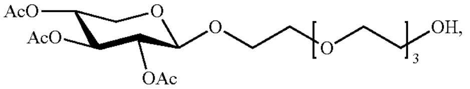

21 a compound of formula (23)

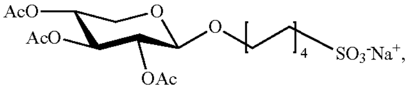

23 a compound of formula (16)

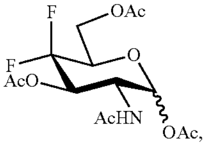

16 a compound of formula (13)

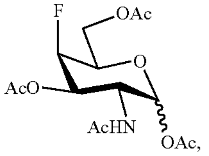

13 a stereoisomer, a racemate, a tautomer, a pharmaceutically acceptable salt, a solvate, a prodrug, or a functional derivative thereof.

In an aspect there is provided a pharmaceutical composition comprising a compound of described herein, or a stereoisomer, a racemate, a tautomer, a pharmaceutically acceptable salt, a solvate, a prodrug, or a functional derivative thereof, In an aspect there is provided a use of a compound as described herein, or a composition as described herein, for treating a subject, or suspected of having a neurological disease or disorder.

In an aspect there is provided a use of a compound as described herein, or a composition as described herein for treating a subject with, or suspected of having multiple sclerosis.

In an aspect there is provided a use of a compound as described herein, or a composition as described herein for treating a subject with, or suspected of having a disease or disorder associated with inflammation.

In an example the disease or disorder associated with inflammation is encephalomyelitis or autoimmune encephalomyelitis.

In an aspect there is provided a use of a compound as described herein, or a composition as described herein for treating a subject with, or suspected of having cancer.

In an aspect there is provided a use of a compound as described herein, or a composition as described herein for treating a subject with, or suspected of having a central nervous system injury.

In an example the subject is a human, a domesticated animal, livestock, a laboratory animal, a non-human mammal, a non-human primate, a rodent, a bird, a reptile, an amphibian, or a fish.

In an aspect there is provided a method for treating a neurological disease or disorder, comprising: administering a therapeutically effective amount of a compound as described herein, or a composition as described herein to a subject having, or suspected of having a neurological disease or disorder.

In an aspect there is provided a method for treating multiple sclerosis, comprising: administering a therapeutically effective amount of a compound as described herein, or a composition as described herein to a subject having, or suspected of having multiple sclerosis.

In an aspect there is provided a method for treating encephalomyelitis, comprising: administering a therapeutically effective amount of a compound as described herein, or a composition as described herein to a subject having, or suspected of having a disease or disorder associated with inflammation.

In an example said disease or disorder associated with inflammation is encephalomyelitis or autoimmune encephalomyelitis.

In an aspect there is provided a method for treating cancer, comprising: administering a therapeutically effective amount of a compound as described herein, or a composition as described herein to a subject having, or suspected of having cancer.

In an aspect there is provided a method for treating a central nervous system injury, comprising: administering a therapeutically effective amount of a compound as described herein, or a composition as described herein to a subject having, or suspected of having a central nervous system injury.

In an example the subject is a human, a domesticated animal, livestock, a laboratory animal, a non-human mammal, a non-human primate, a rodent, a bird, a reptile, an amphibian, or a fish.

In an aspect there is provided a use of a compound as described herein, or a composition as described herein in the manufacture of a medicament for treating a subject with, or suspected of having a neurological disease or disorder.

In an aspect there is provided a use of a compound as described herein, or a composition as described herein in the manufacture of a medicament for treating a subject with, or suspected of having multiple sclerosis.

In an aspect there is provided a use of a compound as described herein, or a composition as described herein in the manufacture of a medicament for treating a subject with, or suspected of having a disease or disorder associated with inflammation.

In an example the disease or disorder associated with inflammation is encephalomyelitis or an autoimmune encephalomyelitis.

In an aspect there is provided a use of a compound as described herein, or a composition as described herein in the manufacture of a medicament for treating a subject with, or suspected of having cancer.

In an aspect there is provided a use of a compound as described herein, or a composition as described herein in the manufacture of a medicament for treating a subject with, or suspected of having a central nervous system injury.

In an example the subject is a human, a domesticated animal, livestock, a laboratory animal, a non-human mammal, a non-human primate, a rodent, a bird, a reptile, an amphibian, or a fish.

In an aspect there is provided a method for treating a subject with, or suspected of having a neurological disease or disorder comprising: identifying a subject having or suspected of having a neurological disease or disorder, and administering a compound as described herein, or a composition as described herein.

In an aspect there is provided a method for treating a subject with, or suspected of having multiple sclerosis comprising: identifying a subject having or suspected of having multiple sclerosis, and administering a compound as described herein, or a composition as described herein.

In an aspect there is provided a method for treating a subject with, or suspected of having a disease or disorder associated with inflammation comprising: identifying a subject having or suspected of having a disease or disorder associated with inflammation, and administering a compound as described herein, or a composition as described herein.

In an example the disease or disorder associated with inflammation is encephalomyelitis or an autoimmune encephalomyelitis.

In an aspect there is provided a method for treating a subject with, or suspected of having cancer comprising: identifying a subject having or suspected of having cancer, and administering a compound as described herein, or a composition as described herein.

In an aspect there is provided a method for treating a subject with, or suspected of having a central nervous system injury comprising: identifying a subject having or suspected of having a central nervous system injury, and administering a compound as described herein, or a composition as described herein.

In an example the subject is a human, a domesticated animal, livestock, a laboratory animal, a non-human mammal, a non-human primate, a rodent, a bird, a reptile, an amphibian, or a fish.

In an aspect there is provide a kit comprising one or more compounds as described herein, or a pharmaceutical composition of a composition as described herein, and a container, and optionally instructions for the use thereof.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 2 depicts N-Acetyl-D-glucosamine and D-xylose derivatives highlighting their structure, short-form in parenthesis and compound number. a, Synthesized N-acetyl-D-glucosamine derivatives, and b, synthesized D-xyloside derivatives. Attachments to the oxygens in the skeleton were numbered based on to their attachment to the carbons in the skeleton of the monosaccharide (for example, the oxygen atom attached to C4 of xylose is referred to as 'O4').

FIG. 7 depicts that analog-treated astrocytes produce a matrix less inhibitory for OPC growth. a, Schematic of mixed glial cultures ('1'), and enrichment for oligodendrocyte precursor cells (OPCs) and astrocytes. Astrocytes were cultured and treated with glucosamines or xylosides ('2') and then removed, leaving behind a plate-bound matrix with inhibitory CSPGs. OPCs were seeded on these plates, and their outgrowth analyzed ('3'). b, OPCs cultured in the absence of astrocyte ECM and treated with control, CSPGs (10 μg/ml) and OPCs cultured on astrocyte-deposited ECM where astrocytes had been previously treated with DMSO, Ac-4-F-GlcNAc 3 or Ac-4,4-diF-GlcNAc 16. c, Quantification of mean process outgrowth of OPCs, showing the ability of some fluorinated analogs to improve OPC outgrowth compared to those grown on matrix from untreated astrocytes (control). Also shown are the mean outgrowth of OPCs grown in the absence of astrocyte-deposited ECM and treated with control ('No ECM'), bovine serum albumin ('No ECM+BSA') or 10 μg/ml CSPGs ('No ECM+CSPGs). Results are presented as four replicate wells of an individual experiment that was replicated at least twice. $^*P<0.05$, $^{}P<0.01$, $^{*}P<0.001$ one-way analysis of variance (ANOVA) with Dunnett's post hoc test compared treatments with untreated astrocytes (control). Error bars are mean±s.d. Note the 2-day time point was chosen to analyse the OPCs on the astrocyte matrix because previous studies [Lau, L. W.; Keough, M. B.; Haylock-Jacobs, S.; Cua, R.; Döring, A.; Sloka, S.; Stirling, D. P.; Rivest, S.; Yong, V. W. Chondroitin sulfate proteoglycans in demyelinated lesions impair remyelination. *Ann. Neurol.* 2012, 72 (3), 419-432; Keough, M. B.; Rogers, J. A.; Zhang, P.; Jensen, S. K.; Stephenson, E. L.; Chen, T.; Hurlbert, M. G.; Lau, L. W.; Rawji, K. S.; Plemel, J. R. et al. An inhibitor of chondroitin sulfate proteoglycan synthesis promotes central nervous system remyelination. *Nat. Commun.* 2016, 7, 11312] had determined that a CSPG matrix prominently inhibited process outgrowth of OPCs at 1 and 3 days. d, Combined chemical structure of the five N-acetyl-D-glucosamine derivatives that most effectively reduced CSPG production (Ac-4,4-diF-GlcNAc 16, Ac-4-F-GlcNAc 3, Ac-4-F-GlcNAcOH 10, Ac-4-F-GlcNAcOPr 7, Ac-4-F-GalNAc 13).

Figure 1:
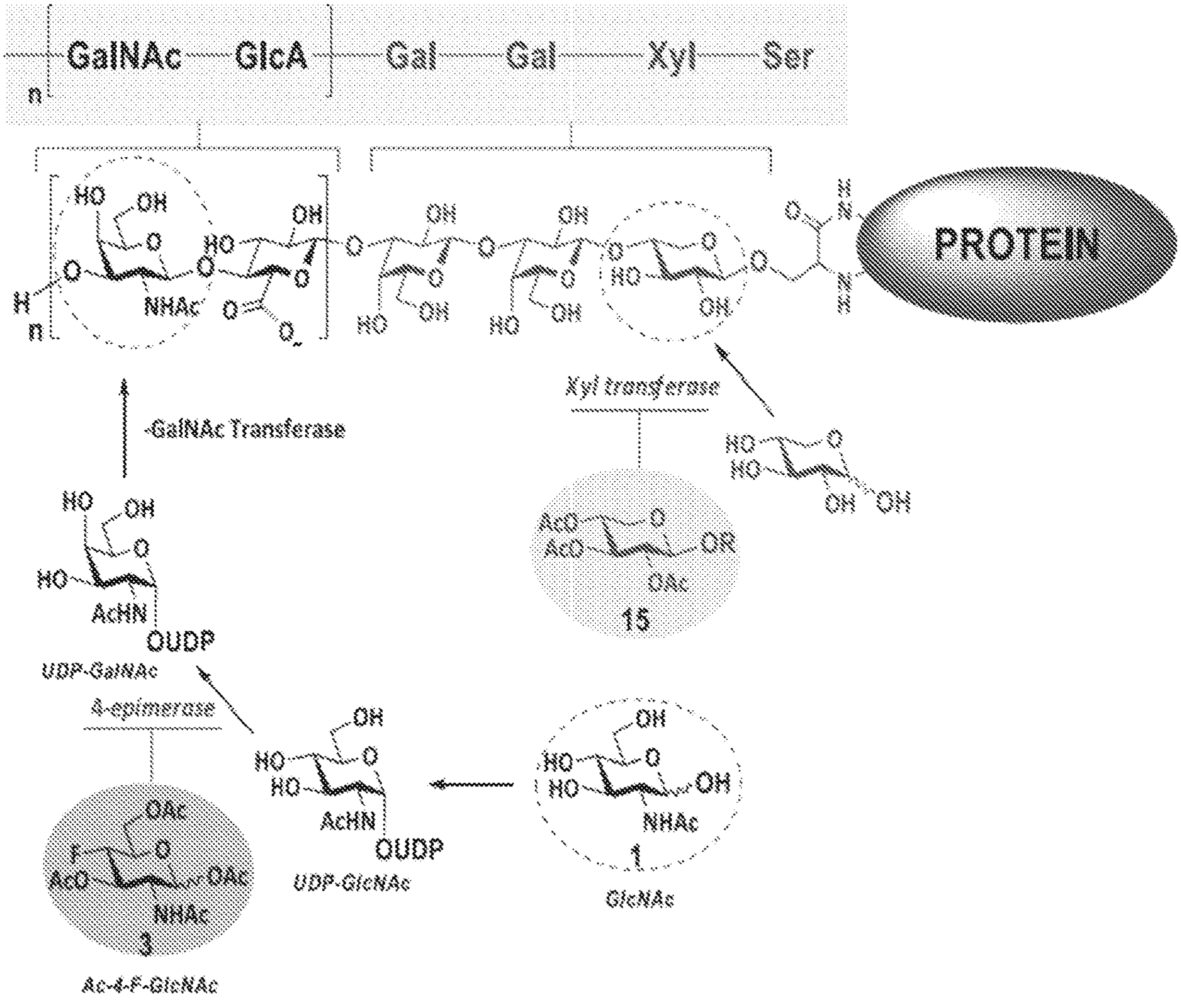
FIG. 1 depicts synthesis of CSPGs. Following formation of trisaccharide linker (xylose, galactose, galactose), chondroitin sulfate GAG chains are elongated with the disaccharides glucuronic acid (GlcA) and N-acetyl-galactosamine (GalNAc). UDP-GalNAc is created from UDP-N-acetylglucosamine (UDP-GlcNAc) by the enzyme 4-epimerase through an oxidation and reduction process. Fluorinated analogs (3, blue) perturb chondroitin sulfate GAG synthesis, potentially by acting as inhibitors of 4-epimerase. Xyloside analogs (15, yellow) perturb synthesis by competing for binding with xyloside.
Figure 3A:
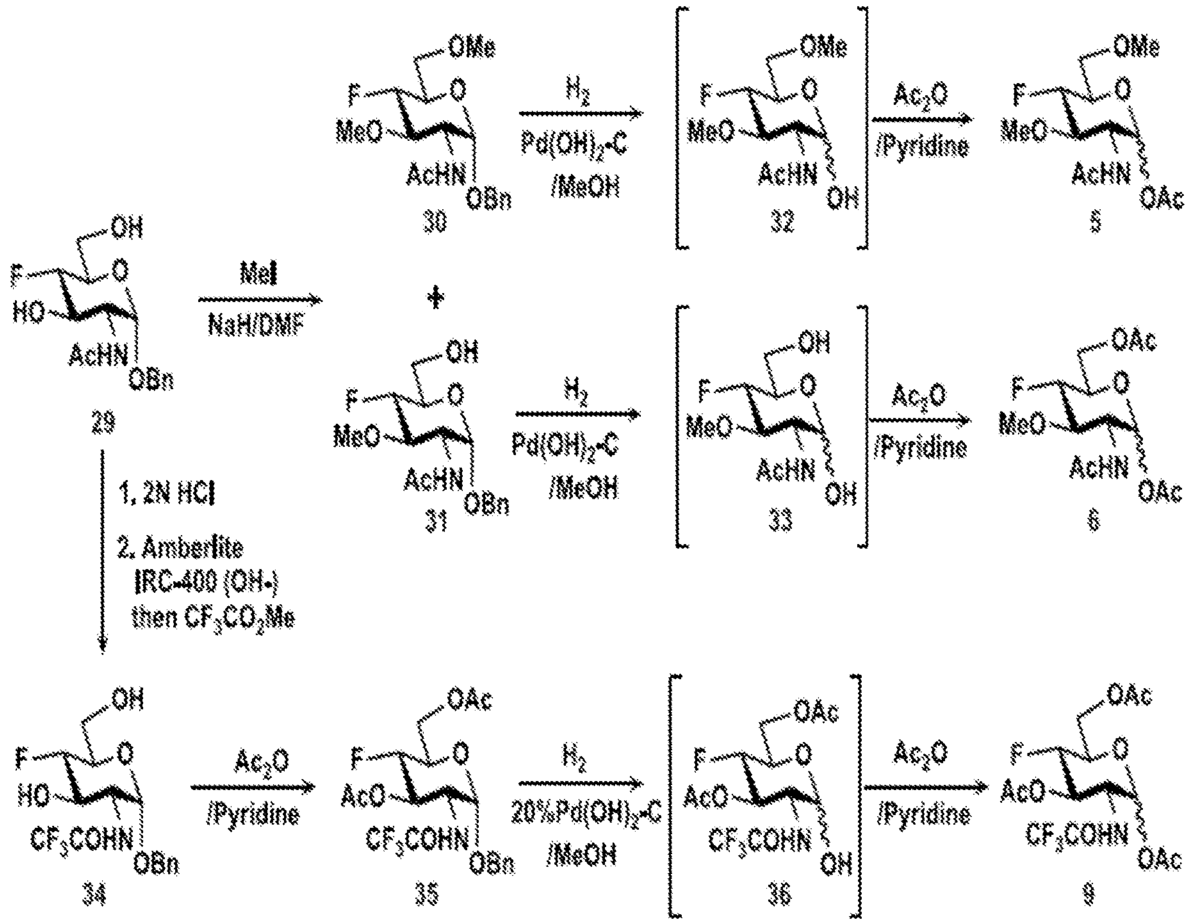
FIG. 3 depicts synthesis steps of fluorinated glucosamine derivatives 5, 6, 9 (A); 7, 8, 11, 12 (B); 13, 15 (C); 16, 17 (D); 18 (E); and, synthesis steps of xylosides 20, 21 (E); 22, 23, 24, 25 (F); 26, 27, 28 (G).
Figure 3B:
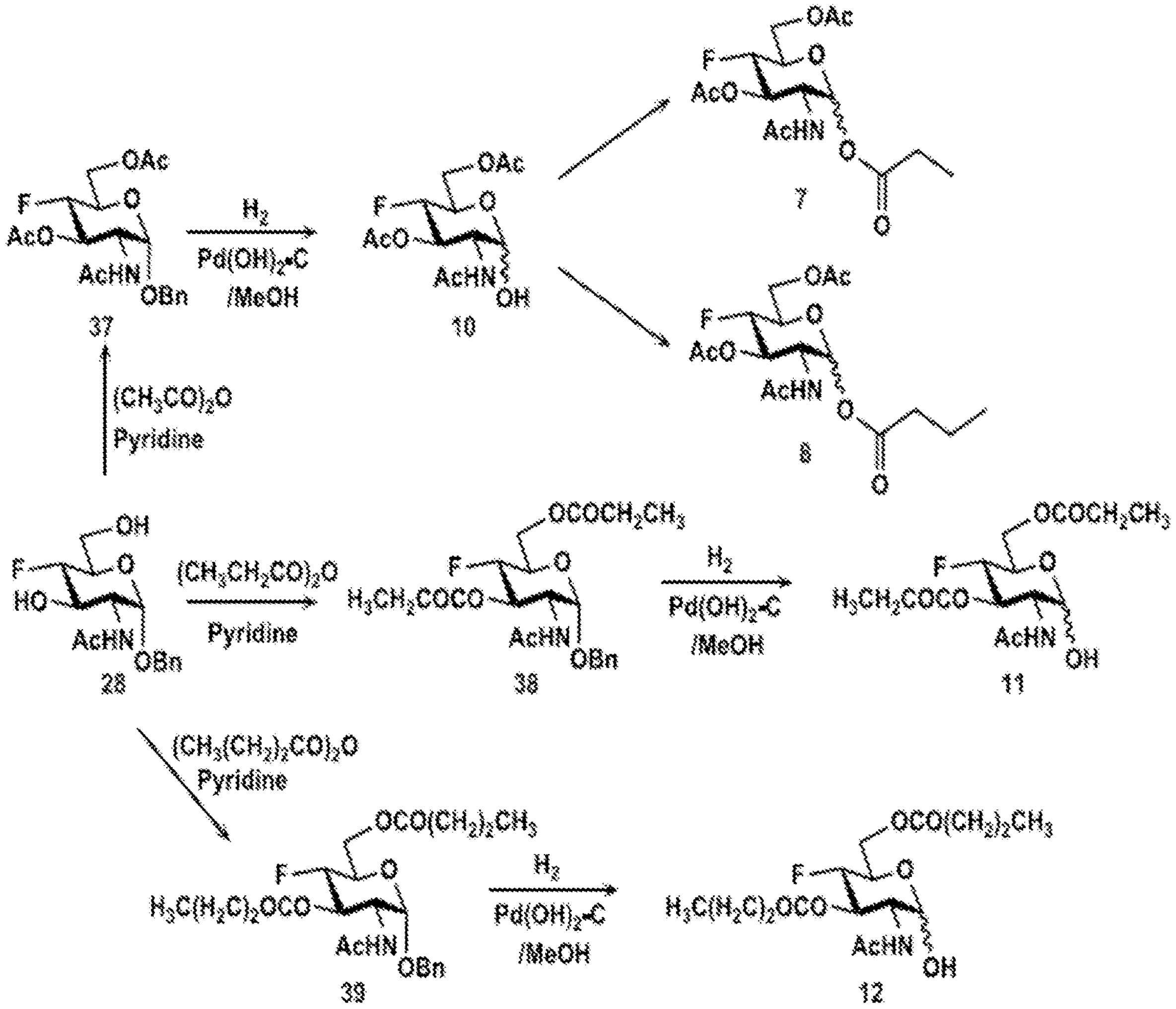
Figure 3C:
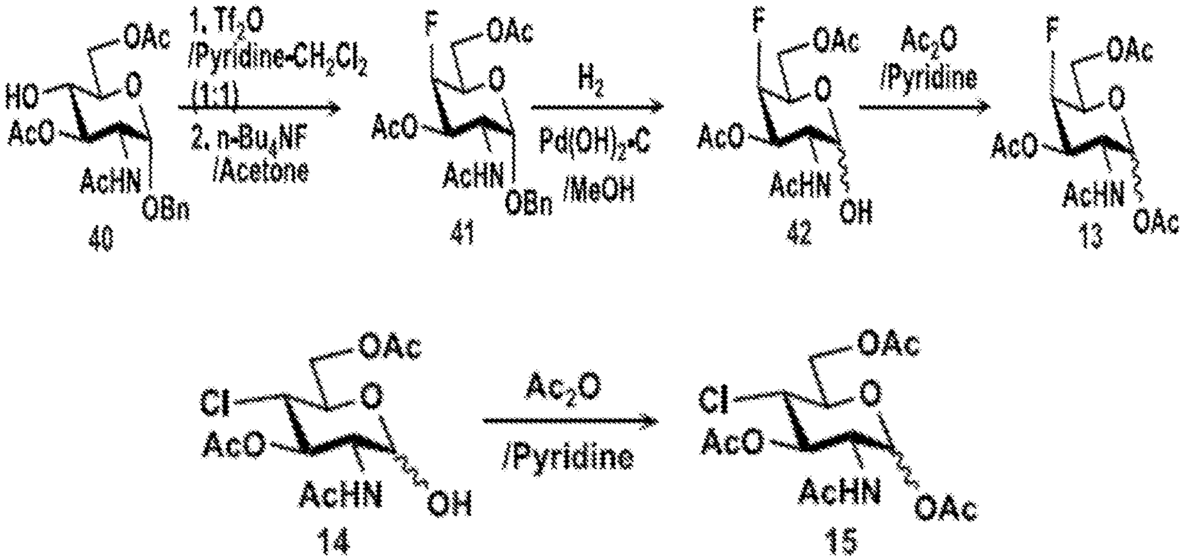
Figure 3D:
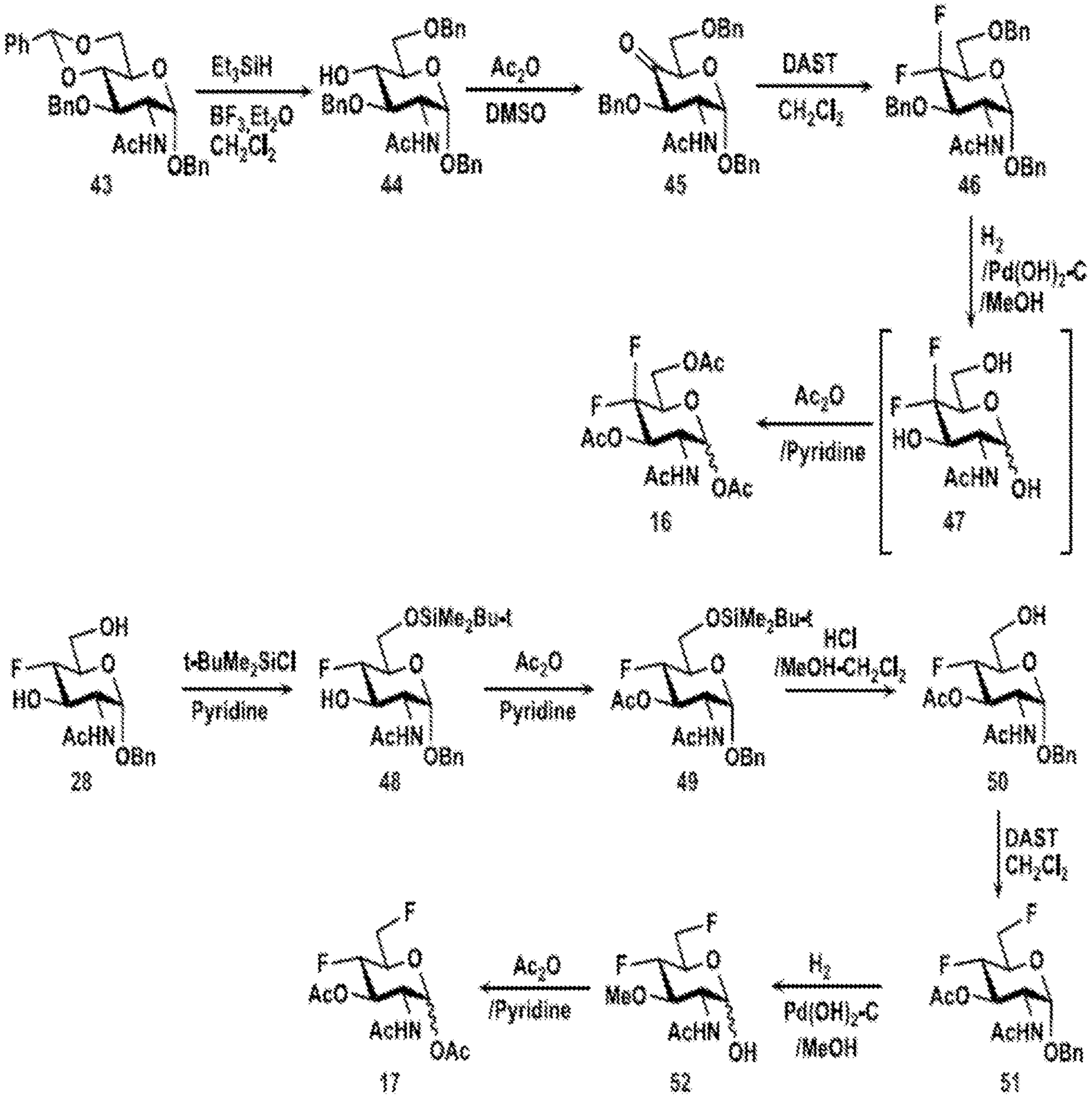
Figure 3E:
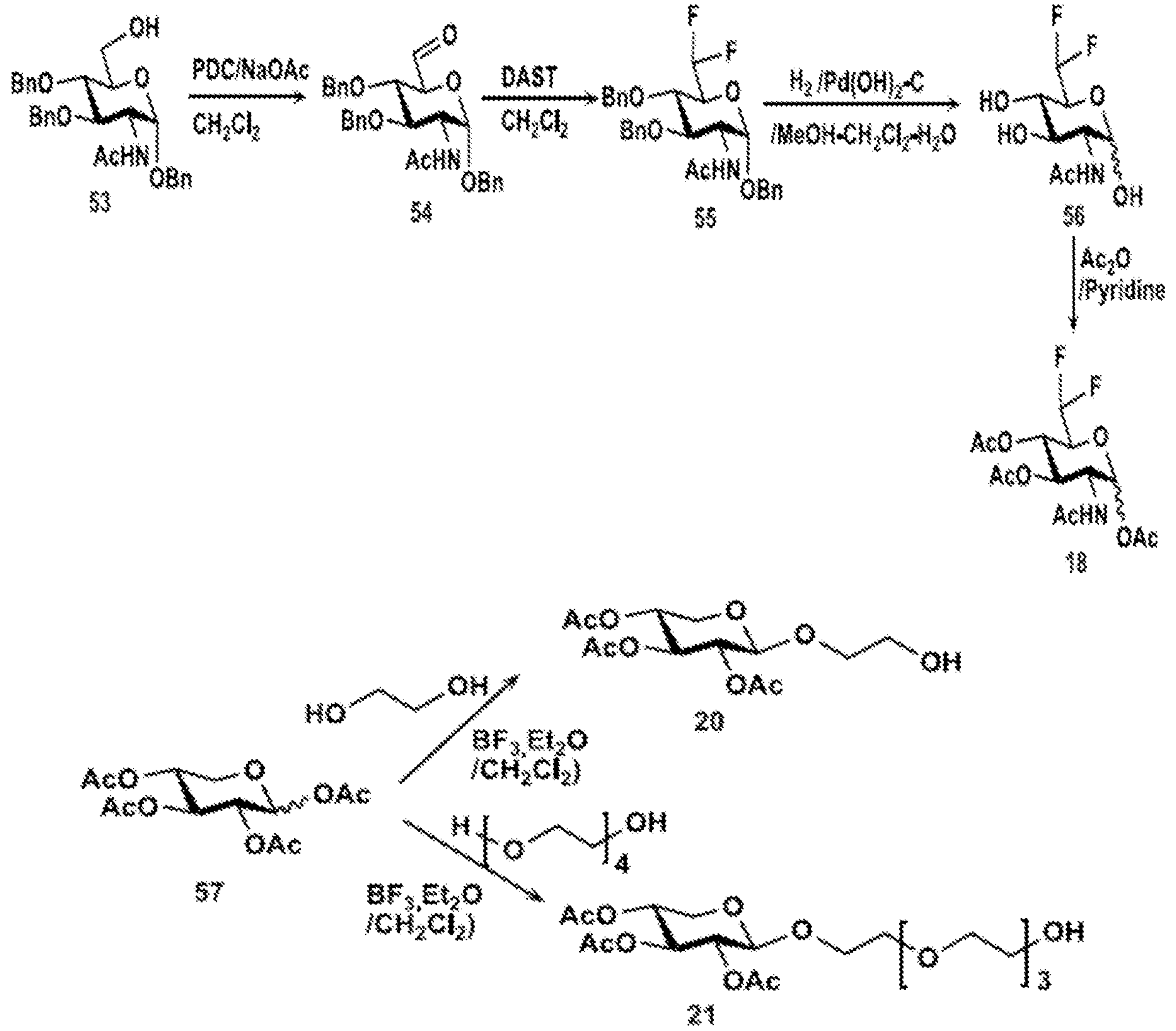
Figure 3F:
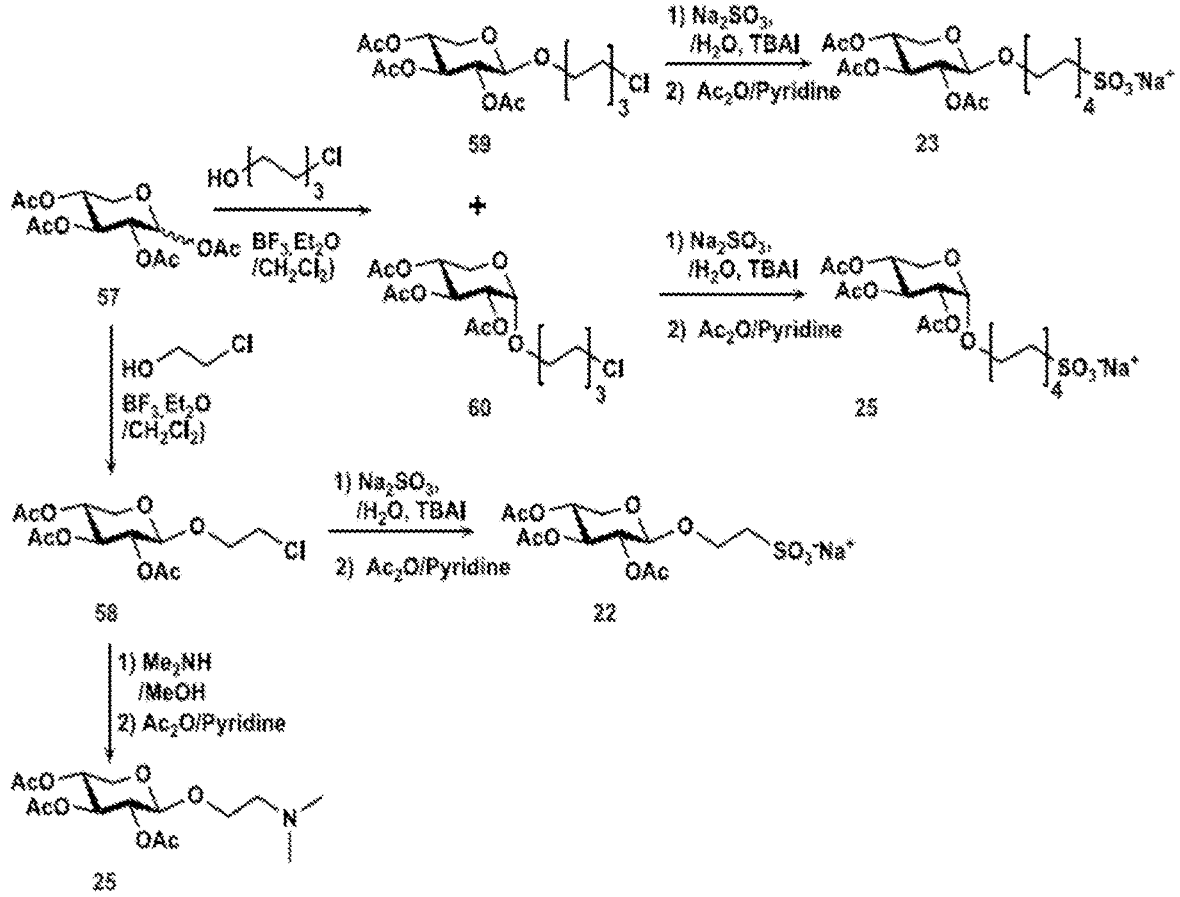
Figure 3G:
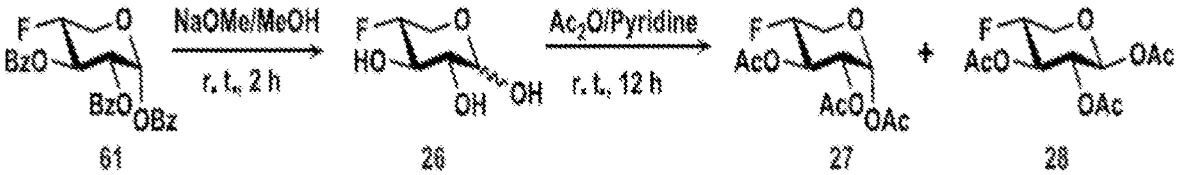

Imaris-quantified CD45+ cells and their distance from perivascular cuffs (0 μM, 0-5 μm, 5-10 μm, 10-20 μm, 20-30 μm, 30-40 μm, 40-50 μm, and 50-100 μm). A two-way repeated measures ANOVA with Sidak's multiple comparison test found an overall significant difference between the vehicle and Ac-4,4-diF-GlcNAc 16 distances (*, $p<0.05$), and a significant difference between the number of CD45+ cells vehicle and Ac-4,4-diF-GlcNAc 16 at 50-100 μm (***, $p<0.001$). (E) EAE experiment of Ac-4-F-GlcNAcOH (10) (n=6 mice each group) daily 50 mg/kg intraperitoneal treatment from day 7 to day 15.

DETAILED DESCRIPTION

In some aspects there is described compounds, compositions, methods, and uses, for treating a subject having or suspected of having an inflammatory disease or disorder.

As used herein, "inflammatory disease or disorder" may include diseases or disorders associated with inflammation or have an inflammation component.

In some example, the inflammatory disease or disorder may include, but is not limited to, a disease or disorder of the central nervous system (CNS), multiple sclerosis (MS), epilepsy, brain ischemia, Alzheimer's disease, experimental autoimmune encephalomyelitis (EAE) and traumatic brain injury, stroke, ALS, Huntington's disease, Parkinson's disease, an autoimmune disease or disorder, and/or a cancer.

In some examples, the compounds and compositions described herein may be used in inhibiting cell migration, cell proliferation or cell differentiation. Examples of tissue inflammation include, but are not limited to chronic inflammation and cutaneous inflammation.

In some example, the compounds and compositions inhibit cell proliferation, cell migration, cell differentiation, and/or production of signaling molecules. In some examples, the cell is a leukocyte, a cancerous cell, or a resident glial cell.

As used herein, "multiple sclerosis" includes multiple sclerosis or a related disease, and optionally refers to all types and stages of multiple sclerosis, including, but not limited to: benign multiple sclerosis, relapsing remitting multiple sclerosis, secondary progressive multiple sclerosis, primary progressive multiple sclerosis, progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, and acute multiple sclerosis. Optionally, "conditions relating to multiple sclerosis" include, e.g., Devic's disease, also known as Neuromyelitis Optica; acute disseminated encephalomyelitis, acute demyelinating optic neuritis, demyelinative transverse myelitis, Miller-Fisher syndrome, encephalomyelradiculoneuropathy, acute demyelinative polyneuropathy, tumefactive multiple sclerosis and Balo's concentric sclerosis.

As used herein, "progressive" multiple sclerosis refers to forms of the disease which progress towards an ever-worsening disease state over a period of time. Progressive multiple sclerosis includes, for example, primary progressive multiple sclerosis, secondary progressive multiple sclerosis, and progressive relapsing multiple sclerosis.

These subtypes may or may not feature episodic flare-ups of the disease, but are each associated with increased symptoms, such as increased demyelination or pain and reduced capacity for movement, over time.

The term "Alzheimer's Disease" (AD) generally refers to a mental deterioration in a subject, which clinical manifestations may include, but are not limited to, clinically in progressive memory deficits, confusion, behavioral problems, inability to care for oneself, gradual physical deterioration and, ultimately, death. Alzheimer's Disease may include preclinical AD, Mild cognitive impairment (MCI), and/or Alzheimer's dementia.

The term "cancer" may relates generally to a class of diseases or conditions in which abnormal cells divide without control and can invade nearby tissues.

The term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood).

The term "metastasize" refers to the spread of cancer from one part of the body to another. A tumor formed by cells that have spread is called a "metastatic tumor" or a "metastasis." The metastatic tumor contains cells that are like those in the original (primary) tumor.

The term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

The term "subject", as used herein, refers to an animal, and can include, for example, domesticated animals, such as cats, dogs, etc., livestock (e.g., cattle, horses, pigs, sheep, goats, cervids, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The term "treatment" or "treat" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable.

"Treating" and "Treatment" can also mean prolonging survival as compared to expected survival if not receiving treatment.

"Treating" and "treatment" as used herein also include prophylactic treatment. For example, a subject in the early stage of disease can be treated to prevent progression or alternatively a subject in remission can be treated with a compound or composition described herein to prevent progression.

In one example the treatment is in vitro treatment. In one example the treatment is in vivo treatment. In one example the treatment is ex vivo treatment.

In one aspect, there is described a compound selected from:

a compound of formula (7)

7

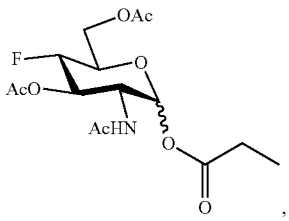
, a compound of formula (8)

8

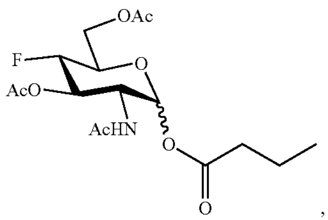
, a compound of formula (10)

10

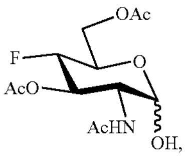

a compound of formula (11)

11

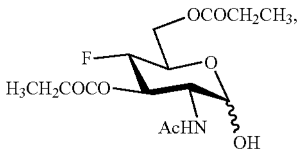

a compound of formula (17)

17

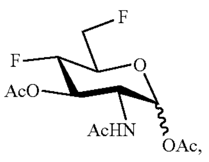

a compound of formula (18)

18

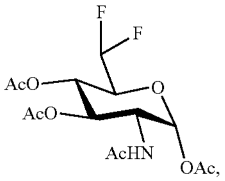

a compound of formula (21)

21

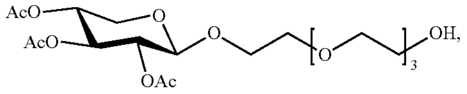

a compound of formula (23)

23

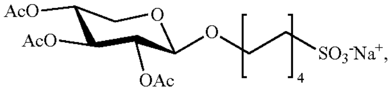

or a stereoisomer, a racemate, a tautomer, a pharmaceutically acceptable salt, a solvate, prodrug, or a functional derivative thereof.

In an aspect there is provided a compound of formula (62)

62

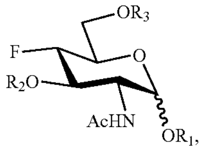

where any of the R1, R2 and R3 groups of the formula can be a H or an acyl group, or a stereoisomer, a racemate, a tautomer, a pharmaceutically acceptable salt, a solvate, a prodrug, or a functional derivative thereof. In an example, R2 and R3 are either an acetyl group or propanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (63)

63

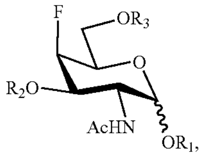

where any of the R1, R2 and R3 groups of the formula can be a H or an acyl group, or a stereoisomer, a racemate, a tautomer, a pharmaceutically acceptable salt, a solvate, a prodrug, or a functional derivative thereof. In an example R2 and R3 are either an acetyl group or propanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (64)

64

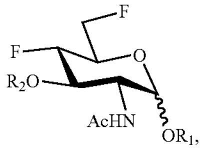

where any of the R1 and R2 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (65)

65

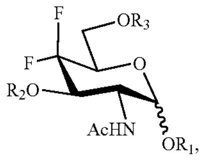

where any of the $R_1$, $R_2$ and $R_3$ groups of the formula can be a H or an acyl group, or a stereoisomer, a racemate, a tautomer, a pharmaceutically acceptable salt, a solvate, a prodrug, or a functional derivative thereof. In an example R2 and R3 are either an acetyl group or propanoyl or butanoyl, and R1 is either a H or an acyl group with formula $C_nH_{2n+1}CO$— (n=2-9), a stereoisomer, a racemate, a tautomer, a pharmaceutically acceptable salt, a solvate, a prodrug, or a functional derivative thereof.

In an aspect there is provided a compound of formula (66)

66

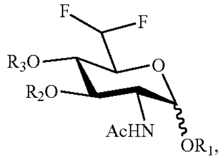

where any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (67)

67

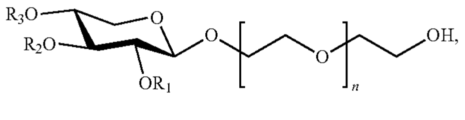

where n=0-20, any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (68)

68

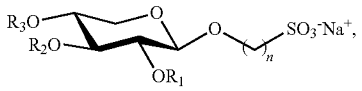

where n=2-12, and any of the R1, R2 and R3 groups of the formula can be a H or an acyl group, or a stereoisomer, a racemate, a tautomer, a pharmaceutically acceptable salt, a solvate, a prodrug, or a functional derivative thereof.

In an aspect there is provided a compound of formula (7)

7

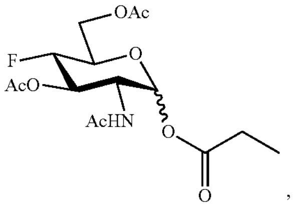

a compound of formula (8)

8

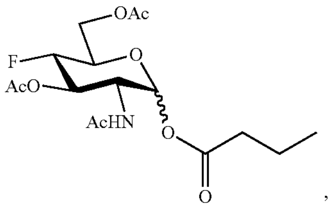

a compound of formula (10)

10

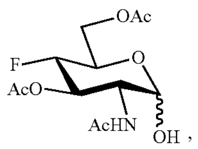

a compound of formula (11)

11

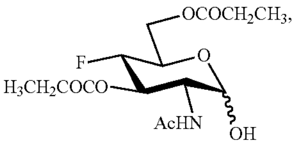

a compound of formula (17)

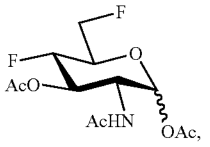

17 a compound of formula (18)

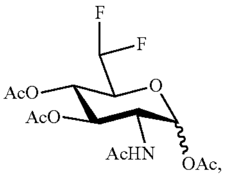

18 a compound of formula (21)

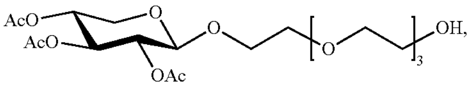

21 a compound of formula (23)

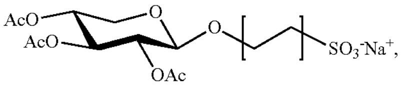

23 a compound of formula (16)

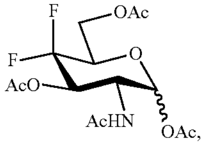

16 a compound of formula (13)

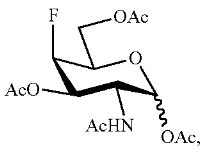

13 a stereoisomer, a racemate, a tautomer, a pharmaceutically acceptable salt, a solvate, a prodrug, or a functional derivative thereof.

As used herein, a "compound" refers to the compound itself, including stereoisomers and tautomers thereof, and its pharmaceutically acceptable salts, solvates, hydrates, complexes, esters, prodrugs and/or salts of prodrugs, unless otherwise specified within the specific text for that compound. Except, when otherwise indicated, e.g. by indication of (R) or (S) configuration at a given location, all stereoisomers of the compounds of the instant invention are contemplated, either in admixture or in pure or substantially pure form. Consequently, compounds described herein may exist in enantiomeric or racemic or diastereomeric forms or as mixtures thereof. The processes for preparation can utilize racemates or enantiomers as starting materials. When racemic and diastereomeric products are prepared, they can be separated by conventional methods, which for example are chromatographic or fractional crystallization.

The term "derivative", "functional derivative" and "physiologically functional derivative" as used herein means an active compound with equivalent or near equivalent physiological functionality to the named active compound when used and/or administered as described herein. As used herein, the term "physiologically functional derivative" includes any pharmaceutically acceptable salts, solvates, esters, prodrugs derivatives, enantiomers, or polymorphs.

The term "solvate" refers to a complex of variable stoichiometry formed e.g. by a compound of formula (1) and a solvent. The solvent is a pharmaceutically acceptable solvent, such as water, which should not interfere with the biological activity of the solute. Some compounds of the present invention can exist in a tautomeric form which are also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form.

The compounds, salts and prodrugs of the present invention can exist in several tautomeric forms, and such tautomeric forms are included within the scope of the present invention.

Tautomers exist as mixtures of a tautomeric set in solution. In solid form, usually one tautomer predominates. Even though one tautomer may be described, the present invention includes all tautomers of the present compounds.

The term "prodrug" used herein refers to compounds which are not pharmaceutically active themselves but which are transformed into their pharmaceutical active form in vivo, for example in the subject to which the compound is administered.

Prodrug and derivatives of niacin, or pharmaceutically acceptable salts or solvates thereof, can be prepared by methods known to those of ordinary skill in the art.

As used herein, a "subject having an inflammatory disease or disorder" is a subject known or diagnosed to have an inflammatory disease or disorder. Generally a subject having an inflammatory disease or disorder will have some objective manifestation of the inflammatory disease or disorder, such as a sign, symptom, or result of a suitable diagnostic test that indicates the presence of the inflammatory disease or disorder.

In some examples, a subject at risk of developing an inflammatory disease or disorder is a subject with a known or suspected predisposition to develop an inflammatory disease or disorder. This may include, but is not limited to a family history to an inflammatory disease or disorder.

In some examples, treatment methods comprise administering to a subject a therapeutically effective amount of a compound or composition described herein and optionally consists of a single administration or application, or alternatively comprises a series of administrations or applications.

In some examples there is described a pharmaceutical composition comprising a compound of Formula (7), Formula (8), Formula (10), Formula (11), Formula (17), Formula (18), Formula (21), Formula (23), or a compound of formula (16)

16

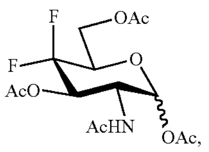

or a compound of formula (13)

13

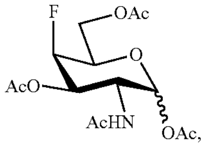

or a stereoisomer, a racemate, a tautomer, a pharmaceutically acceptable salt, a solvate, a prodrug, or a functional derivative thereof.

In some examples there is described a pharmaceutical composition comprising a compound of Formula (62), Formula (63), Formula (64), Formula (65), Formula (66), Formula (67), Formula (68), Formula (7), Formula (8), Formula (10), Formula (11), Formula (17), Formula (18), Formula (21), Formula (23), or a compound of formula (16) or a compound of formula (13), or a stereoisomer, a racemate, a tautomer, a pharmaceutically acceptable salt, a solvate, a prodrug, or a functional derivative thereof.

In some examples, the compound or pharmaceutical composition is a therapeutically effective amount.

The term "therapeutically effective amount", as used herein, refers to an amount effective, at dosages and for periods of time necessary to achieve the desired result. Effective amounts may vary according to factors such as the disease state, age, sex and/or weight of the subject. The amount of a given compound or composition that will correspond to such an amount will vary depending upon various factors, such as the given drug or compound, the pharmaceutical formulation, the route of administration, the identity of the subject being treated, and the like, but can nevertheless be routinely determined by one skilled in the art.

The compounds and/or compositions described herein may be administered either simultaneously (or substantially simultaneously) or sequentially, dependent upon the condition to be treated, and may be administered in combination with other treatment(s). The other treatment(s), may be administered either simultaneously (or substantially simultaneously) or sequentially.

Administration may be by any suitable means.

Routes of administration include, but are not limited to, injection (subcutaneous, intravenous, parenterally, intraperitoneally, intrathecal), oral, inhalation, rectal and transdermal. The pharmaceutical compositions may be given by forms suitable for each administration route. For example, these compositions are administered in tablets or capsule form, by injection, inhalation, eye lotion, ointment, suppository, etc. administration by injection, infusion or inhalation; topical by lotion or ointment; and rectal by suppositories. The injection can be bolus or can be continuous infusion. Depending on the route of administration, a compound or composition described herein can be coated with or disposed in a selected material to protect it from natural conditions which may detrimentally affect its ability to perform its intended function. A compound or composition described herein can be administered alone, or in conjunction with either another agent as described above or with a pharmaceutically-acceptable carrier, or both. A compound or composition described herein can be administered prior to the administration of the other agent, simultaneously with the agent, or after the administration of the agent. Furthermore, a compound described herein can also be administered in a pro-drug form which is converted into its active metabolite, or more active metabolite in vivo.

Administering can also be performed, for example, once, a plurality of times, and/or over one or more extended periods.

In some examples, the compound is formulated as a pharmaceutical composition, which is pharmaceutically acceptable.

The phrase "pharmaceutically acceptable" indicates that the substance or composition must be compatible chemically and/or toxicologically, with the other ingredients comprising a formulation, and/or the subject being treated.

The compound may be formulated with pharmaceutically acceptable carriers, excipients or diluents.

Pharmaceutically acceptable carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions as described herein may be sterilized by conventional methods and/or lyophilized.

In one example, treatment comprises administration of a therapeutically effective amount of a compound or a pharmaceutical composition to the central nervous system (CNS) of a subject.

In one example, treatment provides one or more compound or composition described herein, to the tissues of the CNS by administration directly into the cerebrospinal fluid (CSF).

In some examples, delivery to the CSF and brain include, but are not limited to, intrathecal (IT), intracerebroventricular (ICV), and intraparenchymal administration. Intrathecal and intracerebroventricular administration may be carried out through the use of surgically implanted pumps that infuse the therapeutic agent into the cerebrospinal fluid. Intraparenchymal delivery may be carried out by the surgical placement of a catheter into the brain.

As used herein, "delivery to the CSF" and "administration to the CSF" encompass the IT infusion or ICV infusion of one or more compounds or compositions as described herein through the use of an infusion pump. In some embodiments, IT infusion is a suitable means for delivery to the CSF. In other examples, one or more compounds or compositions as described herein is continuously infused into the CSF for the entire course of treatment; such administration is referred to as "continuous infusion" or, in the case of IT infusion, "continuous IT infusion." Also contemplated is continuous intraparenchymal infusion using a pump.

In some examples, an infusion pump is employed to deliver one or more compounds or compositions as described herein to the CNS. Such infusion pumps and their method of implantation and use are known to the skilled worker. In a specific example, the Medtronic SyncroMed® II pump, is employed. The SyncroMed® II pump is surgically implanted according the procedures set forth by the manufacturer. The pump contains a reservoir for retaining a drug solution, which is pumped at a programmed dose into a catheter that is surgically implanted.

Methods of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLE 1: TARGETING THE CHONDROITIN SULFATE PROTEOGLYCANS: EVALUATING FLUORINATED GLUCOSAMINES AND XYLOSIDES IN SCREENS PERTINENT TO MULTIPLE SCLEROSIS

CSPG synthesis involves the creation of a protein core, and covalent attachment of numerous glycosaminoglycan (GAG) side chains (FIG. 1). The first step of GAG synthesis is the linkage of xylose to a serine of the core protein (FIG. 1). Following extension of the xylose into a trisaccharide linker (xylose, galactose, galactose), chondroitin sulfate GAG chains are elongated with the repeating disaccharides glucuronic acid (GlcA) and N-acetyl-galactosamine (GalNAc) (FIG. 1). UDP-N-acetyl-galactosamine (UDP-GalNAc) is created from UDP-N-acetyl-glucosamine (UDP-GlcNAc) by the enzyme 4-epimerase through an oxidation and reduction process [Prydz, K. & Dalen, K. T. Synthesis and sorting of proteoglycans. Journal of Cell Science 113, 193-205 (2000)]. The 4-fluorinated glucosamine analog 3, termed fluorosamine, has shown to have a remarkable ability to perturb GAG biosynthesis [Nigro, J. et al. Regulation of heparan sulfate and chondroitin sulfate glycosaminoglycan biosynthesis by 4-fluoro-glucosamine in murine airway smooth muscle cells. The Journal of biological chemistry 284, 16832-16839 (2009); van Wijk, X. M. et al. A common sugar-nucleotide-mediated mechanism of inhibition of (glycosamino)glycan biosynthesis, as evidenced by 6F-GalNAc (Ac3). FASEB journal: official publication of the Federation of American Societies for Experimental Biology 29, 2993-3002 (2015)], potentially by acting as an inhibitor to 4-epimerase to prevent GAG elongation; fluorosamine may also deplete UTP and thus reduce UTP availability for sugar precursors (FIG. 1).

Chondroitin sulfate proteoglycans (CSPGs) are upregulated in insults to the central nervous system, including multiple sclerosis (MS), an inflammatory demyelinating condition of the central nervous system. CSPGs appear to be detrimental in MS as they enhance immune responses and act as barriers to remyelination. Despite their deleterious roles, strategies to selectively reduce CSPG production are lacking. Herein described is development, screening, and description of synthetic sugar analogs that interfere with CSPG biosynthesis, have potential to promote outgrowth of oligodendrocyte precursor cells in an inhibitory environment, and can lower inflammation by attenuating proliferation of T lymphocytes. Described herein are activities of peracetylated-4,4-difluoro-N-acetylglucosamine (Ac-4,4-diF-GlcNAc) in vitro, which reduced inflammation and clinical severity in a mouse model of MS. Described herein are fluorinated glucosamine analogs that target CSPGs with the potential for use in MS and other neurological conditions.

Further, described herein is a synthesis of new analogs that display an increased potency and efficacy than the ones previously mentioned [Keough, M. B. et al. An inhibitor of chondroitin sulfate proteoglycan synthesis promotes central nervous system remyelination. Nature communications 7, 11312 (2016)]. Glucosamine analogs 5-18 were synthesized to target the 4-epimerase, and xylosides 19-28 were synthesized to disrupt attachment of xylose to the core protein. Chemical syntheses of compounds, and the evaluation of these compounds in various models pertinent to MS is also described. Highlighted are in vitro screening results and potent in vivo effects of a 4,4-difluoro glucosamine analog 16 (Ac-4,4-diF-GlcNAc) that attenuates severity of disease in an inflammatory animal model of MS, experimental autoimmune encephalomyelitis (EAE). These results highlight the efficacy of using a multi-faceted screen to identify new compounds for use in vivo, and that targeting CSPGs represent a promising therapeutic target in MS.

Synthesis of Compounds

Novel acetylated analogs of D-glucosamine were synthesized that were either monofluorinated (5-13) or difluorinated (16-18) with other substitutions to various carbon positions; compound 13 is also a derivative of N-acetyl-D-galactosamine. In addition, a series of water soluble per-O-acetylated D-xyloside derivatives 19-25 were produced, along with three 4-fluorinated D-xyloside derivatives 26-28. The chemical structures of compounds tested are listed in FIG. 2 and their chemical synthesis in FIG. 3A-G. It was previously described that compound 3 (Ac-4-F-GlcNAc, fluorosamine), the reference compound used herein, reduced production of CSPGs by astrocytes, promoted remyelination following lysolecithin demyelination of the mouse spinal cord, and attenuated the severity of mice afflicted with EAE [Keough, M. B. et al. An inhibitor of chondroitin sulfate proteoglycan synthesis promotes central nervous system remyelination. Nature communications 7, 11312 (2016)]. Compounds 5 and 6 are analogs of Ac-4-F-GlcNAc 3 with permanent protection at either both O3 and O6-positions or O3-position alone via O-methylation; the other GlcNAc derivatives 7-12 are all 4-fluorinated but with removable acyl protecting groups of various lengths at different positions; in particular, compound 9 has a trifluoroacetyl modification on the nitrogen and compounds 10-12 are hemiacetals because they have no acyl group at the anomeric position. Instead of 4-fluorination, the related GlcNAc derivative 14 was also a hemiacetal but with a 4-chlorination. Compound 13 does not have the GlcNAc configuration, instead, it has the N-acetylgalactosamine (GalNAc) configuration with a 4-fluorination. In contrast to all above compounds, three difluorinated derivatives have also been synthesized. Compounds 16 (Ac-4,4-diF-GlcNAc) has a 4,4-difluorination, making it unique because it combines the properties of 4-fluorinated derivatives of both GlcNAc and GalNAc series. For comparison, two other difluorinated compounds, 17 (Ac-4,6-diF-GlcNAc) and 18 (Ac-6,6-diF-GlcNAc), were also prepared. The xyloside family of synthesized compounds consists of derivatives bearing different types of polar groups for the purpose of enhancing their water-solubility such as compound 19, a non-acetylated benzyl β-xyloside known in the literature [Rivera-Sagredo, A. et al. 4-O-β-spD-Galactopyranosyl-spD-xylose: A new synthesis and application to the evaluation of intestinal lactase. Carbohydrate Research 228, 129-135 (1992)]. Derivatives 20-21 contain ethylene glycol units of different lengths (neutral), derivatives 22-24 contain alkyl sulfonates of different lengths, and derivative 25 contains an amine functionality at the aglyone which can be protonated under physiological conditions. Additionally, the non-O-acetylated 4-fluorinated xylose and its two per-O-acetylated α-anomer 27 and β-anomer 28 were synthesized. It was considered that 4-fluorination may prevent subsequent glycan extension, thus potentially inhibiting the biosynthesis of CSPGs.

Sugar Analogs Reduce CSPG Production by Astrocytes

Figure 4A:
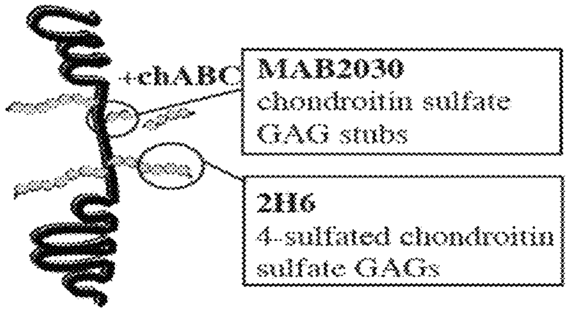
FIG. 4 depicts fluorinated glucosamines that reduce the synthesis of CSPGs by astrocytes. a, Schematic of where MAB2030 (after chondroitinase ABC treatment) and 2H6 are reported to bind on CSPGs. b, Combined chemical structure of the 5 compounds that most effectively reduced CSPG production (Ac-4,4-diF-GlcNAc 16, Ac-4-F-GlcNA-cOH 10, Ac-4-F-GalNAc 13, Ac-4-F-GlcNAcOPr 7, Ac-4-F-GlcNAc 3). c, Representative western blot for stub chondroitin-4-sulfate attached to the core protein (MAB2030) shows the effectiveness of certain N-acetyl-D-glucosamine derivatives at reducing CSPG production in astrocytes, as determined by sampling of the astrocyte conditioned medium in treated cells. d, Representative western blot of conditioned media for intact chondroitin-4-sulfate (2H6) in astrocytes treated with N-acetyl-D-glucosamine derivatives. e, Relative band densities of MAB2030 in conditioned media of treated astrocytes versus untreated (control) astrocytes. Column represents the average relative band densities calculated from three independent Western blots except for the following compounds that were tested in four: GlcNAc, DMSO, Ac-4-Cl-GlcNac 15, Ac-4-F-GlcNAc 3, and Ac-4,4-diF-GlcNAc 16. $^*P<0.05$, $^{}P<0.01$, $^{**}P<0.0001$, one-way analysis of variance (ANOVA) with Dunnett's post hoc test (respective of DMSO control). Error bars are mean±s.d.

Astrocytes are major producers of CSPGs following injury in the CNS [Jones, L. L., Margolis, R. U. & Tuszynski, M. H. The chondroitin sulfate proteoglycans neurocan, brevican, phosphacan, and versican are differentially regulated following spinal cord injury. Experimental Neurology 182, 399-411 (2003); Tang, X., Davies, J. E. & Davies, S. J. Changes in distribution, cell associations, and protein expression levels of NG2, neurocan, phosphacan, brevican, versican V2, and tenascin-C during acute to chronic maturation of spinal cord scar tissue. Journal of neuroscience research 71, 427-444 (2003); Asher, R. A. et al. Neurocan is upregulated in injured brain and in cytokine-treated astrocytes. The Journal of neuroscience: the official journal of the Society for Neuroscience 20, 2427-2438 (2000); McKeon, R. J., Jurynec, M. J. & Buck, C. R. The chondroitin sulfate proteoglycans neurocan and phosphacan are expressed by reactive astrocytes in the chronic CNS glial scar. The Journal of neuroscience: the official journal of the Society for Neuroscience 19, 10778-10788 (1999); Haas, C. A., Rauch, U., Thon, N., Merten, T. & Deller, T. Entorhinal cortex lesion in adult rats induces the expression of the neuronal chondroitin sulfate proteoglycan neurocan in reactive astrocytes. The Journal of neuroscience: the official journal of the Society for Neuroscience 19, 9953-9963 (1999)] and they may help drive progression of disability in a model of progressive MS [Mayo, L. et al. Regulation of astrocyte activation by glycolipids drives chronic CNS inflammation. Nature medicine 20, 1147-1156 (2014)]. Therefore astrocytes were used as model cells to determine the ability of the sugar analogs to reduce synthesis of CSPGs. Since CSPGs are exported out of cells, the conditioned media from analog-treated astrocytes were probed by Western blots (FIG. 4). We used antibodies to both the stubs of chondroitin sulfate GAGs attached to the core protein (MAB2030) and to intact 4-sulfated chondroitin sulfate sidechains (2H6) (FIG. 4*a*). Particularly, we used the 2H6 antibody to label intact 4-sulfated chondroitin sulfate sidechains, and the MAB2030 antibody to detect the stubs of chondroitin sulfate GAGs attached to the core protein. The latter is a correlate of proteoglycan core proteins based on previous studies that have found that this antibody recognizes only chondroitin GAG chains attached to the core protein, and not native proteoglycans or isolated GAGs [Glant T. T.; Buzás, E. I.; Finnegan, A.; Negroiu, G.; Cs-Szabó G.; Mikecz K. Critical roles of glycosaminoglycan side chains of cartilage proteoglycan (aggrecan) in antigen recognition and presentation *J. Immunol.* 1998, 160 (8), 3812-3819. Poole Poole C. A.; Glant T. T.; Schofield J. R.; Chondrons from articular cartilage. (IV). Immunolocalization of proteoglycan epitopes in isolated canine tibial chondrons. *J. Histochem. Cytochem.* 1991, 39 (9), 1175-1187].

Figure 4B:
Figure 4C:
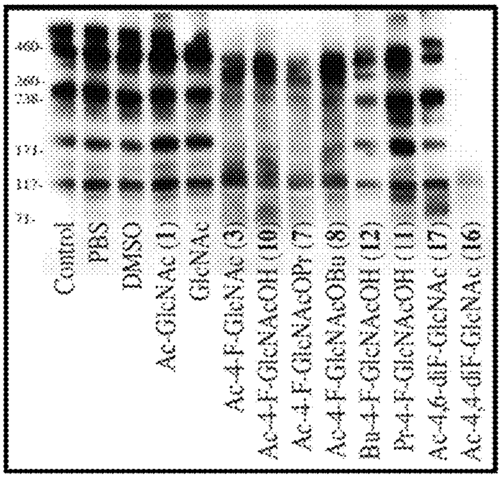
Figure 4E:
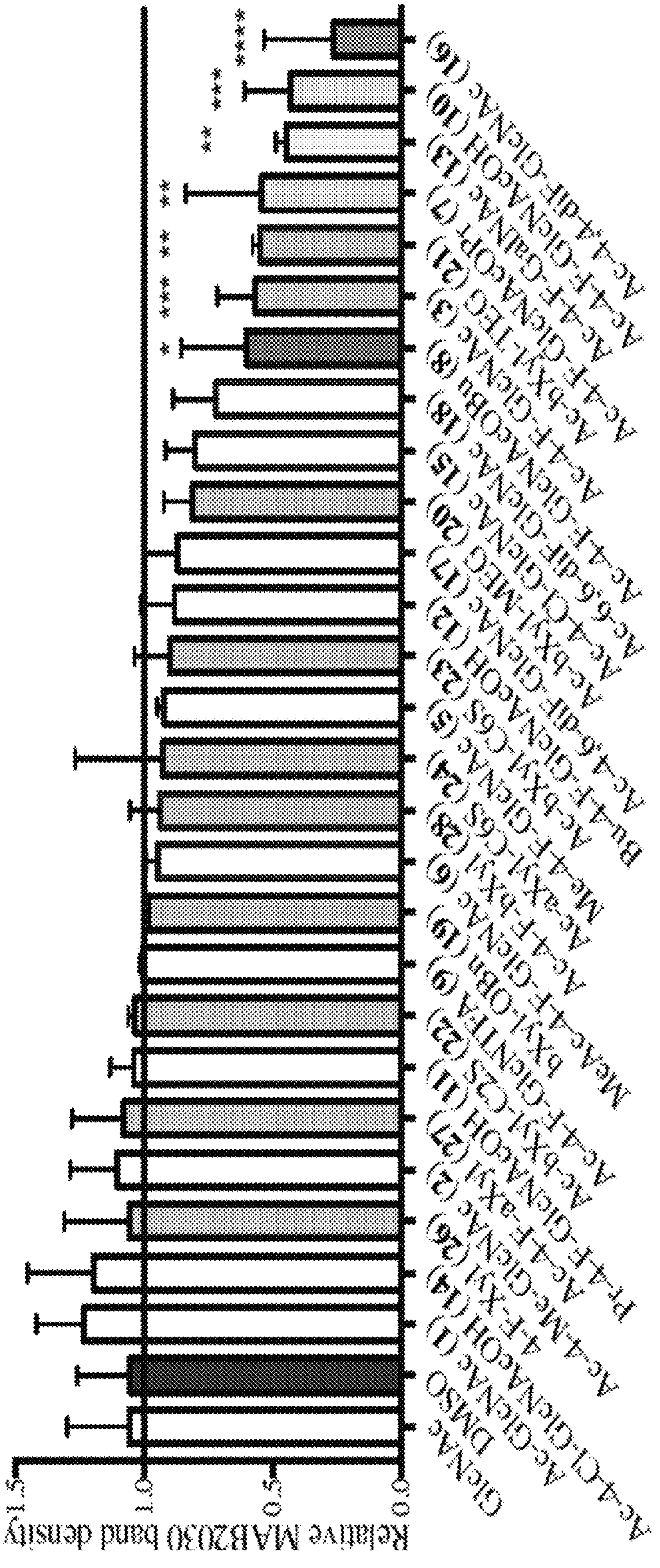
Figure 5A:
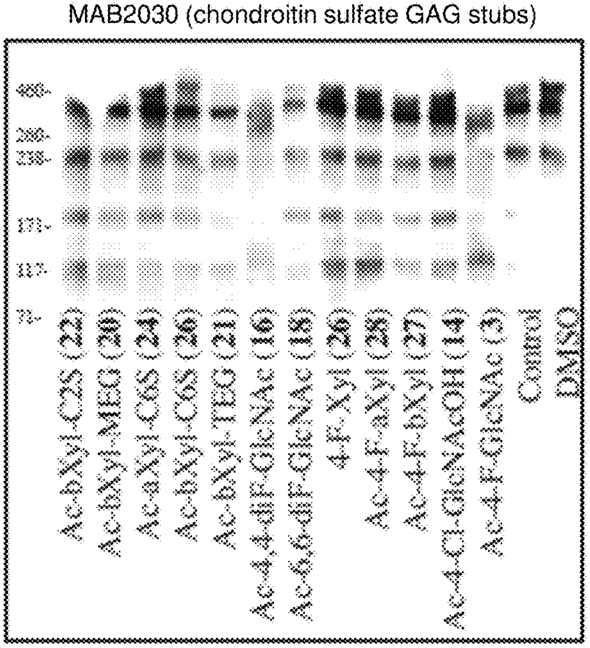
FIG. 5 depicts results of fluorinated glucosamines and xylosides that reduce the synthesis of CSPGs and HSPGs by astrocytes. a, Representative western blot of MAB2030 (chondroitin sulfate GAG stubs) and b, 4-sulfated GAGs produced by astrocytes treated by a variety of xylosides and glucosamines. c, Western blot of heparin sulfate GAGs (10E4) produced by astrocytes treated by glucosamine and xylose derivatives, showing a slight reduction by Ac-4,4-diF-GlcNAc 16 and Ac-4-F-GlcNAc 3.
Figure 6A:
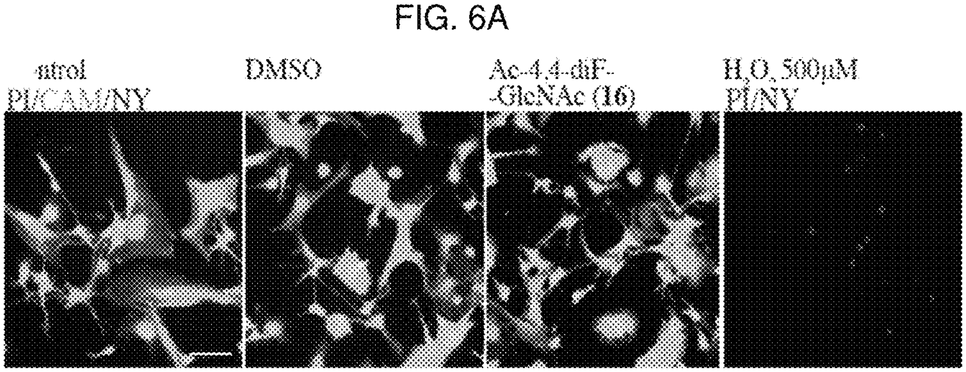
FIG. 6 depicts toxicity of compounds. a, Representative images of mouse astrocytes stained for propidium iodide (PI), calcein AM (CAM), and nuclear yellow (NY), following treatment with control (PBS), DMSO and 100 μM of Ac-4,4-diF-GlcNAc 16. Only the positive control $H_2O_2$ caused a significant increase in toxicity, as shown by propdidium iodide (PI)-positive cells (scale bar=50 μm). b, Quantified propidium iodide and calcein AM staining of mouse astrocyte cultures showing the percentage of cells (identified by nuclear yellow) that were propidium iodide positive (dead) and calcein AM positive (live). Astrocytes were treated with 100 μM of compounds for 48 hours and only the positive control $H_2O_2$ caused a significant increase in toxicity. c, ATP assay of neurons treated with 100 μM of select N-acetyl-D-glucosamine and xylose derivatives. d, Structure of the two compounds identified in neuronal cell ATP assay that reduced ATP production by greater than 50% (Ac-4-F-GlcNAcOH 3 and Pr-4-F-GlcNAcOH 11). $^*P<0.05$, $^{}P<0.01$, $^{**}P<0.0001$ one-way analysis of variance (ANOVA) with Dunnett's post hoc test (b,c) comparing treatments against control.

Using the MAB2030 antibody, it was found that fluorinated compounds (FIG. 4*c*) and xylosides (FIG. 5*a*) had a range in their capacity to reduce CSPG production. FIG. 4*e* shows the averaged relative MAB2030 band density of treated astrocytes over control astrocytes, ranking the compounds on their ability to reduce CSPG production across multiple independent experiments. Cultured astrocytes treated with sugar analogs did not show any distinct morphological changes or toxicity from treatment (FIG. 6*a,b*). The non-acetylated GlcNAc and peracetylated Ac-GlcNAc (1) did not affect CSPG production; CSPG reduction required the 4-fluorinated analogs but not the 4-chlorinated compounds 14 (Ac-4-Cl-GlcNAcOH) and 15 (Ac-4-Cl-GlcNAc). The best 4-fluoro glucosamine analogs that significantly reduced chondroitin sulfate GAG stubs by 25% or more were (from best to least): the 4,4-difluorinated 16 (Ac-4,4-diF-GlcNAc), the 4-monofluorinated hemiacetal 10 (Ac-4-F-GlcNAcOH), the anomeric O-propanoate 7 (Ac-4-F-GlcNAcOPr), Ac-4-F-GlcNAc 3, and anomeric O-butanoate 8 (Ac-4-F-GlcNAcOBu). The acetylated 4-fluorinated GalNAc derivative 13 (Ac-4-F-GalNAc) also significantly reduced chondroitin sulfate GAGs. In general, the compounds that reduced chondroitin sulfate GAG stubs by greater than 25% had substitutions on only anomeric carbon (C-1) with O-acetyl group (3), hydroxyl group (10) or O-propanoate (7), and a fluorine at C-4 or difluorination at C-4 (16) (FIG. 4*b*). The efficacy of these compounds may be in part due to their O-acylations and similar structure and molecular weight as Ac-GlcNAc (1), allowing them to easily cross the plasma membrane. Following an enzymatic O-deacylation by esterases, their O-deacylated derivatives are likely to be converted to the corresponding UDP-sugar derivatives that subsequently act as inhibitors to the 4-epimerase, due to their 4-fluorination.

Figure 14A:
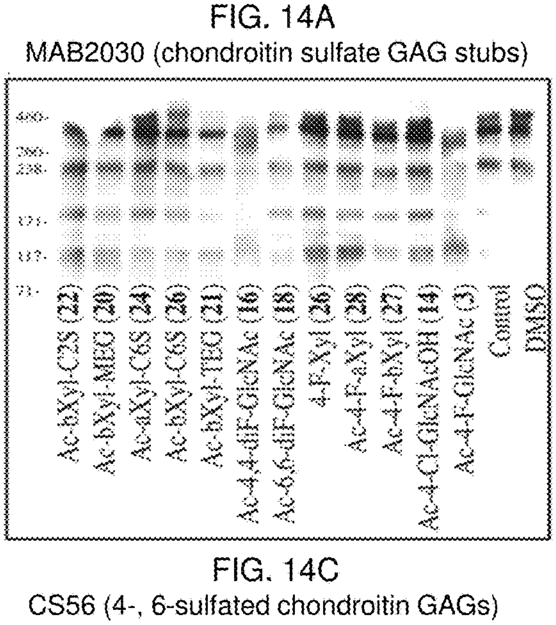
FIG. 14 depicts fluorinated glucosamines and xylosides reduce the synthesis of CSPGs and HSPGs by astrocytes. (A) Representative western blot of MAB2030 (chondroitin sulfate GAG stubs) and (B) 4-sulfated GAGs produced by astrocytes treated with a variety of xylosides and glucosamines. (C) Western blot with CS56 antibody against 4- and 6-sulfated GAG chains. (D) Probing for heparan sulfate GAGs (10E4) shows a reduction by Ac-4-F-GlcNAc 3 and Ac-4,4-diF-GlcNAc 16. (E) MAB2030 western blot of astrocyte cell lysates showing less immunoreactive bands in cultures treated with compounds previously found to reduce CSPG levels in the conditioned media.
Figure 14B:
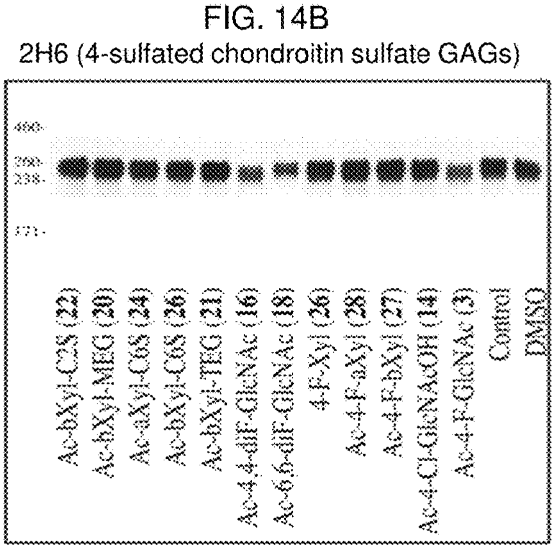
Figure 14C:
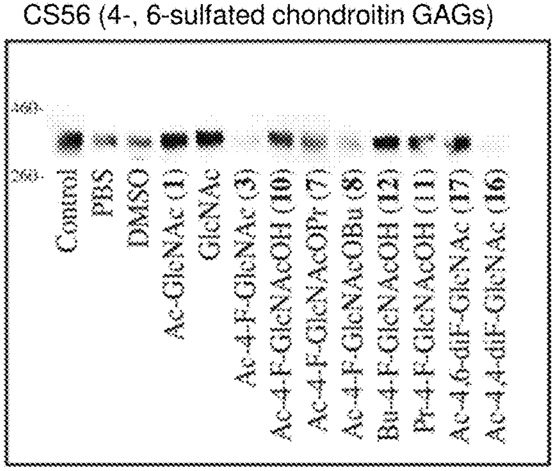
Figure 14D:
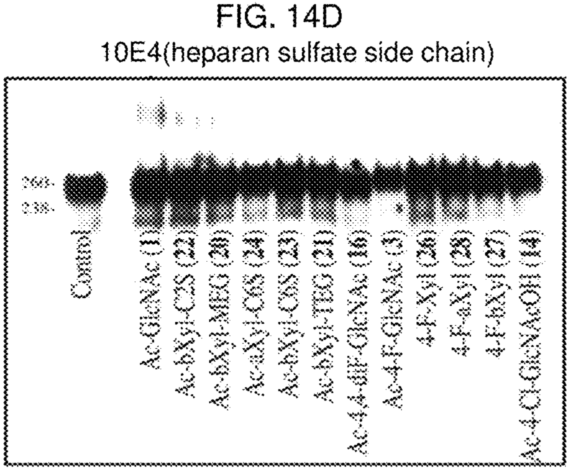
Figure 14E:
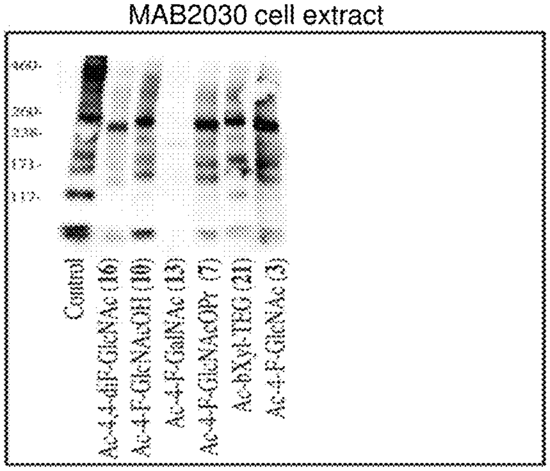

While the above determinations were of the conditioned media of treated astrocytes, we also harvested cell lysates from astrocytes treated with the more potent compounds that reduced secretory CSPG levels. Indeed, after 24 hours of treatment, the amount of MAB2030-immunoreactive material in the cell lysates was prominently lowered by the compounds tested (FIG. 14E). Thus, the reduction of CSPGs in the conditioned media noted earlier (FIG. 4) was also found in the astrocyte cell lysate.

Table 1 compares the compounds tested, and lists their ability to enhance OPC outgrowth on an inhibitory astrocyte matrix, and reduce T cell proliferation, with the top 6 most effective fluorinated compounds at reducing CSPG production being Ac-4,4-diF-GlcNAc 16, Ac-4-F-GlcNAcOH 10, Ac-4-F-GalNAc 13, Ac-4-F-GlcNAcOPr 7, Ac-4-F-GlcNAc 3, Ac-4-F-GlcNAcOBu 8. Xylosides were comparatively inactive in the screens compared to the abilities of the fluorinated sugar analogs. Across the different tests, Ac-4,4-diF-GlcNAc 16 was the most efficacious.

Figure 4D:
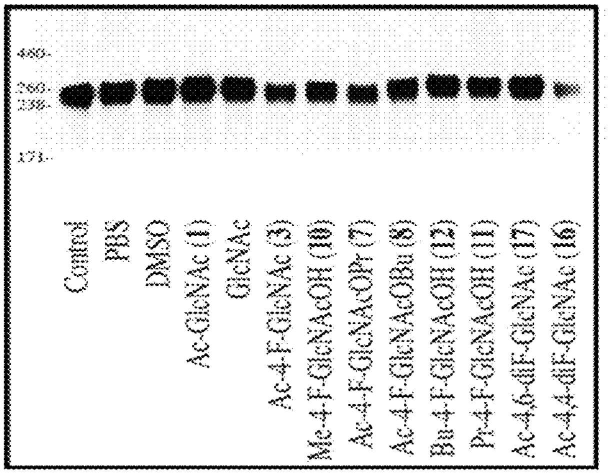
Figure 5B:
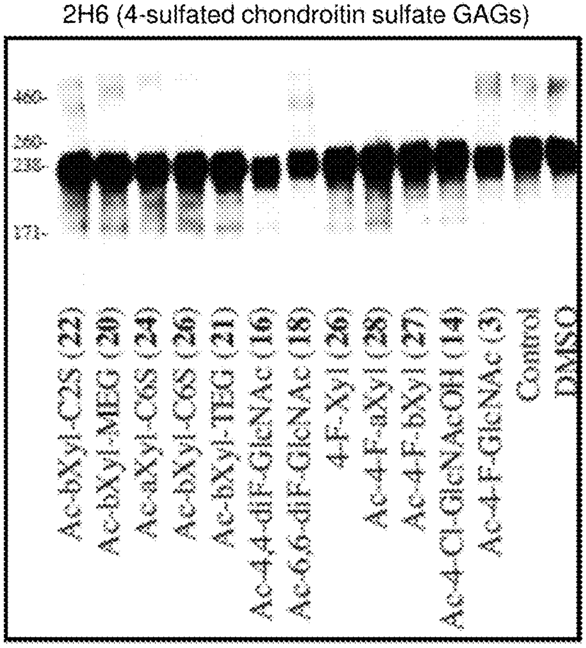

The 2H6 antibody to full length chondroitin sulfate GAGs proved a less sensitive marker (i.e., showed less qualitative changes) to sugar analogs; only compounds that were the most effective at reducing MAB2030 levels (i.e., compounds 3 (Ac-4-F-GlcNAc), 10 (Ac-4-F-GlcNAcOH), 16 (Ac-4,4-diF-GlcNAc), 7 (Ac-4-F-GlcNAcOPr)) showed evidence of reducing total chondroitin sulfate side chains (2H6) (FIG. 4*d*, FIG. 5*b*).

Compounds that had substitutions with multiple bulky groups (e.g., O3,O6-dibutanoate on compound 12 (Bu-4-F-GlcNAcOH) or lacked removable O-acyl protecting groups (e. g., O4,O6-dimethylated compound 5, O3-methylated compound 6) did not affect CSPG synthesis. The presence of multiple large ester protecting groups adds excessive lipophilicity of the molecule; this may slow down the diffusion of the compound from cell membrane, impairing the ability of compounds to enter cells or slowing down the hydrolysis by esterases. The presence of non-hydrolyzable O-methyl group(s) may result in the formation of UDP-sugar derivatives unfit for the binding site of 4-epimerase because of their O-methylations, and thus the compounds are unable to act as an inhibitor of the enzymes.

Xylosides in general were not as effective at reducing CSPG production as glucosamine analogs. Only the tetraethylene glycol 21 (Ac-bXyl-TEG) was effective at reducing CSPGs (FIG. 4*e*, FIG. 5*a*). CSPG production was not impacted by the benzylated β-D-xyloside 19 and peracetylated analogs that have a substitution at C-1 with different water-solubility-enhancing groups, such as the ethylene glycol 20 (Ac-bXyl-MEG), as well as the anionic 2-sulfoethyl derivative 22 (Ac-bXyl-C2S), and the related β-D-xyloside analog 23 (Ac-bXyl-C6S) with a 6-sulfohexyl group. Interestingly the per-O-acetylated 4-fluorinated xylosides 27 (Ac-4-F-aXyl) and 28 (Ac-4-F-bXyl) did not reduce CSPG production. While the tetraethylene glycol derivative of β-D-xyloside 21 (Ac-bXyl-TEG) was not fluorinated, it still interfered with CSPG production by astrocytes; it may act as an alternate sugar acceptor, diverting CSPG synthesis from the core protein to the soluble xyloside analog. Results suggest that the β-anomeric configuration of β-D-xylosides is required for subsequent GAG chains elongation by enzymes, as the analogous α-D-xyloside 24 (Ac-aXyl-C6S) did not act as an inhibitor.

Figure 5C:
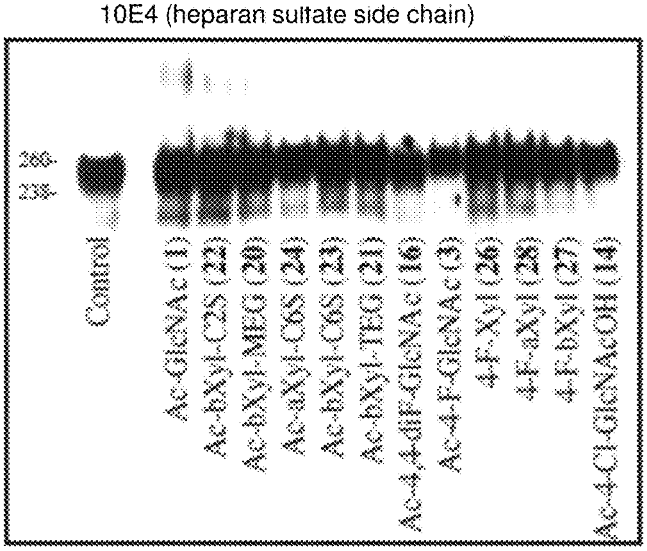

Compounds that were able to reduce chondroitin GAGs were also investigated for their ability to reduce heparan sulfate GAGs. Similar to CSPGs, heparan sulfate proteoglycans (HSPGs) are upregulated in MS lesions [van Horssen, J., Bö, L., Dijkstra, C. D. & de Vries, H. E. Extensive extracellular matrix depositions in active multiple sclerosis lesions. Neurobiology of disease 24, 484-491 (2006); van Horssen, J., Bö, L., Vos, C. M., Virtanen, I. & de Vries, H. E. Basement membrane proteins in multiple sclerosis-associated inflammatory cuffs: potential role in influx and transport of leukocytes. Journal of neuropathology and experimental neurology 64, 722-729 (2005)] and have detrimental pro-inflammatory capabilities [Parish, C. R. The role of heparan sulphate in inflammation. Nature reviews. Immunology 6, 633-643 (2006)]. It was observed that the compounds that most significantly reduced chondroitin sulfate GAGs were also capable of reducing HSPG side chains, detected by an antibody to intact heparan sulfate GAGs (FIG. 5*c*). There was a slight reduction in HSPG side chains by 4-fluorinated Ac-GlcNAc derivatives such as fluorosamine 3 and its analog with an anomeric O1-butanoate 8 (Ac-4-F-GlcNAcOBu), the 4,4-difluorinated 16 (Ac-4,4-diF-GlcNAc) and surprisingly, the O3,O6-dibutanoate 12 (Bu-4-F-GlcNAcOH). We observed that both Ac-4-F-GlcNAc 3 and Ac-4,4-diF-GlcNAc 16 also reduced HSPG side chains, albeit minimally, as detected by an antibody to intact heparan sulfate GAGs (FIG. 14D).

Overcoming CSPG Inhibition of OPCs

The process of remyelination requires oligodendrocyte lineage cells to undergo process outgrowth prior to their expression of mature myelin proteins for repair. Thus, process outgrowth in culture by cells of the oligodendrocyte lineage has been used as one surrogate for myelinating potential in vivo [Keough, M. B.; Rogers, J. A.; Zhang, P.; Jensen, S. K.; Stephenson, E. L.; Chen, T.; Hurlbert, M. G.; Lau, L. W.; Rawji, K. S.; Plemel, J. R. et al. An inhibitor of chondroitin sulfate proteoglycan synthesis promotes central nervous system remyelination. *Nat. Commun.* 2016, 7, 11312], since an oligodendrocyte needs to elaborate multiple protrusions emanating in several directions to contact many axons, and where these processes then compact around axons to form myelin segments. The presence of CSPGs in culture impairs the process outgrowth of OPCs, and this has been linked to reduced remyelination capacity in vivo [Keough, M. B.; Rogers, J. A.; Zhang, P.; Jensen, S. K.; Stephenson, E. L.; Chen, T.; Hurlbert, M. G.; Lau, L. W.; Rawji, K. S.; Plemel, J. R. et al. An inhibitor of chondroitin sulfate proteoglycan synthesis promotes central nervous system remyelination. *Nat. Commun.* 2016, 7, 11312]. It was reported previously that astrocytes in culture produce a plate-bound matrix abundant in CSPGs, that is left behind once astrocytes are removed from the plate, and this CSPG-containing matrix inhibits the outgrowth of plated OPCs [Keough, M. B. et al. An inhibitor of chondroitin sulfate proteoglycan synthesis promotes central nervous system remyelination. *Nature communications* 7, 11312 (2016)] (FIG. 7*a*). Thus, astrocytes were treated with test compounds for 48 hours and they were then removed from the cell culture plate leaving only their secreted ECM behind (FIG. 7*a*). When OPCs were plated on the astrocyte matrix, the extent of their process outgrowth over 2 days of observation was inhibited (FIG. 7*b*). Focusing on selected compounds because of the technical challenges imposed by this screen, it was found that the treatment with fluorinated compounds exerted a partial rescue of OPC outgrowth on astrocyte ECM. OPCs growing in the absence of astrocyte ECM can reach a mean outgrowth around 300 μm (FIG. 7*b,c*). Addition of CSPGs in the absence of astrocyte ECM exerted a similar inhibitory effect on OPC outgrowth as when they were cultured on astrocyte ECM (FIG. 7*b,c*) It was noted that the majority of fluorinated compounds that significantly reduced CSPG production in astrocytes (FIG. 4) were effective at improving mean outgrowth of OPCs onto the astrocyte ECM substrate (FIG. 7*d*). These compounds were: Ac-4,4-diF-GlcNAc 16 (Ac-4,4-diF-GlcNAc), fluorosamine 3 and its O1-deacetylated analog 10 (Ac-4-F-GlcNAcOH), anomeric O-propanoate 7, anomeric O-butanoate 8 (Ac-4-F-GlcNAcOBu), and the 4-fluorinated GalNAc derivative 13 (Ac-4-F-GalNAc) (FIG. 7*c*). Compounds that significantly enhanced OPC outgrowth but did not decrease CSPG production in astrocytes were 6,6-difluorinated compound 18 (Ac-6,6-diF-GlcNAc) and hexylsulfonate of xyloside 23 (Ac-bXyl-C6S).

Sugar Analogs Reduce Proliferation of Splenocytes

Figure 8A:
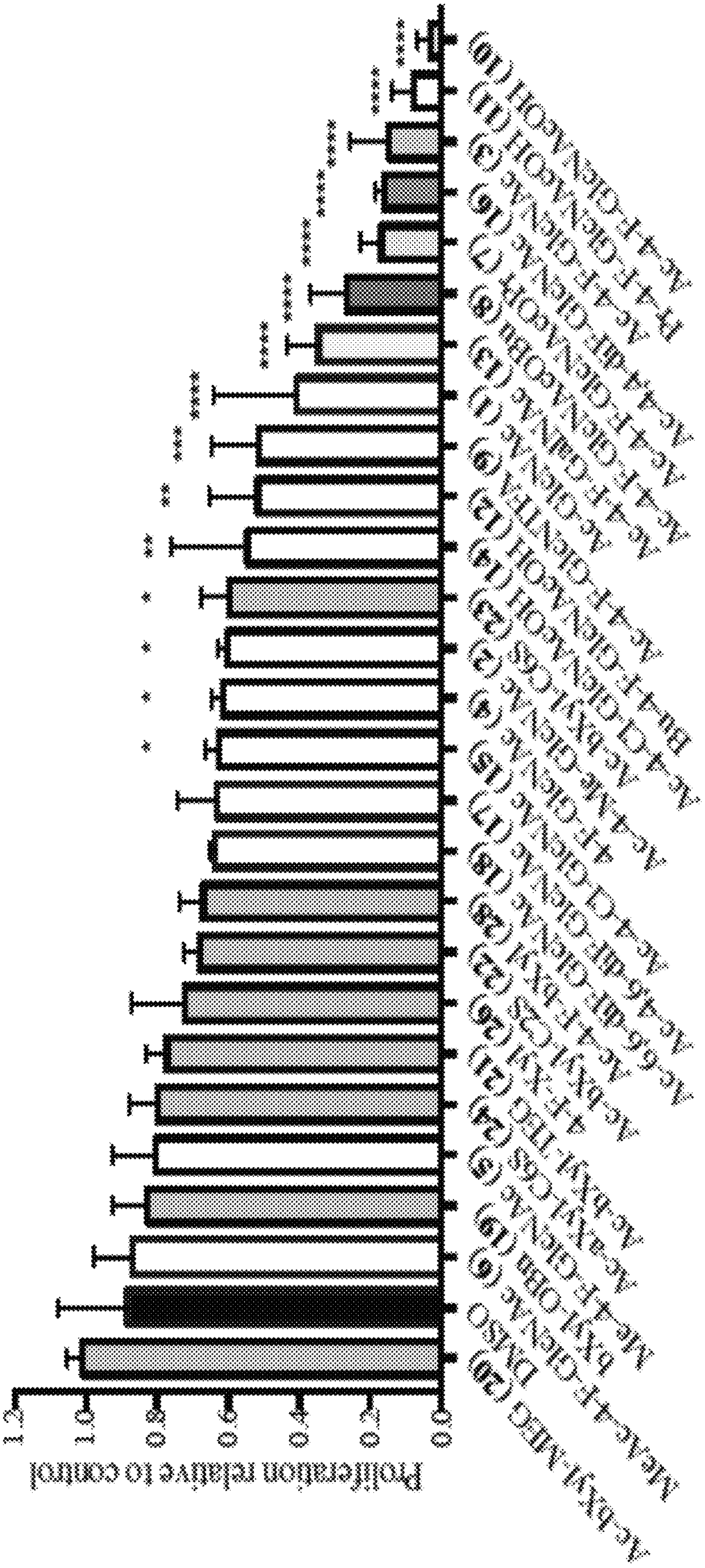
FIG. 8 depicts results that sugar analogs reduce the proliferation of splenocytes in culture. a, Proliferation of splenocytes activated with anti-CD3 and anti-CD28 antibodies and treated with 25 μM glucosamine analogs show the capacity of certain compounds to significantly reduce proliferation (counts per minute) in [3H]-thymidine incorporation assays. Data points of the graph represent the average of an independent experiment with four replicate wells and proliferation was normalized to control (untreated) activated splenocytes. Compounds were tested in at least three independent experiments. Propidium-iodide cell cycle analysis of b untreated activated splenocytes and c Ac-4,4-diF-GlcNAc 16-treated splenocytes showing that treated splenocytes are halted in the G1 phase, with reduced percentage in the synthesis phase. Levels of apoptotic cells are shown by the blue curve, cells in G1 by the red curve, cells in synthesis with the curve of diagonal lines, and cells in the G2/M phase by the second red curve. d, Propidium-iodide flow cytometry experiment showing that Ac-4-F-GlcNAc 10 and Ac-4,4-diF-GlcNAc 16 reduced the percentage of cells in the S (DNA synthesis)-phase of the cell cycle, with associated increase of cells in G1. e, Dose-response decrease in proliferation (counts per minute) of splenocytes treated with increasing concentrations of Ac-4-F-GlcNAc 3 and Ac-4,4-diF-GlcNAc 16 (25 μM) for 48 hours. f, Isolated CD3+ cells treated with Ac-4-F-GlcNAc 3 and 4,4-difluorinated analog 16 at 25 and 50 μM concentrations, and assessed for changes of early cell death (Annexin ANN+), necrosis (PI+), late cell death (ANN+PI+) and healthy (PI−ANN−). At these concentrations that reduced proliferation (e), both compounds had no evidence of causing non-specific cell apoptosis or necrosis. *$P<0.05$, $P<0.01$, **$P<0.0001$ one-way analysis of variance (ANOVA) with Dunnett's post hoc test.

It was assessed whether the glucosamine analogs have immunomodulatory properties on splenocytes isolated in culture. T cells within the splenocyte pool were polyclonally activated with anti-CD3 and anti-CD28 antibodies in the presence of compounds for 48 hours, and proliferation was determined by the uptake of tritiated thymidine and expressed as counts per minute. The relative change in proliferation of treated versus control splenocytes was taken in order to rank the compounds across multiple independent experiments (FIG. 8*a*). The compounds most effective at reducing proliferation by at least 50% include (best to least): 4-monofluorinated Ac-GlcNAc hemiacetals 10 (Ac-4-F-GlcNAcOH) and 11 (Pr-4-F-GlcNAcOH), 3 (Ac-4-F-GlcNAc), the 4,4-difluorinated compound 16 (Ac-4,4-diF-GlcNAc), the O1-propanoate 7 (Ac-4-F-GlcNAcOPr), O1-butanoate 8 (Ac-4-F-GlcNAcOBu), the 4-fluorinated GalNAc derivative 13 (Ac-4-F-GalNAc), and Ac-GlcNAc 1. The compounds that significantly reduced chondroitin sulfate GAG production in astrocytes were among the top 6 compounds that also reduced proliferation in splenocytes including Ac-4,4-diF-GlcNAc 16, the hemiacetal 10 (Ac-4-F-GlcNAcOH), the O1-propanaote 7 (Ac-4-F-GlcNAcOPr), Ac-4-F-GlcNAc 3, and O1-butanoate 8 (Ac-4-F-GlcNA-cOBu). Intriguingly, compounds that include the per-O-acetylated GlcNAc 1 (Ac-GlcNAc), the hemiacetals 11 (Pr-4-F-GlcNAcOH), 12 (Bu-4-F-GlcNAcOH) and N-trifluoroacetylated analog 9 (Ac-4-F-GlcNTFA), reduced splenocyte proliferation but did not lower CSPG production in astrocytes.

Figure 8B:
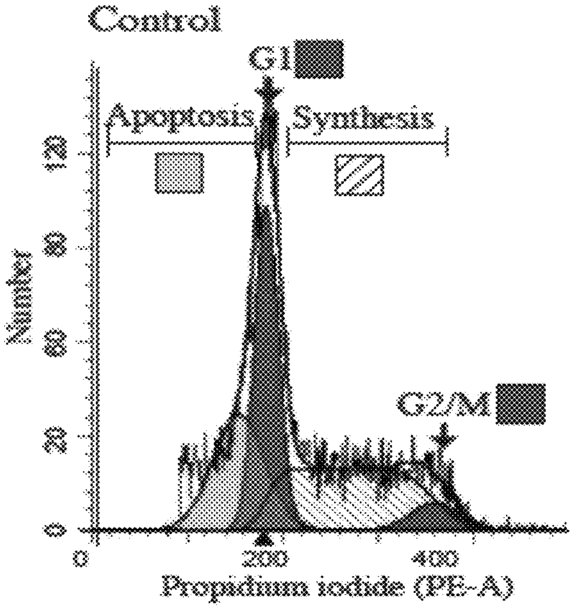
Figure 8C:
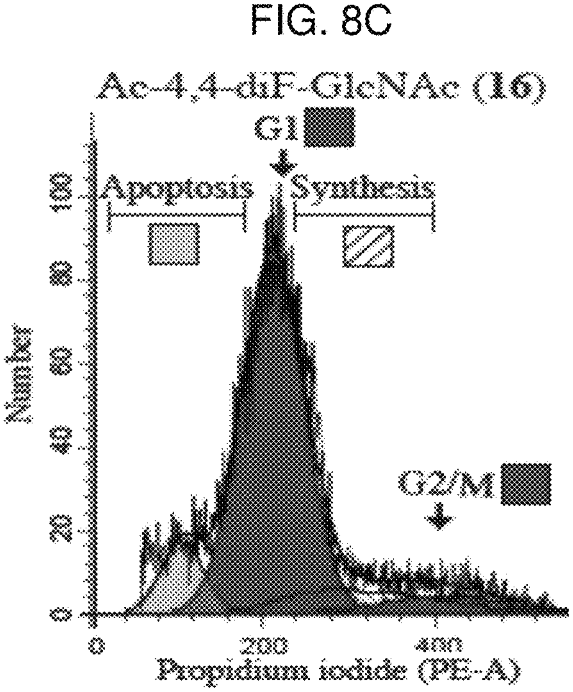
Figure 8D:
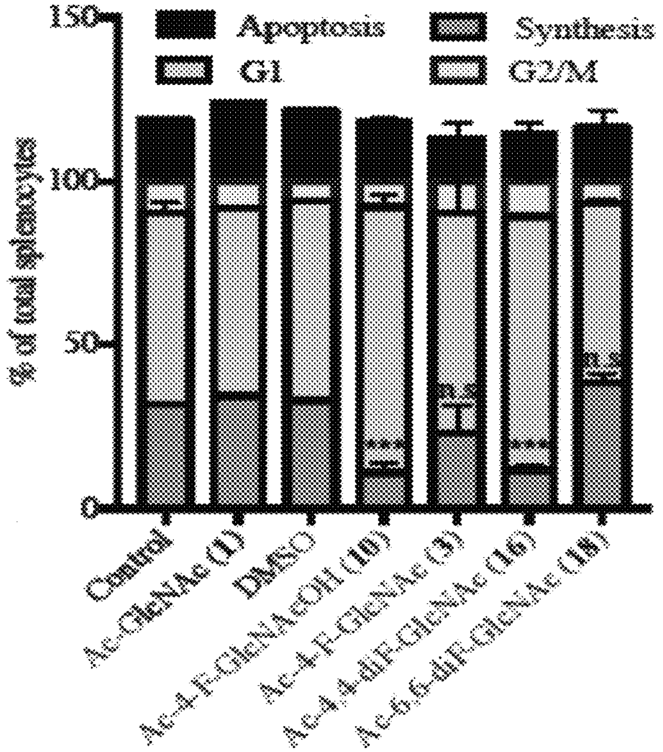
Figure 8E:
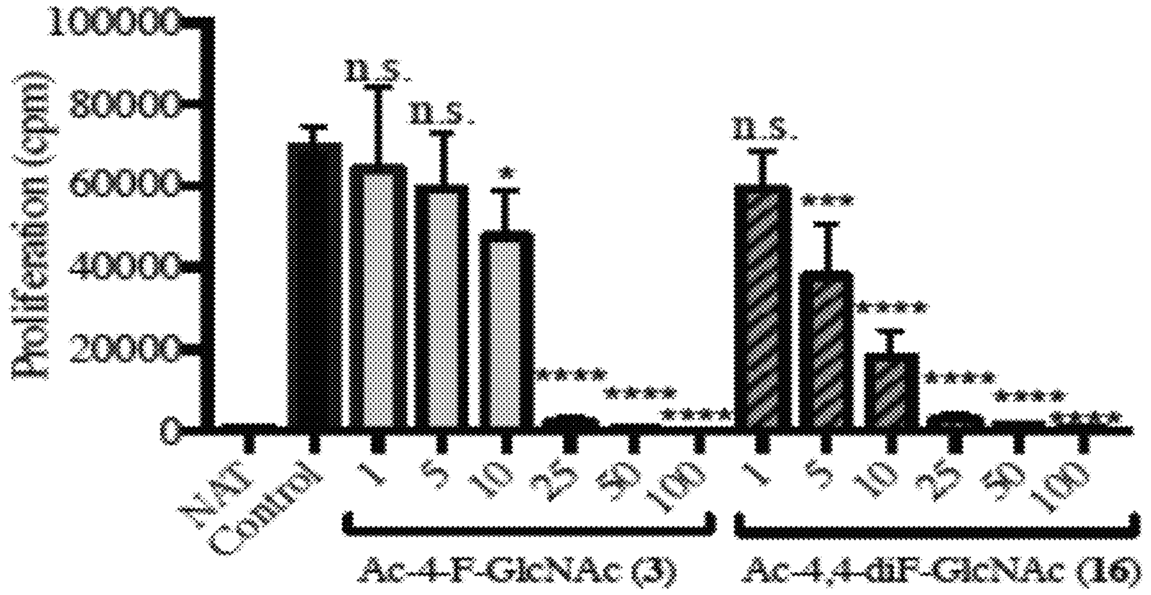
Figure 8F:
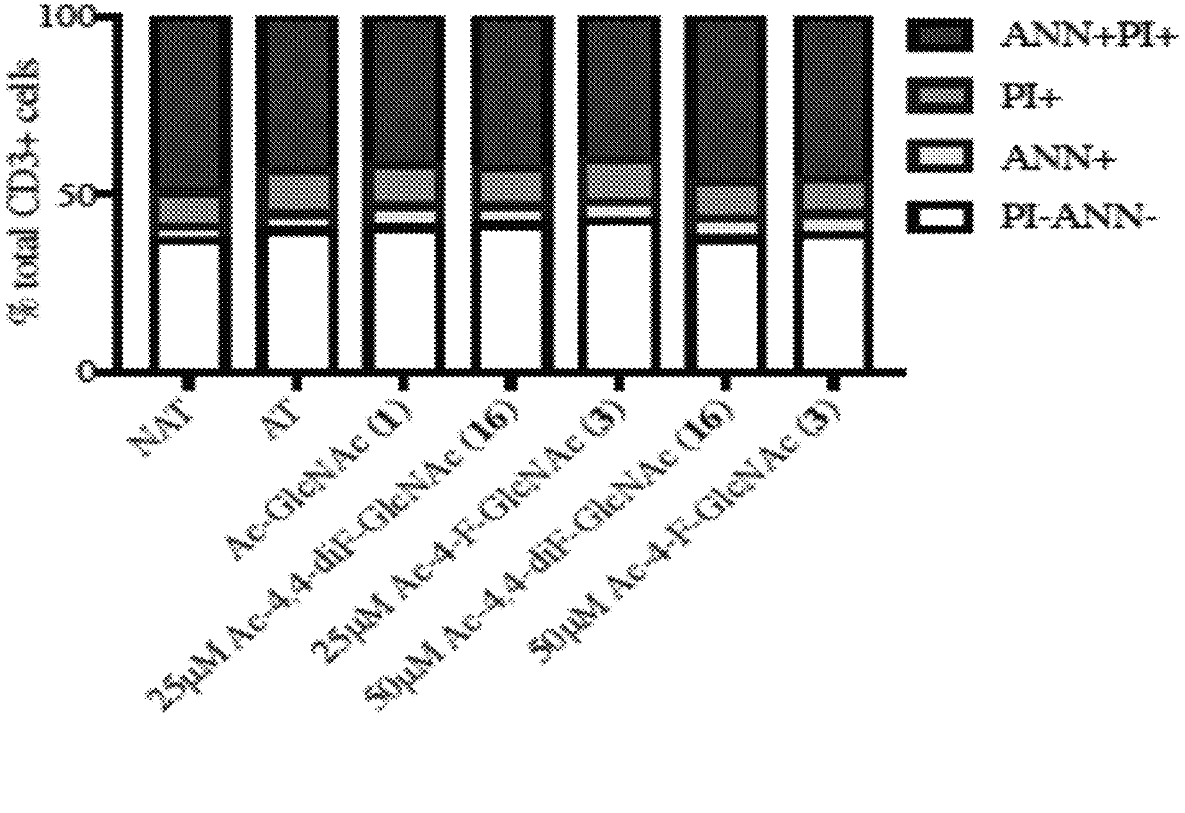

Cell-cycle flow cytometry with propidium iodide was used to corroborate the above results, and ensure the reduction in proliferation was not due to cell death. The analyses showed that there was an increase in cells halted in the G1 phase of the cell cycle, with a reduction in the percentage of cells in synthesis, and not due to an increase in apoptosis (FIG. 8*b-d*). Due to the efficacy of Ac-4,4-diF-GlcNAc 16 at both reducing CSPG production in astrocytes as well as splenocyte proliferation, the dose-response of Ac-4,4-diF-GlcNAc 16 and Ac-4-F-GlcNAc 3 to reduce proliferation in splenocytes was compared, and found that Ac-4,4-diF-GlcNAc 16 was more effective than Ac-4-F-GlcNAc 3 at lower concentrations (FIG. 8*e*). To further investigate whether the reduction of proliferation was due to cell death, Annexin V and propidium iodide staining were used to differentiate necrotic cells (propidium iodide+), apoptotic cells (annexin V+), dead cells (propidium iodide+ and annexin V+), and live cells (propidium iodide-annexin V−). Isolated CD3+ T cells were treated with two concentrations of Ac-4-F-GlcNAc 3 and Ac-4,4-diF-GlcNAc 16 (25 μM and 50 μM) and they did not display notable changes in their proportion of necrotic, apoptotic, dead, or live cells compared to activated control T cells; thus, these compounds reduce T cell proliferation without being non-specifically cytotoxic.

Testing Fluorinated Glucosamines on Macrophages

While lymphocytes are crucial to the pathogenesis of MS, myeloid cells, particularly macrophages also have key roles in the disease [Mishra, M. K. & Yong, V. W. Myeloid cells—targets of medication in multiple sclerosis. Nature reviews. Neurology 12, 539-551 (2016); Reich, D. S., Lucchinetti, C. F. & Calabresi, P. A. Multiple Sclerosis. New England Journal of Medicine 378, 169-180 (2018); Baecher-Allan, C., Kaskow, B. J. & Weiner, H. L.

Figure 9:
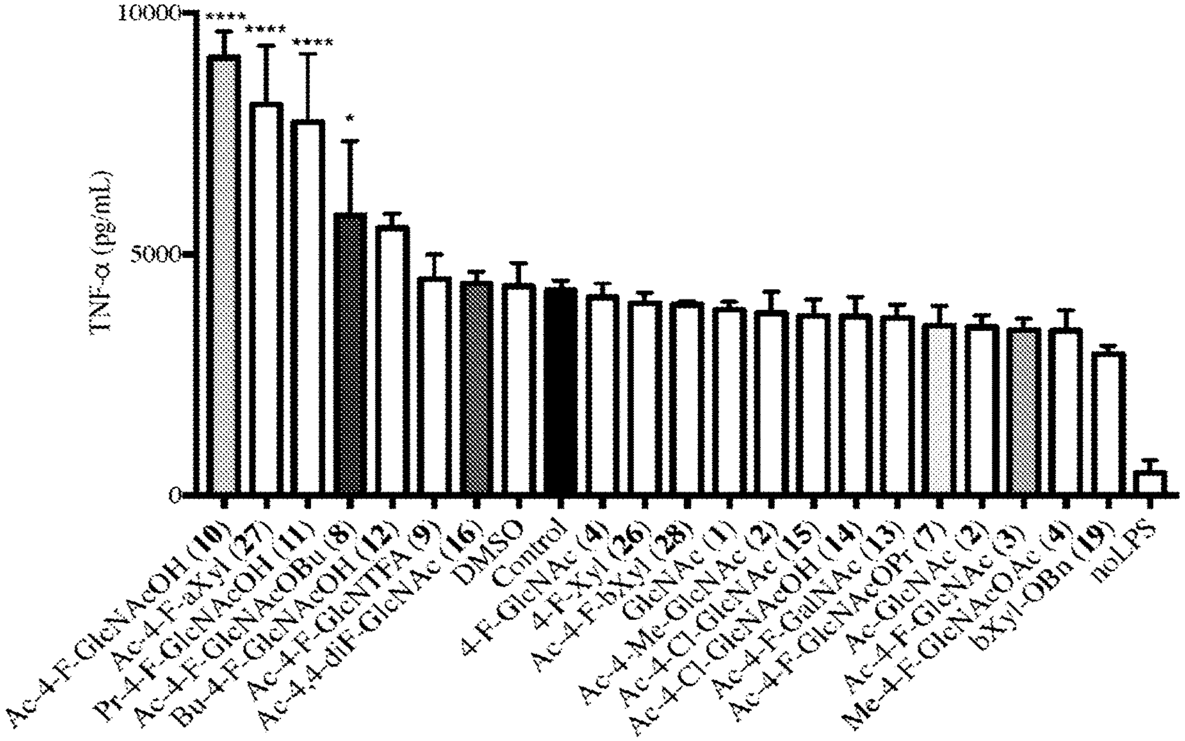
FIG. 9 depicts TNFα production in bone marrow-derived macrophages (BMDMs) treated with sugar analogs. BMDMs were stimulated with LPS and treated with 50 μM of sugar analogs for 24 hours *$P<0.001$, **$P<0.0001$ compared with astrocyte ECM control; one-way analysis of variance with Dunnett's post hoc test. Error bars are mean±s.d.

Multiple Sclerosis: Mechanisms and Immunotherapy. Neuron 97, 742-768 (2018)]. It was tested whether the sugar analogs could affect the activity of macrophages, using bone marrow-derived macrophages (BMDMs) stimulated with lipopolysaccharide (LPS, 100 ng/ml). The sugar analogs were added at 50 μM prior to LPS, and the conditioned medium was collected after 24 hours and assayed for levels of the secreted cytokine TNFα. In general, the compounds did not reduce TNFα production by LPS-stimulated macrophages. Three compounds tested, including the 4-mono-fluorinated hemiacetals 10 (Ac-4-F-GlcNAcOH) and 11 (Pr-4-F-GlcNAcOH) that respectively have O3,O6-diacetates, O3,O6-dipropanoates, and the fully acetylated α-xylopyranose 27 (Ac-4-F-aXyl), enhanced TNFα levels (FIG. 9). Ac-4-F-GlcNAc 3 and the 4,4-difluorinated compound 16 (Ac-4,4-diF-GlcNAc) did not alter cytokine level of activated macrophages.

Testing Toxicity of Sugar Analogs

Also studied were whether compounds were toxic. Compounds Ac-4,4-diF-GlcNAc 16, Ac-4-F-GlcNAcOH 10, Ac-4-F-GlcNAc 3, and Ac-4-F-GlcNAcOBu 8 did not show detectable cell death on splenocytes with propidium iodide/annexin V staining or cell cycle analysis (FIG. 8*d,f*).

Figure 6B:
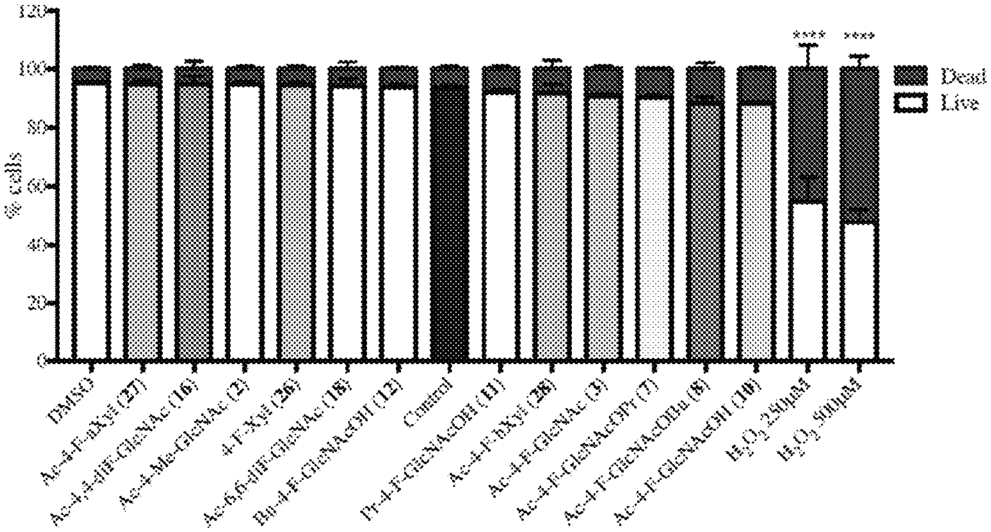

Toxicity on astrocytes was assayed with propidium iodide/calcein AM immunocytochemistry. Live cells convert calcein AM into a green fluorescent product, whereas dying/dead cells are stained with propidium iodide. At the high concentration of 100 μM the top 6 fluorinated compounds that significantly reduced chondroitin sulfate GAGs from astrocytes (Ac-4,4-diF-GlcNAc 16, Ac-4-F-GlcNA-cOH 10, Ac-4-F-GalNAc 13, Ac-4-F-GlcNAcOPr 7, Ac-4-F-GlcNAc 3, Ac-4-F-GlcNAcOBu 8) did not produce toxicity (FIG. 6*b*). As shown with representative staining, there was no morphological changes in treated astrocytes whereas the positive control of $H_2O_2$ caused increase in propidium iodide-positive staining (FIG. 6*a*).

Figure 6C:
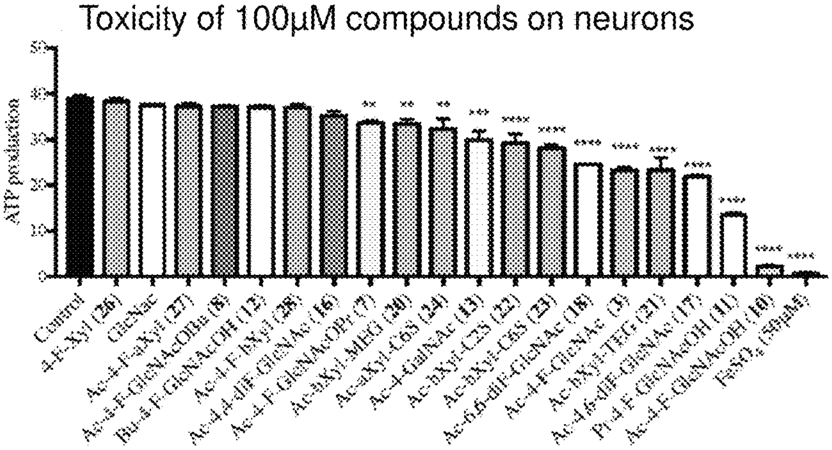
Figure 6D:
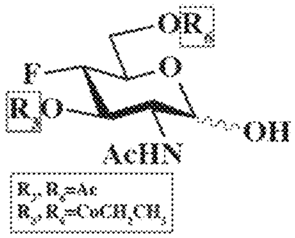

If the sugar compounds are to be used in neurological disorders, they should not display toxicity to neural cells. Thus, human neurons were used to test the compounds, and the ATP luminescence assay as a readout of metabolic stress and a surrogate of toxicity. Compounds were tested at a high dose of 100 μM. Neurons had a greater sensitivity to the toxic potential of sugar analogs than astrocytes (FIG. 6*c*). Two compounds that reduced ATP production by more than 50% were the 4-fluorinated hemiacetals that respectively bear O3,O6-diacetates 10 (Ac-4-F-GlcNAcOH) and O3,O6-dipropanoates 11 (Pr-4-F-GlcNAcOH), with the former displaying higher cytotoxicity than the latter (FIG. 6*d*). Interestingly, the homolog 12 (Bu-4-F-GlcNAcOH) bearing slightly longer O3,O6-dibutanoates showed no cytotoxicity.

Ac-4,4-diF-GlcNAc 16 Novel Sugar Analog Reduces EAE Disease Activity

The in vitro screens highlight the novel compound 16 (Ac-4,4-diF-GlcNAc) as the most potent drug at reducing CSPG production by astrocytes. Ac-4,4-diF-GlcNAc 16 also maximized OPC outgrowth on an astrocyte inhibitory matrix (FIG. 4), had immunomodulatory properties on splenocytes (FIG. 8) and showed no obvious toxicity (FIG. 6). Thus, it was investigated whether these in vitro results translate to a beneficial effect of Ac-4,4-diF-GlcNAc 16 in ameliorating the severity of EAE.

Figure 10A:
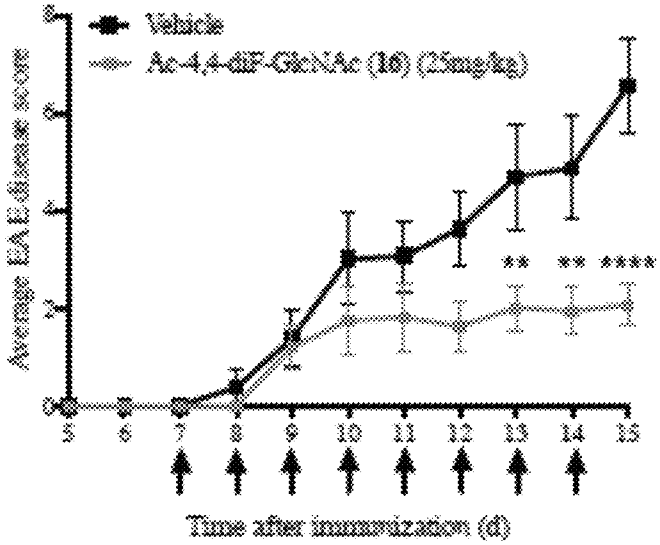
FIG. 10 depicts that Ac-4,4-diF-GlcNAc 16 attenuates EAE. a, Average daily EAE clinical score of mice treated with 25 mg/kg Ac-4,4-diF-GlcNAc 16 or saline vehicle (N=8) with daily intraperitoneal treatment shown by arrows; mice were then killed for the analyses of panels c to g. b, Sum of scores displaying individual burden of disease. c, Brightfield images of F4/80, CD45 and immunofluorescence of CD45 and Pan-laminin in vehicle- or Ac-4,4-diF-GlcNAc-treated mice (scale bar 50 μm). d, Flow cytometry of the spinal cord showing reduction in both % CD3+ T cells and % CD45HiCD11b+ monocytes/macrophages (and median fluorescence intensity) following Ac-4,4-diF-GlcNAc 16 treatment. e, Average perivascular cuffs per spinal cord in treated and vehicle-treated EAE mice (N=5 or 6 mice). f, Perivascular cuffs identified with CD45 and pan-laminin staining next to Imaris-processed perivascular cuff (red, laminin) with CD45+ cells (green) rendered as a surface (bar=50 μm). g, Number of CD45+ cells within 100 μm of perivascular cuffs, quantified by Imaris. h, Average daily EAE clinical score of mice treated with 25 mg/kg Ac-4,4-diF-GlcNAc or vehicle from peak clinical severity (day 15, N=8). i, Average daily EAE clinical score of EAE mice treated with 50 mg/kg Ac-4,4-diF-GlcNAc 16, 50 mg/kg Ac-4-F-GlcNAc 3, or vehicle from pre-onset (day 7, N=10); arrows indicate daily injections. *$P<0.05$, $P<0.01$, **$P<0.0001$. EAE scores (a,h,i) were analyzed by two-way repeated-measures ANOVA with Sidak's post-hoc test versus vehicle; mean±s.e.m. b,d,e,g were analyzed by two-tailed unpaired t-test, mean+s.d.
Figure 10B:
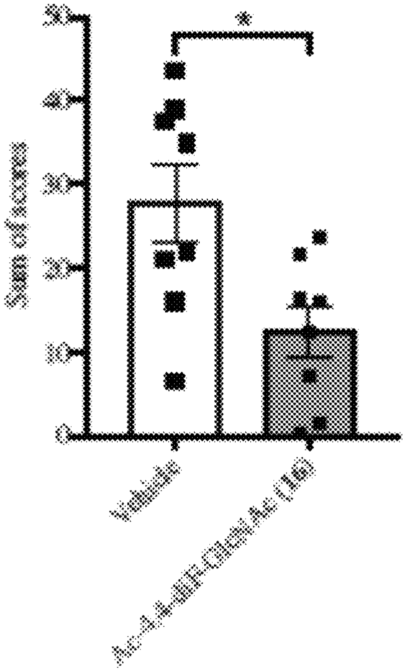

EAE mice were exposed to two dose regimens of Ac-4,4-diF-GlcNAc 16, whereby the drug was initiated prior to the onset of clinical signs, or from peak clinical severity. EAE was induced in mice by myelin oligodendrocyte glycoprotein peptide and associated adjuvants. In the first regimen, treatment began on day 7, a timepoint just before mice are expected to show clinical signs ('pre-onset') but where immune cells are becoming activated and infiltrating into the CNS. Ac-4,4-diF-GlcNAc 16 (25 $mgkg^{-1}$) or saline vehicle was given intraperitoneally daily until the mice reached peak clinical severity at day 15. Mice treated prophylactically with Ac-4,4-diF-GlcNAc 16 had significantly lower EAE clinical scores than the control group (FIG. 10*a*). The sum of scores (burden of disease), which represents the sum of the daily clinical scores per mouse, was also significantly reduced with Ac-4,4-diF-GlcNAc 16 treatment (FIG. 10*b*).

Figure 10C:
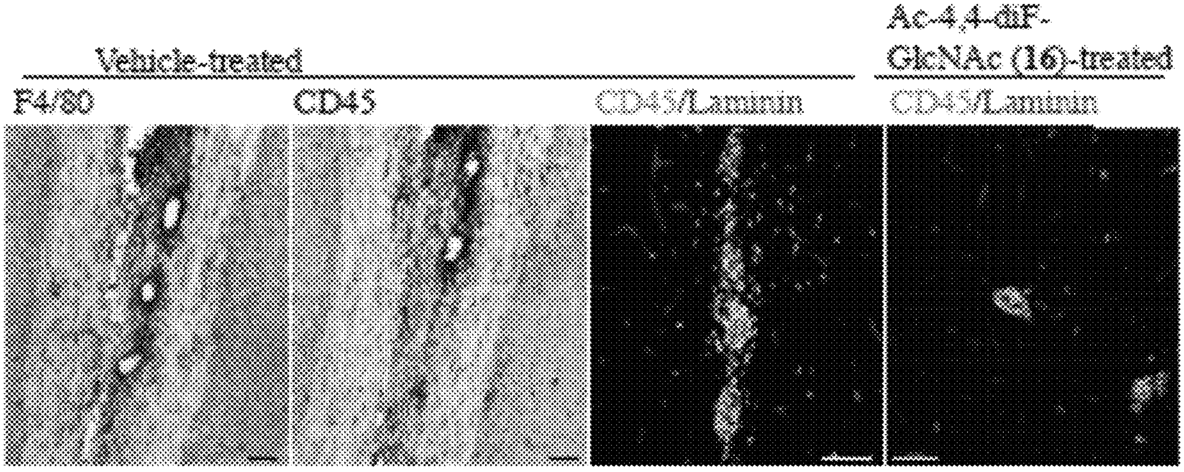
Figure 10D:
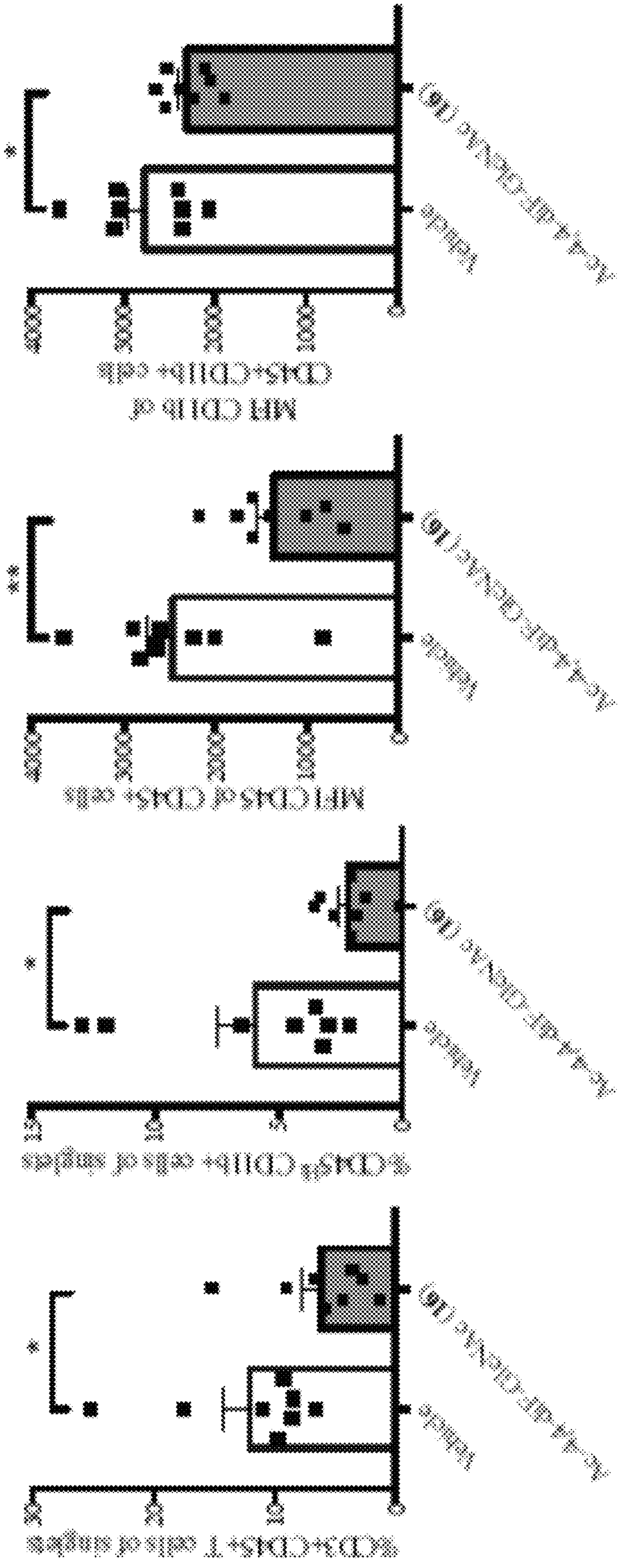
Figure 10E:
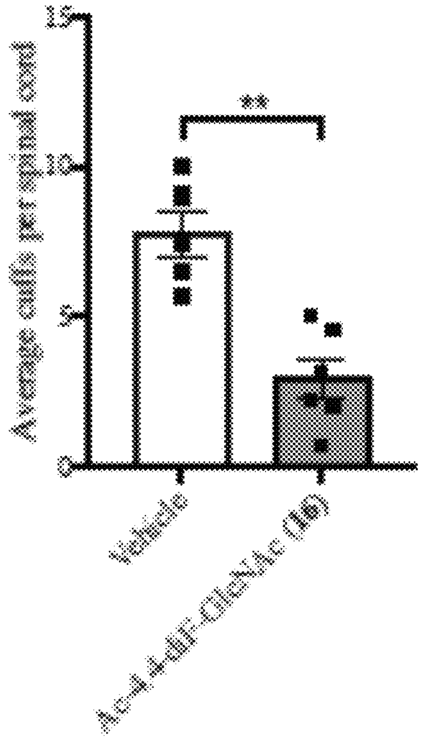
Figure 11A:
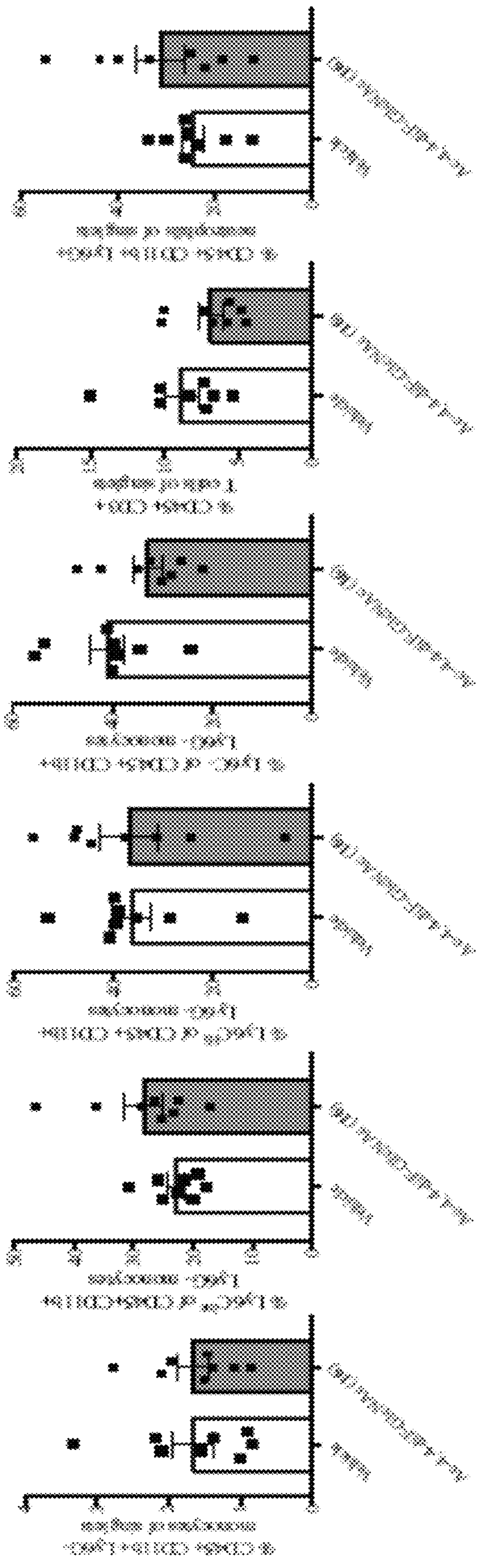
FIG. 11 depicts a, Flow cytometry from blood at peak EAE that found no significant difference between Ac-4,4-diF-GlcNAc 16 and vehicle of % Ly6CHi, Ly6CInt, Ly6CLo or total Ly6C+ monocytes. There was also no significant difference in circulating neutrophils (Ly6G+ CD11b+ CD45+) or T cells (CD45+ CD3+). b,c, Correlation between the average cuffs per spinal cord per mouse and EAE disease score (b), and EAE sum of scores (c). Linear regression analysis found that the slope was significantly non-zero for the relationship between average cuffs and EAE disease score (R2=0.5439, p value=0.0011) and EAE sum of scores (R2=0.5074, p=0.0020) but there was no significant difference between the slopes of treated and vehicle-treated mice. Each spot represents the average cuffs per spinal cord per mouse. Red spots are mice with EAE that were treated with Ac-4,4-diF-GlcNAc 16 (day 7 to day 15; N=6 mice), and black spots represent vehicle EAE mice (N=10). d, Imaris-quantified CD45+ cells within perivascular cuffs (0 μM), 0-5 μm, 5-10 μm, 10-20 μm, 20-30 μm, 30-40 μm, 40-50 μm, and 50-100 μm in vehicle and Ac-4,4-diF-GlcNAc-treated mice. A two-way repeated measures ANOVA with Sidak's multiple comparison test found an overall significant difference between the vehicle and Ac-4,4-diF-GlcNAc 16 distances (*, $p<0.05$), and a significant difference between the number of CD45+ cells vehicle and Ac-4,4-diF-GlcNAc 16 at 50-100 μm (***, $p<0.001$).
Figure 12A:
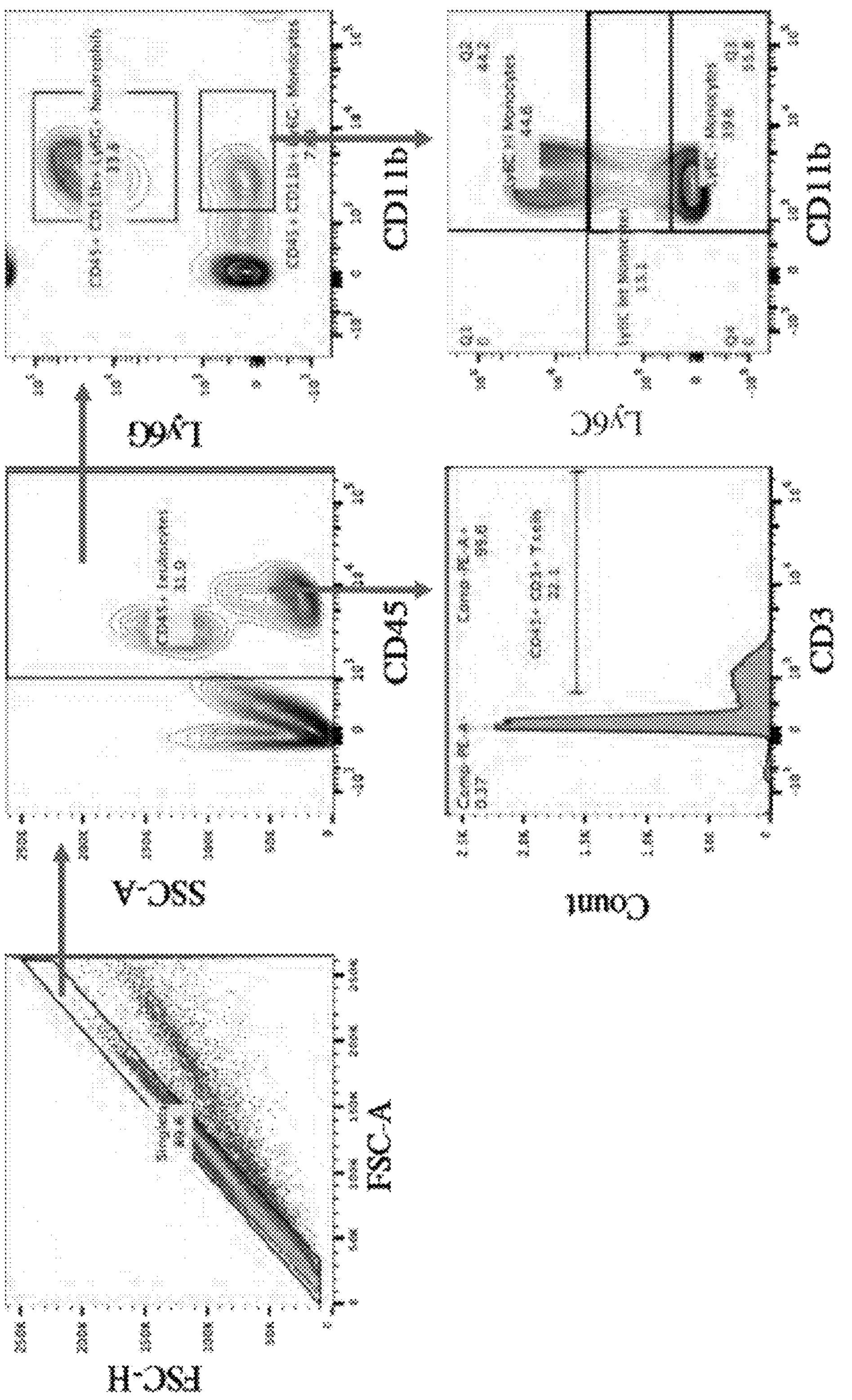
FIG. 12 depicts a flow cytometry gating strategy used for the EAE experiment where EAE mice were treated with vehicle or 25mgkg-1 Ac-4,4-diF-GlcNAc 16 from day 7 to day 15. a, Murine blood was isolated and stained for CD45, CD11b, CD3, Ly6C, and Ly6G and b, spinal cord was isolated and stained for CD45, CD11b, and CD3. For both methods, the forward scatter height and area was used to isolate singlets, after which CD45+ cells were separated. T cells were identified by CD45+ and CD3+ staining. From the CD45 gate, CD11b+ cells were isolated. For the blood, Ly6G gated neutrophils (CD45+ CD11b+ Ly6G+) were separated from other myeloid cells (CD45+ CD11b+ Ly6G−). Ly6C was used as a marker to differentiate subtypes of proinflammatory monocytes (Ly6CHi), anti-inflammatory monocytes (Ly6CLo) and other monocytes (Ly6CInt). For the spinal cord, CD11b+CD45+ cells were further separated into CD45Hi cells (which may represent monocyte-derived macrophages) and CD45Lo cells (which may represent microglia).
Figure 12B:
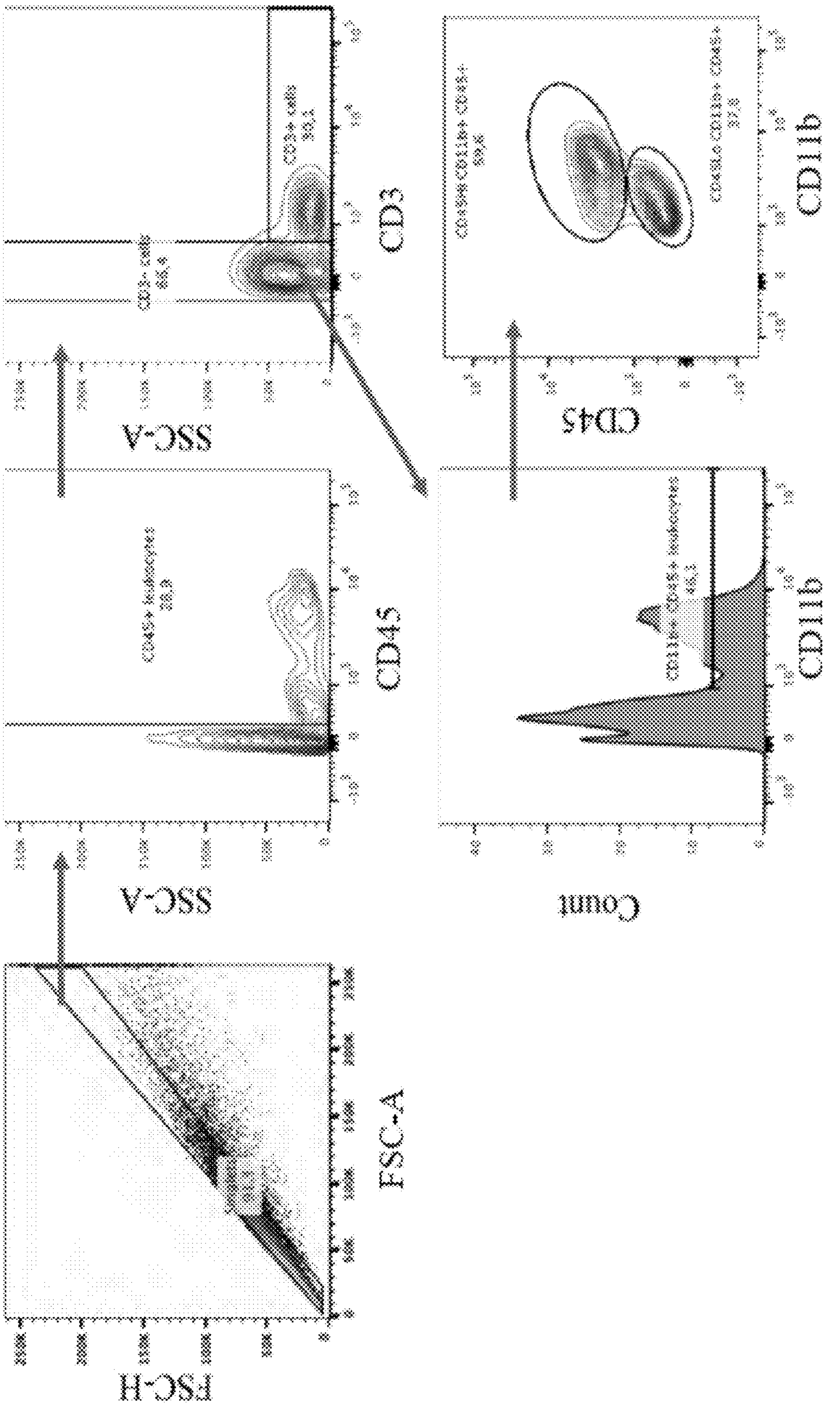

Notably, flow cytometry of the lumbar/thoracic spinal cord found treatment significantly decreased $CD45^{Hi}$CD11b+ infiltrating monocytes/macrophages, and significantly lowered CD45+ CD3+ T lymphocytes within the spinal cord (FIG. 10*d*). Ac-4,4-diF-GlcNAc 16 treatment also significantly reduced the median fluorescence intensity of CD11b of CD11b+CD45+ cells, and decreased the median fluorescence intensity of CD45 in CD11b+CD45+ cells (FIG. 10*d*). Flow cytometry of the blood did not show changes in monocyte or lymphocyte populations (FIG. 11*a*; see FIG. 12 for gating strategy).

Figure 11B:
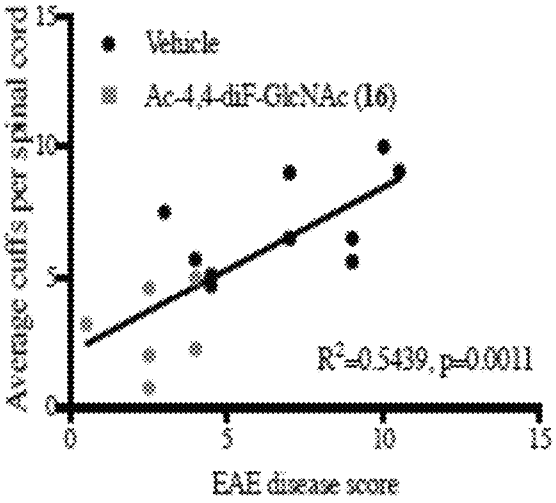
Figure 11C:
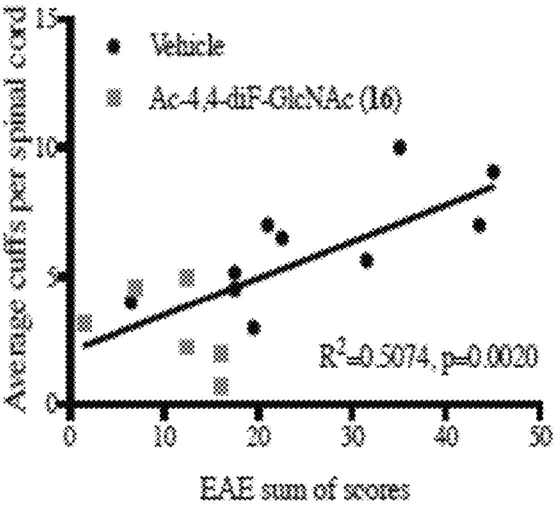
Figure 11D:
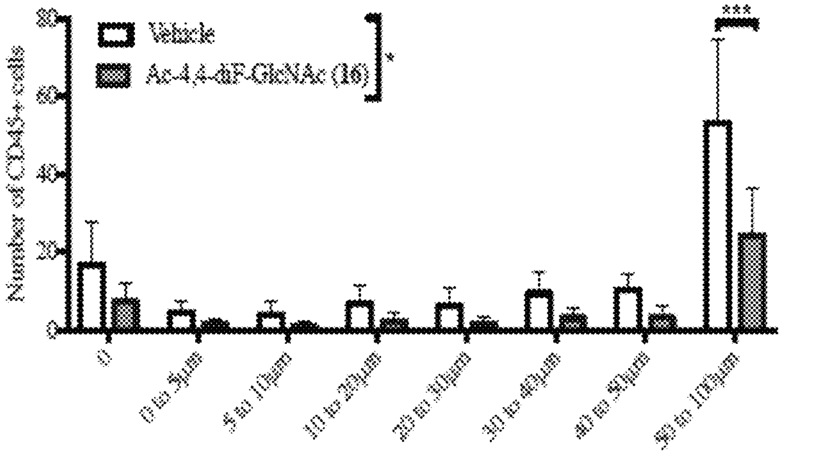
Figure 15A:
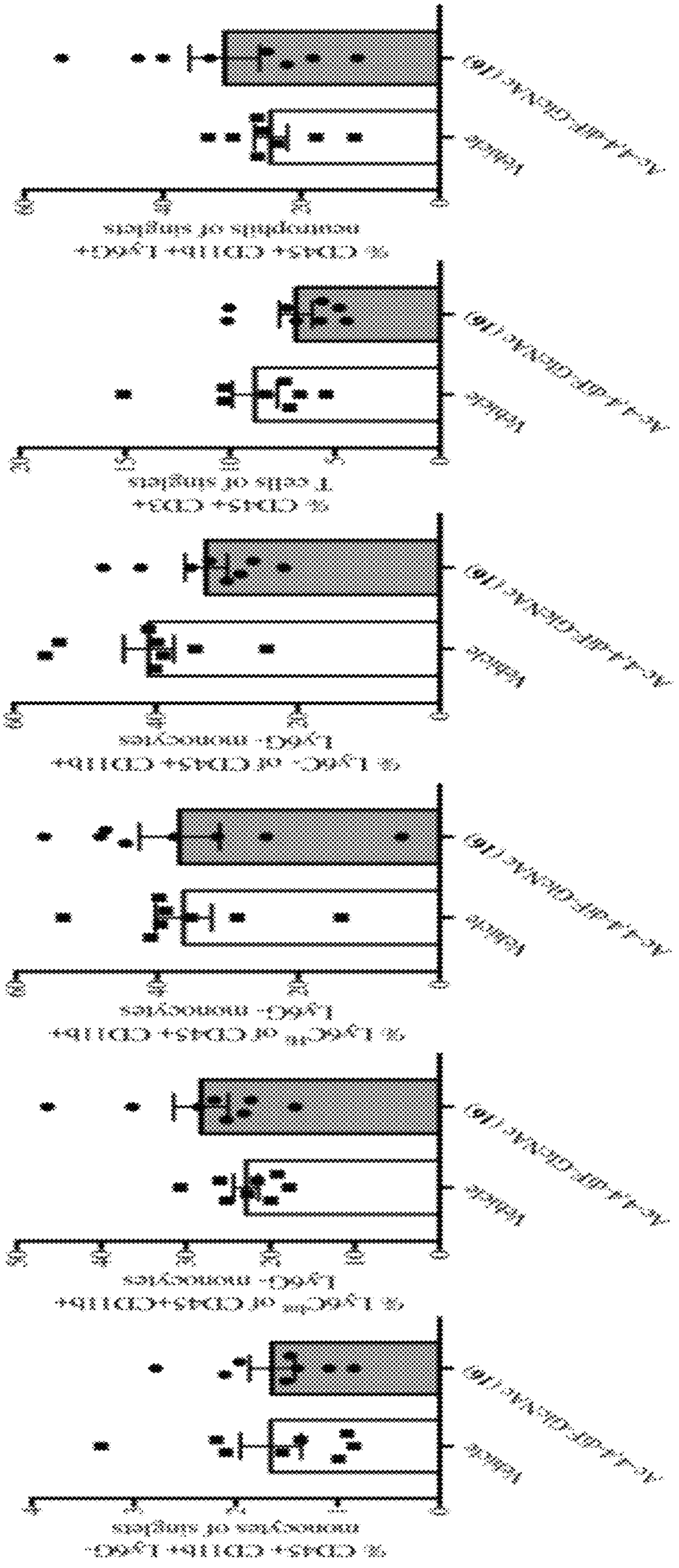
FIG. 15 depicts further analysis of mice treated daily with 25 mg/kg Ac-4,4-diF-GlcNAc 16 or saline vehicle (N=8, day 7 to 14). (A) Flow cytometry from blood at peak EAE with no significant difference between Ac-4,4-diF-GlcNAc 16 or vehicle of % $Ly6C^{Hi}$, $Ly6C^{Int}$, $Ly6C^{Lo}$, or total Ly6C+ monocytes, circulating neutrophils (Ly6G+ CD11b+ CD45+) or T cells (CD45+ CD3+). (B)(C) Correlation between the average cuffs per spinal cord per mouse and EAE disease score (B), and EAE sum of scores (C). Linear regression analysis with a non-zero slope for the relationship between average cuffs and EAE disease score and sum of scores for vehicle and Ac-4,4-diF-GlcNAc 16-treated mice. There was no significant difference between slopes of treated and vehicle-treated mice for either graph. Each point represents the average cuffs per spinal cord per mouse (red circle=Ac-4,4-diF-GlcNAc 16, black square=vehicle). (D)
Figure 15B:
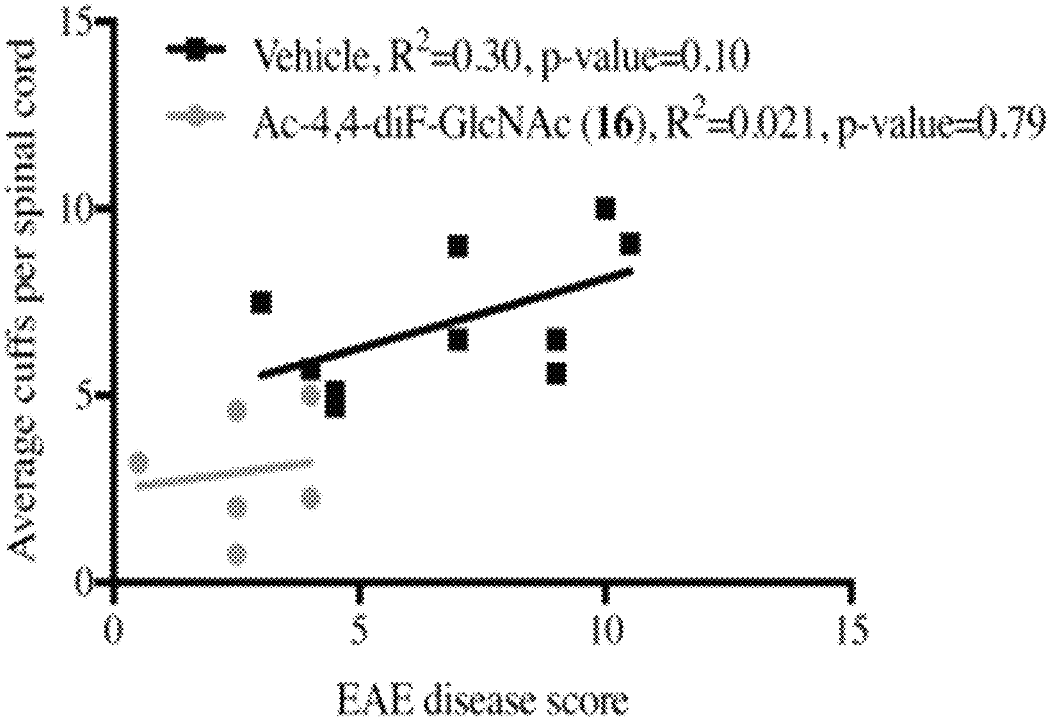
Figure 15C:
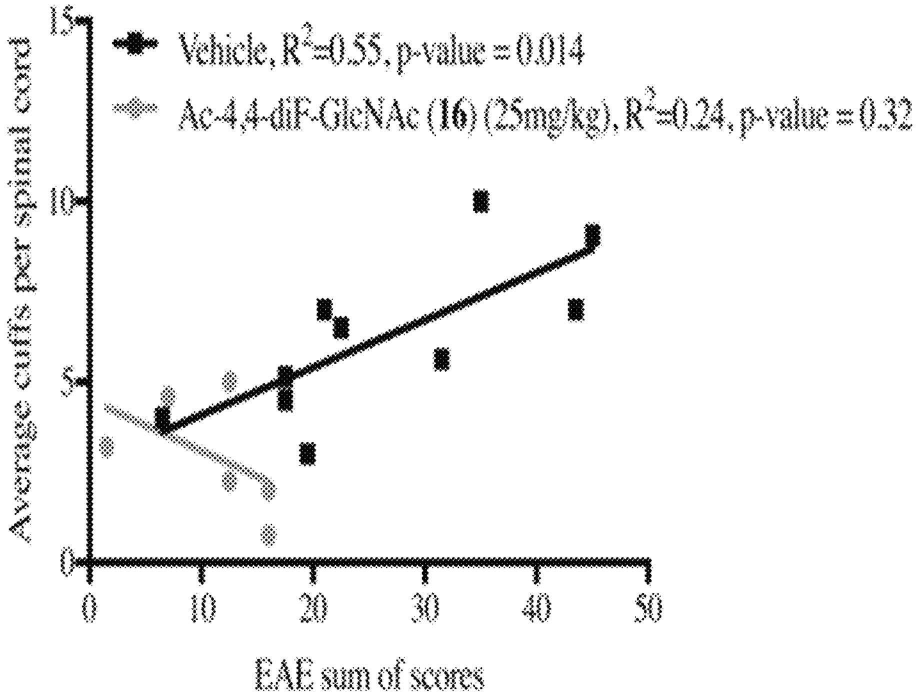
Figure 15D:
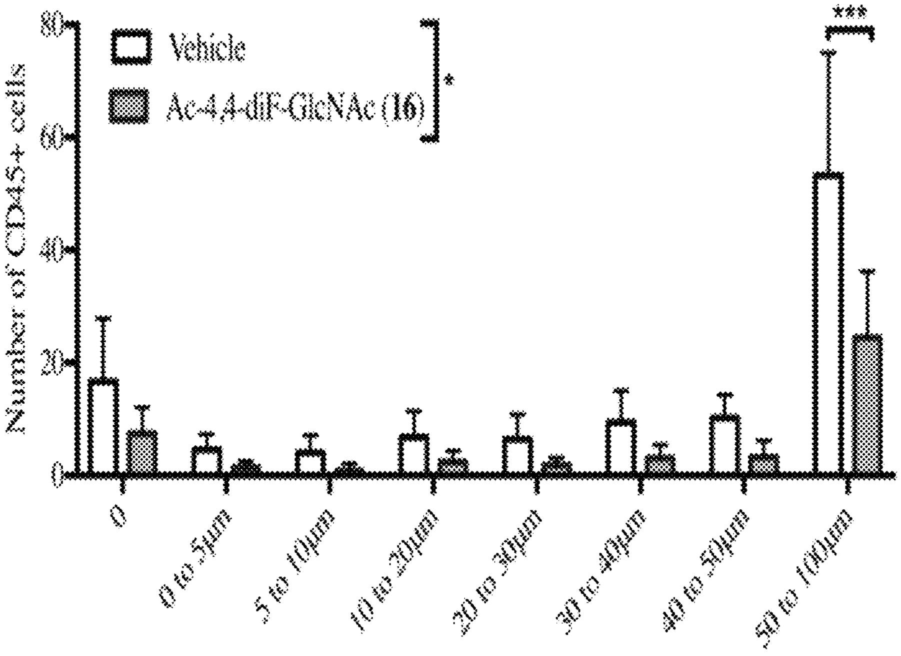
Figure 15E:
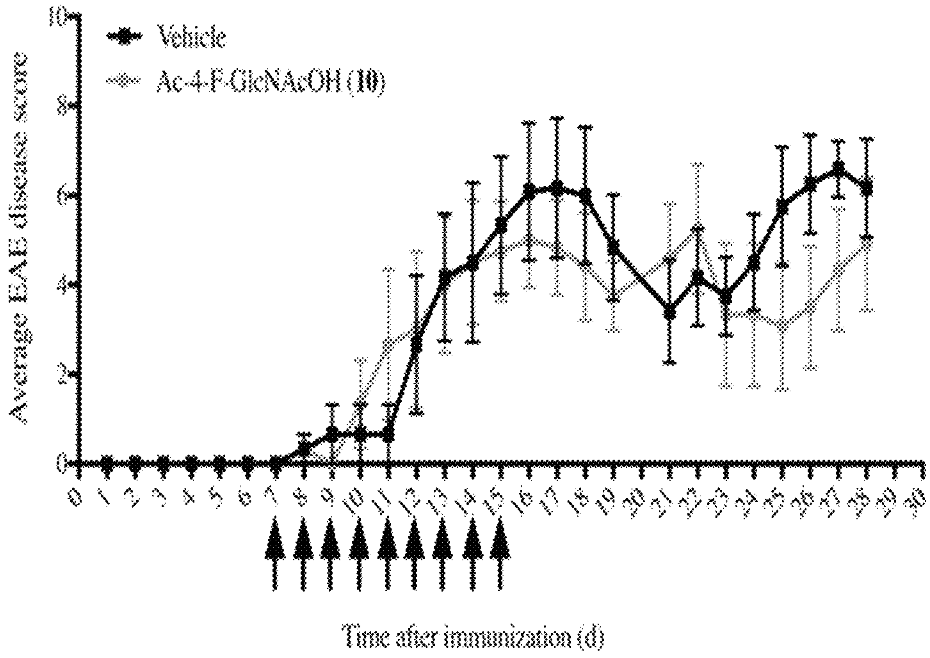

Routes of entry of immune cells into the CNS include subpial meningeal infiltration, passage across the fenestrated ependymal layer of the choroid plexus, and transmigration through the basement membranes of post-capillary venules [Sorokin, L. The impact of the extracellular matrix on inflammation. Nature reviews. Immunology 10, 712-723 (2010); Ransohoff, R. M. & Engelhardt, B. The anatomical and cellular basis of immune surveillance in the central nervous system. Nature reviews. Immunology 12, 623-635 (2012)]. Through this last route, an inflammatory perivascular cuff forms, and is detected as CD45+ cells accumulated within two laminin-positive basement membranes. EAE spinal cords had an abundance of perivascular cuffs, positive for CD45 cells (FIG. 10*c*). There was a significant correlation between EAE sum of scores or EAE disease score and the average number of spinal cord perivascular cuffs in EAE mice (FIG. 11*b,c*), suggesting that there is a relationship between EAE severity and number of perivascular cuffs in the spinal cord. There was a significantly reduced average number of perivascular cuffs in Ac-4,4-diF-GlcNAc 16-treated mice compared to vehicle (FIG. 10*c,e*). In contrast to the reduction in clinical score with Ac-4,4-diF-GlcNAc 16, treatment with Ac-4-F-GlcNAcOH 10, the most effective compound at reducing splenocyte proliferation in vitro, did not reduce EAE clinical score when mice were treated from day 7 to day 15 with 50 mg/kg intraperitoneal injections (FIG. 15E).

Figure 10G:
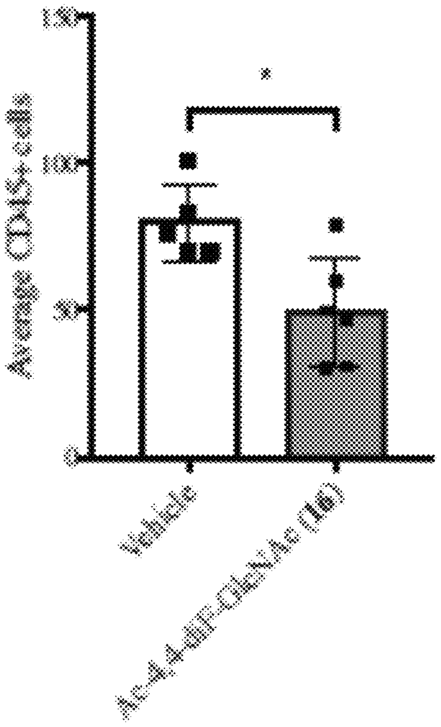
Figure 10F:
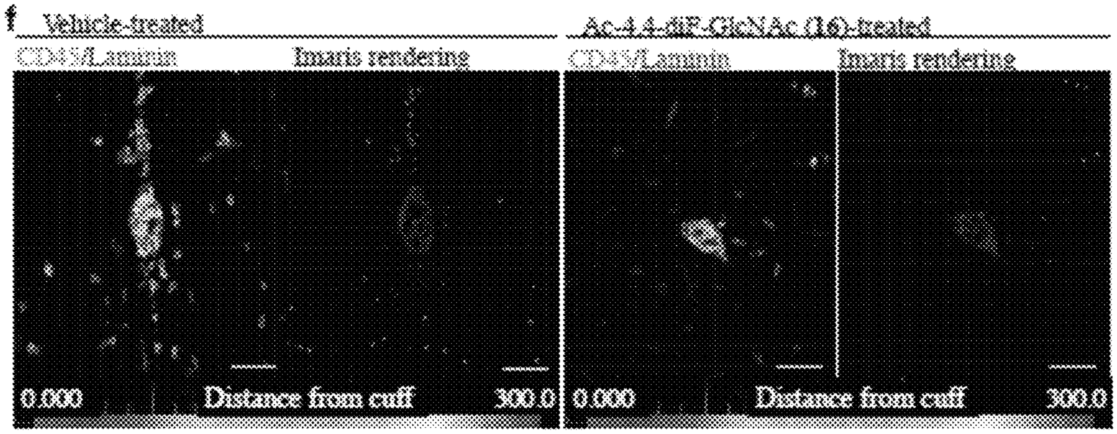

Previously it was shown that CSPGs are accumulated in perivascular cuffs and may have a role in activating immune cells and promoting their migration into the CNS [Stephenson, E. L. et al. Chondroitin sulfate proteoglycans as novel drivers of leucocyte infiltration in multiple sclerosis. Brain: a journal of neurology 141, 1094-1110 (2018)]. For the current study, cervical spinal cord sections from EAE mice treated with Ac-4,4-diF-GlcNAc 16 or vehicle were stained with pan-laminin and CD45. Confocal images were processed by Imaris software to quantify the number of CD45+ cells and their intra-parenchymal distances from perivascular cuffs as previously described [Stephenson, E. L. et al. Chondroitin sulfate proteoglycans as novel drivers of leucocyte infiltration in multiple sclerosis. Brain: a journal of neurology 141, 1094-1110 (2018)] (FIG. 10*f*). In agreement with the flow cytometry findings of reduced infiltrating monocytes and lymphocytes, Ac-4,4-diF-GlcNAc 16 treated EAE mice had significantly fewer CD45+ cells in the vicinity of perivascular cuffs (FIG. 10*g*).

Figure 10H:
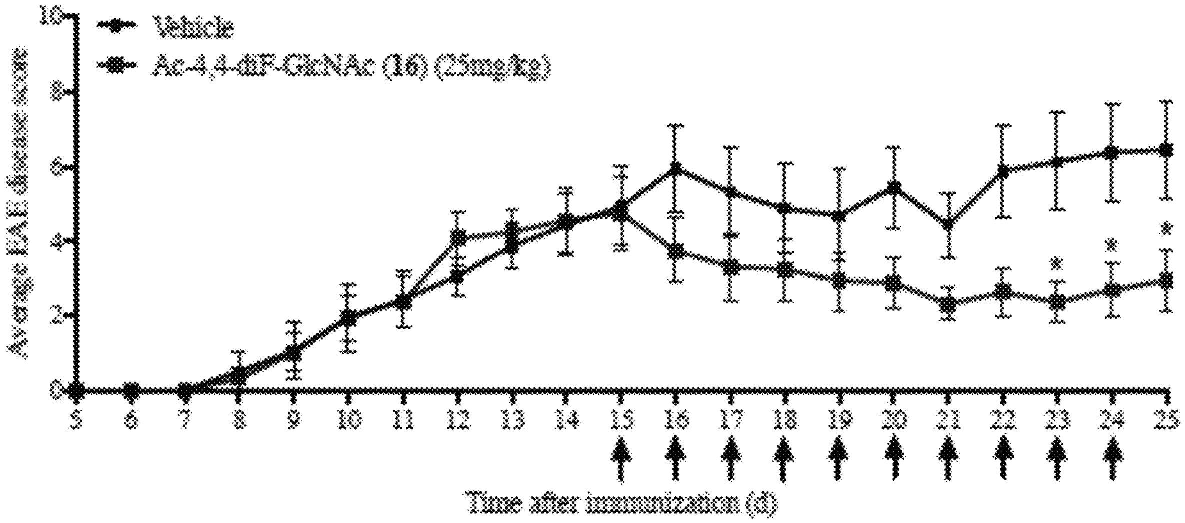
Figure 10I:
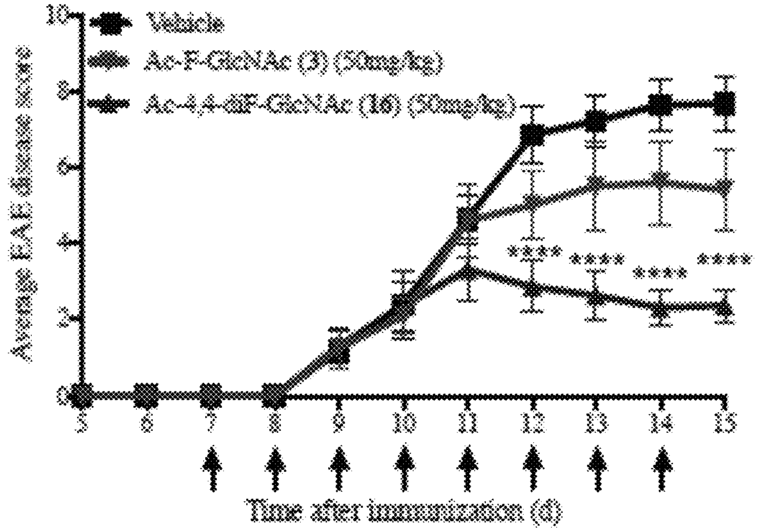

In the second treatment regimen, the difluorinated compound was tested for its ability to lower disease score after mice had accumulated disease. Treatment (daily, 25 $mgkg^{-1}$) was initiated after mice reached peak EAE clinical score (day 15). Over the next 10 days, Ac-4,4-diF-GlcNAc 16 significantly reduced EAE clinical severity (FIG. 10*h*). It was previously shown that 50 $mgkg^{-1}$ of fluorosamine (Ac-4-F-GlcNAc 3), with treatment initiated prior to EAE signs or from peak clinical severity, reduced the ensuing EAE clinical disability [Keough, M. B. et al. An inhibitor of chondroitin sulfate proteoglycan synthesis promotes central nervous system remyelination. Nature communications 7, 11312 (2016)]. Thus, EAE mice were treated with either vehicle, fluorosamine/Ac-4-F-GlcNAc 3, or Ac-4,4-diF-GlcNAc 16 at the higher dose of 50 $mgkg^{-1}$. The difluorinated Ac-4,4-diF-GlcNAc produced a pronounced reduction in EAE clinical severity beyond that seen for the monofluorinated Ac-4-F-GlcNAc (FIG. 10*i*).

Discussion

While CSPGs play an important role in brain physiology, such as in regulating plasticity in perineuronal nets [Carulli, D. et al. Composition of perineuronal nets in the adult rat cerebellum and the cellular origin of their components. The Journal of comparative neurology 494, 559-577 (2006)], excessively elevated CSPGs drive neuroinflammation and interfere with processes of repair [Haylock-Jacobs, S., Keough, M. B., Lau, L. & Yong, V. W. Chondroitin sulphate proteoglycans: extracellular matrix proteins that regulate immunity of the central nervous system. Autoimmunity reviews 10, 766-772 (2011); Pu, A., Stephenson, E. L. & Yong, V. W. The extracellular matrix: Focus on oligodendrocyte biology and targeting CSPGs for remyelination therapies. Glia (2018)]. Many efforts have been made to cleave abnormally deposited CSPGs in CNS lesions, but this will release their GAG chains which have pro-inflammatory capacities [Zhou, J., Nagarkatti, P., Zhong, Y. & Nagarkatti, M. Immune modulation by chondroitin sulfate and its degraded disaccharide product in the development of an experimental model of multiple sclerosis. Journal of neuroimmunology 223, 55-64 (2010)]. Therefore, it was aimed to develop compounds to target the synthetic pathway of CSPGs prior to their release into the ECM. Affecting the synthesis of CSPGs should selectively involve members that are upregulated during inflammation, such as versican, and not other CSPG members previously laid down in perineuronal nets. Targeting CSPGs represents a therapeutic option to alleviate both neurodegenerative and inflammatory components of MS simultaneously.

In this study, fluorinated sugar analogs were investigated and it was found that some of the fluorinated GlcNAc analogs were both effective at reducing the production of inhibitory CSPGs and their chondroitin sulfate GAGs, and attenuating the activity of splenocytes. Compounds were ranked on their capacity to reduce CSPG production in Table 1, and compared for their ability to enhance OPC outgrowth on an inhibitory astrocyte matrix, and reduce T cell proliferation. The top 6 most effective fluorinated compounds at reducing CSPG production were: Ac-4,4-diF-GlcNAc 16, Ac-4-F-GlcNAcOH 10, Ac-4-F-GalNAc 13, Ac-4-F-GlcNAcOPr 7, Ac-4-F-GlcNAc 3, and Ac-4-F-GlcNAcOBu 8.

The similarity of chemical structures between the most effective compounds highlights the constraints on the modifications of groups on these molecules. The presence of bulky ester protecting groups adds excessive lipophilicity of the molecule; this may impair the ability of compounds to enter cells, slow down hydrolysis by esterases, or impede their ability to interact with 4-epimerase.

While compounds such as Ac-4,4-diF-GlcNAc 16 reduced GAG levels (FIG. 4D, FIG. 14), since they are targeted at the GAG synthesis pathway, it is intriguing that the amount of the proteoglycan core protein is also lowered (FIG. 4C). It is possible that the GAG synthesis pathway requires its conjugation to the core protein prior to synthesis, and the failure to do this leads to recycling of the core protein. Thus, the lack of chondroitin sulfate GAGs may interfere with the sorting process and excretion of the proteoglycans [Prydz, K.; Dalen, K. T. Synthesis and sorting of proteoglycans. J. Cell Sci. 2000, 113 (2), 193-205] where chondroitin (and heparan) sulfate chains were shown to contain the sorting information over the protein core. The lack of association with the proper enzymes in the endoplasmic reticulum may cause the failure of proteoglycans to move to the Golgi and will thus be degraded.

In this study, the 4,4-difluorinated compound 16 (Ac-4,4-diF-GlcNAc) that was synthesized and investigated reduced CSPG production in astrocytes more effectively than Ac-4-F-GlcNAc 3, and also strongly reduced proliferation of splenocytes, and had no signs of toxicity in neurons. When tested in vivo, compound 16 potently reduced EAE disease score. Notably, prophylactic treatment also decreased the infiltration of monocytes and lymphocytes into the spinal cord. Immunohistochemistry found that there was reduced number of perivascular cuffs, sites where immune cells can infiltrate into the CNS, as well as lowered CD45+ leukocytes in the parenchyma around perivascular cuffs. That Ac-4,4-diF-GlcNAc 16 did not affect levels of circulating leukocytes was notable as this indicated that the compound is not a general immunosuppressant. It was found that the prophylactic treatment scheme (beginning at day 7) was more effective at reducing EAE clinical scores versus the therapeutic scheme (day 15) which, although beginning to show a trend in improvement, did not significantly improve disability until nine days after treatment. This effect may not be solely due to their capacity to reduce splenocyte proliferation as there was no significant improvement in EAE clinical score when mice were treated with 50 mg/kg of Ac-4-F-GlcNAcOH 10, the most effective compound at reducing splenocyte proliferation. However, Ac-4-F-GlcNAcOH 10 also showed evidence of toxicity on neurons.

This study details in vitro and in vivo screening methods of 4-fluorinated analogs to target CSPGs for use in MS. It has implications also for other diseases where CSPGs are upregulated. It was considered that the activities of these compounds may be due to inhibition of not only chondroitin sulfate GAGs, but also heparan sulfate (FIG. 14D) and dermatan sulfate synthesis. A potential mechanism on how 4-fluorinated analogs reduce CSPG synthesis, and the effect on other glycans, is that 4-fluorinated GlcNAc analogs act on glycan pathways by inhibiting the 4-epimerase enzyme. However, it is likely that these fluorinated analogs interfere with other steps of GAG synthesis, which would support the observation that analogs reduced both CSPG and HSPG synthesis. A second mechanism is depletion of cellular UTP available to natural sugar pools, resulting in inhibition of glycan biosynthesis. Previous studies also support that fluorinated analogs deplete cellular UTP by acting as decoy precursors to form UDP-fluoro-analogs, reducing cellular UTP available to form the UDP-GalNAc and UDP-GlcNAc [van Wijk, X. M. et al. A common sugar-nucleotide-mediated mechanism of inhibition of (glycosamino)glycan biosynthesis, as evidenced by 6F-GalNAc (Ac3). FASEB journal: official publication of the Federation of American Societies for Experimental Biology 29, 2993-3002 (2015); Bernacki, R. J. et al. Biochemical characteristics, metabolism, and antitumor activity of several acetylated hexosamines. Journal of supramolecular structure 7, 235-250 (1977); Barthel, S. R. et al. Peracetylated 4-fluoro-glucosamine reduces the content and repertoire of N- and O-glycans without direct incorporation. The Journal of biological chemistry 286, 21717-21731 (2011)]. In the case of 4-fluorinated GalNAc derivative 13 (Ac-4-F-GalNAc) and related 4,4-difluorinated analog 16 (Ac-4,4-diF-GlcNAc), it is possible that 4-F-GalNAc and the related 4,4-difluorinated residue could be added to the GAG chain; however, this would lead to reduced reactivity of the neighboring OH-3 position, because of the strong electron-withdrawing effect of the fluoride. Ultimately, this would reduce nucleophilicity of OH-3 during enzymatic reaction. The immunomodulatory effects on splenocytes could also be due to alteration in other glycan pathways; the reduction in splenocyte proliferation by Ac-GlcNAc 1 has been shown previously [Grigorian, A. et al. N-acetylglucosamine inhibits T-helper 1 (Th1)/T-helper 17 (Th17) cell responses and treats experimental autoimmune encephalomyelitis. J Biol Chem 286, 40133-41 (2011)], and was ascribed to enhanced N-glycan production that interfered with T-cell receptor clustering and downstream signaling.

The ability of the fluorinated analogs to target CSPG elevation and reduce inflammation will have applications in diseases beyond MS where CSPGs are upregulated. Fluorinated analogs have also been shown to directly act on cancer cell lines, suppressing selectin-mediated tumor cell adhesion [Marathe, D. D. et al. Fluorinated per-acetylated GalNAc metabolically alters glycan structures on leukocyte PSGL-1 and reduces cell binding to selectins. Blood 115, 1303-1312 (2010)] and reducing cancer progression [Barthel, S. R. et al. Peracetylated 4-fluoro-glucosamine reduces the content and repertoire of N- and O-glycans without direct incorporation. *The Journal of biological chemistry* 286, 21717-21731 (2011)]. CSPGs are also deposited in traumatic CNS injuries where they are thought to inhibit axonal regeneration; reducing the markedly elevated CSPG production could have long term favorable outcomes for repair.

Thus, it was shown that fluorinated analogs, particularly Ac-4,4-diF-GlcNAc 16 and henceforth named 'difluorosamine', represent a potential therapeutic avenue to target CSPGs and reduce inflammation.

Figure 13:
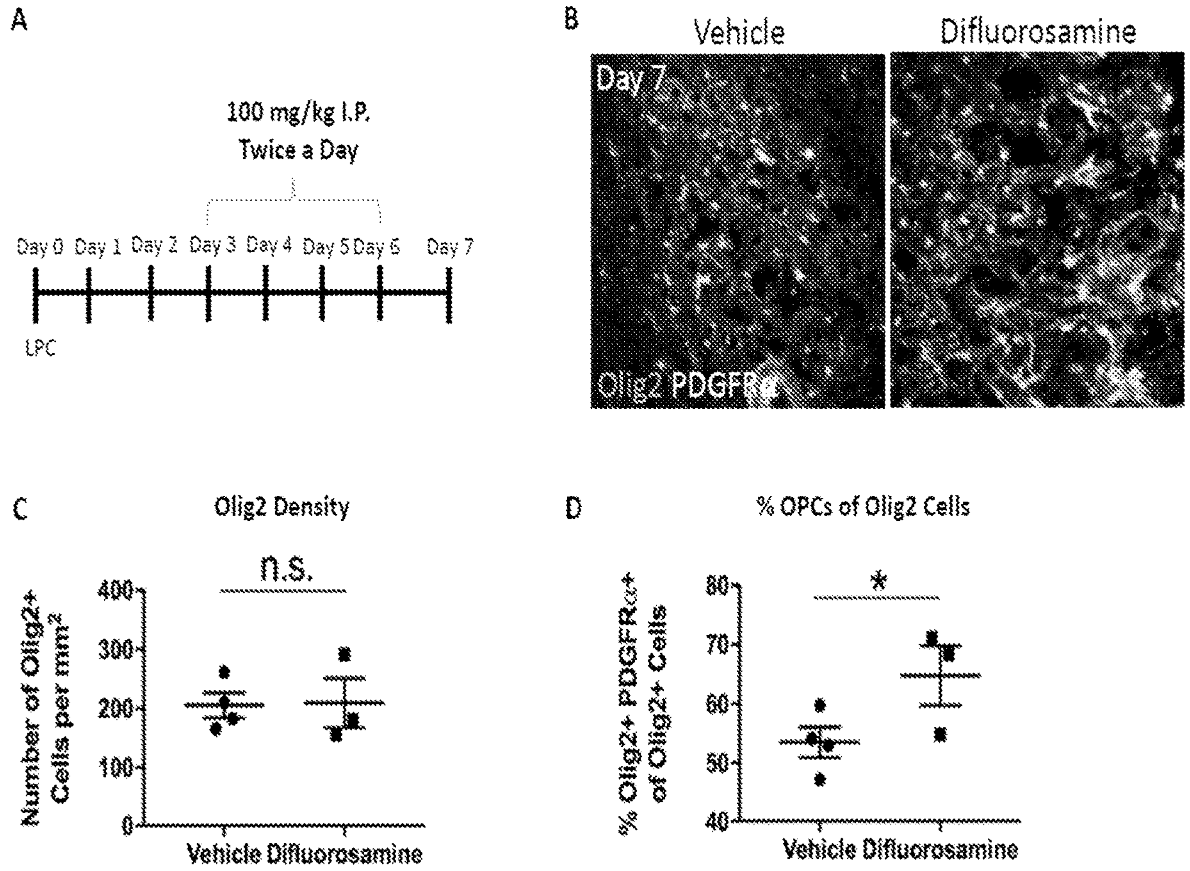
FIG. 13 depicts that treatment of demyelinated mice with difluorosamine significantly increases the percentage of oligodendrocyte lineage cells that are OPCs at Day 7 post-demyelination. A. Difluorosamine was administered to mice demyelinated with lysolecithin by IP injection at a dose of 100 mg/kg twice a day. Mice were treated with either saline vehicle or difluorosamine from Day 3 to Day 6. B. Representative images of lesion epicenters double-stained with oligodendrocyte transcription factor 2 (Olig2; green) and platelet-derived growth factor receptor alpha (PDGFRα; white) from vehicle- and difluorosamine-treated mice at 7 days post-demyelination. C. Lesions in both vehicle- and difluorosamine-treated mice have similar densities of Olig2+ oligodendrocyte lineage cells at 7 days post-demyelination. D. Lesions from mice treated with difluorosamine have a significant increase in the percentage of Olig2+ oligodendrocyte lineage cells that are Olig2+ PDGFRα+ OPCs at 7 days post-demyelination. *$p<0.05$, n.s.=not significant (C., D., One-tailed student's t-test). Three to four mice per group were analyzed.

EXAMPLE 1A: DIFLUOROSAMINE {peracetylated-4,4-difluoro-N-acetylglucosamine, (Ac-4,4-diF-GlcNAc)} INCREASES THE PROPORTION OF OLIGODENDROCYTE PRECURSOR CELLS, A REQUIREMENT FOR REMYELINATION, FOLLOWING DEMYELINATION OF THE MOUSE SPINAL CORD On Day 0, 7 mice were injected with 0.5 μL of 1.0% lysolecithin in the ventral funiculus of the spinal cord. Thereafter, 4 mice were treated from Day 3 to Day 6 with saline vehicle IP twice a day. 3 mice were treated from Day 3 to Day 6 with difluorosamine 100 mg/kg IP twice a day. On Day 7, mice were transcardially perfused with cold PBS and 4% PFA. Thoracic spinal cords were dissected, fixed and analyzed. Sections adjacent to lesion epicenters were triple-stained for Olig2 (cells of the oligodendrocyte lineage), PDGFRα (oligodendrocyte precursor cell) and MBP (myelin). The number of Olig2+, Olig2+ PDGFRα+ (oligodendrocyte precursor cell), and Olig2+ PDGFRα− (presumed mature oligodendrocytes) cells per field of view were quantified blindly. Statistics were conducted using 1-tailed t-tests. See FIG. 13.

It was found that difluorosamine treatment increased the proportion of oligodendrocyte precursor cells (OPCs) after lysolecithin demyelination.

EXAMPLE 2: TARGETING THE CHONDROITIN SULFATE PROTEOGLYCANS: EVALUATING FLUORINATED GLUCOSAMINES AND XYLOSIDES IN SCREENS PERTINENT TO MULTIPLE SCLEROSIS

Mixed Glial Cultures and Enrichment for Oligodendrocyte Precursor Cells and Astrocytes All murine in vitro experiments were in accordance with ethical animal care guidelines by the Animal Care Committee at the University of Calgary and were performed with CD-1 mice as previously described [Keough, M. B. et al. An inhibitor of chondroitin sulfate proteoglycan synthesis promotes central nervous system remyelination. Nature communications 7, 11312 (2016); Medina-Rodriguez, E. M., Arenzana, F. J., Bribian, A. & de Castro, F. Protocol to isolate a large amount of functional oligodendrocyte precursor cells from the cerebral cortex of adult mice and humans. PLoS One 8, e81620 (2013)] and also illustrated in FIG. 7*a*. Postnatal-day 0-2 pups from CD-1 mice (Charles River, Montreal, Canada) were killed by decapitation, and the brains were removed from the skull and placed in Hank's Balanced Salt Solution (HBSS Ca2+ and Mg2+ free) on ice. Meninges were removed and then cortices were minced and pooled into a 50 ml centrifuge tube containing 350 μl HBSS per brain. Tissue was further minced with a 1 ml micropipettor and warmed to 37° C. Seventy-five μl per brain of a papain digestion solution (1.54 μg/ml papain, 360 μg/ml L-cysteine and 703 μg/ml DNAseI) was added to tissue for 30 min at 37° C. Following digestion, the cells were again minced with a 1 ml micropipettor and digestion was stopped by filling the centrifuge tube with mixed glial media (MGM) comprising of Dulbecco's Modified Eagle Media (DMEM) with 10% heat-inactivated fetal bovine serum, 1% L-glutamine, 1% sodium pyruvate and 1% penicillin/streptomycin) and then centrifuged at 1,200 r.p.m. for 10 min. The pellet was resuspended with 3 ml MGM and divided into 3 T-75 poly-L-lysine-coated tissue culture flasks containing 9 ml MGM. The cells were incubated at 37° C. at 8.5% $CO_2$ for 7-8 days, with media changes at approximately 3 and 6 days.

To enrich the mixed cultures for oligodendrocyte precursor cells (OPCs), the mixed cultures were placed on an orbital shaker at 220 r.p.m. at 37° C. and 5% $CO_2$ overnight. The media, containing the loosely adhered cells (i.e., OPCs, microglia and other contaminant cells) versus the strongly adhered astrocytes, was collected and incubated in a 100 mm tissue culture dish at 37° C. and 5% $CO_2$ for 30 minutes, to allow preferred adhesion of microglia. The media were collected a second time, now enriched for OPCs, and was centrifuged at 1,200 r.p.m. for 10 minutes in MGM. After decanting the media, the pellet was resuspended with OPC media [O'Meara, R. W., Ryan, S. D., Colognato, H. & Kothary, R. Derivation of enriched oligodendrocyte cultures and oligodendrocyte/neuron myelinating co-cultures from post-natal murine tissues. J Vis Exp (2011)], and the total cell number was determined using a hemocytometer.

To enrich the mixed culture for astrocytes, following removal of the media with loosely adhered cells, fresh MGM media was added to the T-75 flasks with the strongly adhered astrocytes. Flasks were incubated 37° C. and 5% $CO_2$. Astrocytes were removed by digestion (0.4% trypsin, 33 mg/ml DNAseI and 0.1 mg/ml EDTA at 37° C. and 5% $CO_2$ for 5 minutes). Following centrifugation at 1,200 r.p.m. for 10 minutes, pellet was resuspended and cells were counted and seeded as described below.

In brief, cortices from postnatal days 1-3 mouse brains were dissociated with papain digestion and then plated as a mixed culture for 7 days in a 37° C. incubator at 8.5% $CO_2$ whereupon OPCs and microglia tended to be loosely attached on top of a monolayer of astrocytes; the OPCs and microglia were then shaken off when placed on an orbital shaker at 220 r.p.m. at 37° C. and 5% $CO_2$ overnight. The media containing microglia and OPCs were collected and added to a 100 mm tissue culture dish and left at 37° C. and 5% $CO_2$ for 30 min, to allow preferential adhesion of microglia. The media were collected again, now containing OPCs, and used as the OPC-enriched isolates for experiments. For the remaining adhered cells, largely astrocytes, these were removed with 0.25% trypsin and after centrifugation and washing, these astrocytes were plated at a density of $1.0\times10^5$ cells in flat bottom 96-well plates coated with 10 μg/ml poly-L-lysine. Cells were grown for 7 days at 37° C. and 5% $CO_2$ in MGM and daily media changes. Astrocytes were carefully removed with EDTA treatment (0.2 g EDTA ($Na_4$) per liter PBS, 30 minutes at 37° C. and 5% $CO_2$) and mechanical dislodgement with a micropipetter. The remaining ECM left behind was covered with PBS at 4° C. until OPCs were seeded. Enriched OPCs from mixed glial cultures were seeded at a density of $5\text{-}10\times10^4$ cells per well in OPC media and grown at 37° C. and 8.5% $CO_2$ for 18-24 h and then were fixed with 4% ice-cold paraformaldehyde at 4° C. for 10 min, rinsed with PBS, and stored at 4° C. until immunocytochemistry.

Growth of OPCs on Astrocyte-Secreted Extracellular Matrix

Growth of OPCs on astrocyte-produced ECM was conducted as previously described [Keough, M. B. et al. An inhibitor of chondroitin sulfate proteoglycan synthesis promotes central nervous system remyelination. Nature communications 7, 11312 (2016)]. Astrocytes were plated at a density of $1.0\times10^5$ cells in flat bottom 96-well plates coated with 10 ug/ml poly-L-lysine. Cells were grown for 7 days at 37° C. and 5% $CO_2$ in MGM and daily media changes. Astrocytes were carefully removed with EDTA treatment (0.2 g EDTA ($Na_4$)) per liter PBS, 30 minutes at 37° C. and 5% $CO_2$) and mechanical dislodgement with a micropipetter. The remaining ECM left behind was covered with PBS at 4° C. until OPCs were seeded. Enriched OPCs from mixed glial cultures were seeded at a density of $5\text{-}10\times10^4$ cells per well in OPC media and grown at 37° C. and 8.5% $CO_2$. OPCs were allowed to grow on the astrocyte-secreted ECM for 18-24 h and then cells were fixed with 4% ice-cold paraformaldehyde at 4° C. for 10 min, rinsed with PBS, and stored at 4° C. until immunocytochemistry.

Immunocytochemistry to Sulfatide O4 on Oligodendrocyte Lineage Cells

OPCs were blocked with Licor Odyssey blocking buffer for 60 minutes. The primary antibody to sulfatide O4 on oligodendrocyte lineage cells (EMD Millipore, MAB345) was diluted in Licor blocking buffer (1:250) and incubated overnight at 4° C. Cells were washed with PBS and secondary antibodies and nuclear yellow (1:1000 dilution) for detecting cell nuclei, were added with Licor blocking buffer for 60 minutes. Following a PBS wash, cells were stored at 4° C. before imaging with ImageXpress® Micro Cellular Imaging and Analysis System (Molecular Devices, Sunnyvale, CA) and analyzed by MetaExpress multiwavelength cell scoring program.

ImageXpress Acquisition and MetaXpress Analysis 96-well plates were imaged with ImageXpress® Micro Cellular Imaging and Analysis System (Molecular Devices, Sunnyvale, CA). Twelve images per well were collected at ×10 magnification. Images were processed with MetaXpress analysis software. OPC outgrowth was calculated by the MetaExpress® "neurite outgrowth" software module which uses fluorescence and user-modified parameters to document the overall extent of processes emanating from the cell soma, regardless of size of the protrusions or the number of branches. This was previously detailed elsewhere [Cua, R. C.; Lau, L. W.; Keough, M. B.; Midha, R.; Apte, S. S.; and Yong, V. W. Overcoming neurite-inhibitory chondroitin sulfate proteoglycans in the astrocyte matrix. Glia 2013, 61 (6), 972-84]. Live-dead cell assay was calculated with MetaXpress analysis software with the "multiwavelength cell scoring", which uses fluorescent intensity to measure co-localization of calcein AM, propidium iodide, and nuclear yellow. Data from the 12 images were averaged to a single data point per well, wherein the OPC outgrowth data calculated from the MetaExpress® "neurite outgrowth" readout was divided by data from the same 12 fields of cell number that was acquired through the multiwavelength cell scoring. This provided mean outgrowth per cell per well, with four well replicates per treatment. Experiments were repeated at least twice.

Western Blot of Astrocyte Conditioned Medium

Astrocytes were plated in uncoated 6-well plates (3 replicate wells per treatment) at $1\times10^6$ cells/well in mixed glial media, and incubated at 5% $CO_2$ and 37° C. Astrocytes were treated with compounds at 50 μM in AIM-V media for 48 hours. Media was pooled from 3 replicate wells in 15 ml 100K cutoff centricon tubes (EMD Millipore, #UFC905008), which were spun on an ultracentrifuge at 5000× g for 2 cycles of 10 minutes each. When harvested, the cell lysate was kept on ice for 5 minutes with 250 μL of RIPA buffer (ThermoFisher Scientific #89900) containing proteinase inhibitor, and then collected and centrifuged at 14000 g for 5 minutes. Total protein was quantified using a Bradford assay. Conditioned media that were to be probed for chondroitin 4-sulfate GAGs (Millipore, #MAB2030) were first digested with 0.2 U/ml chondroitinase ABC for overnight at 37° C. to remove chondroitin sulfate sidechains. Blots that were to be probed with CSA (2H6, Cosmo) or CS56 (Abcam #ab11570) were not exposed to chondroitinase ABC. Samples were heat denatured with NuPAGE® LDS Sample buffer at 70° C. for 10 minutes and then loaded into 3-8% tris-acetate pre-cast gels (ThermoFisher, #EA0478BOX). The gels were electrophoresed at a constant 150 V for 90 minutes and transferred to a 0.2 mm polyvinylidene fluoride membrane at a constant 250 mA for 60 minutes. The membranes were blocked for one hour with 10% skim milk in Tris-buffered saline (TBS; 0.9% NaCl, 10 mM Tris-HCl, pH 7.5) containing 0.5% Tween 20 (TBS-T). Primary antibodies were added in 3% skim milk and incubated overnight at 4° C. The membranes were washed 5×5 minutes with TBS-T. HRP-conjugated secondary antibodies were incubated for 120 minutes. The membranes were washed again for 5×5 minutes with TBS-T. Membranes were developed using an ECL chemiluminescence kit (GE Lifesciences) and manually exposed to developing and fixative solutions. Band density was quantified using Gel Analysis on ImageJ. A rectangular shape measured the density of bands for each lane. Bands were normalized from the same gel to a lane with untreated astrocytes on the same gel. This was used to compare relative densities across different gels.

Splenocytes Cell Cultures and Thymidine Proliferation Assays

The spleens were isolated from 8-10-week-old female C57BL/6 mice and homogenized. The cells were isolated by Ficoll gradient and spun for 30 min at 1,800 r.p.m. The cell suspension was removed and the cells were washed once with PBS. The cell pellet was subsequently re-suspended in Roswell Park Memorial Institute media containing 10% fetal bovine serum, 1% penicillin/streptomycin, 1% sodium pyruvate and 1% L-glutamine. Trypan blue exclusion was used to count live cells, and the cells were plated at $2.5\times10^5$ cells per well in a round-bottom 96-well plate and activated with 1,000 ng/ml plate-bound anti-CD3 and 1,000 ng/ml anti-CD28 suspended in media to preferentially activate T lymphocytes. Compounds were added at final concentrations of 25 μM. The cells were kept at 37° C. and 5% $CO_2$ for 30 h, after which 10 μl/well (1 μCi per well) of 3H-thymidine was added for 18 h. The cells containing thymidine were harvested onto filter mats using a cell harvester and mats were allowed to dry for 24 h. The results were read by liquid scintillation counts.

Flow Cytometry for Propidium Iodide Staining for DNA Cell Cycle Analysis and Annexin V/Propidium Iodide Staining Cell cycle staining with propidium iodide (PI) and analysis by flow cytometry gives percentage of cells in apoptosis, G1, G2, and synthesis, and apoptosis. Following a membrane permeabilization, PI chelates to DNA and level of staining specifies the stage of the cell cycle (e.g., G2 phase will have twice the DNA and thus twice the PI signal as G1 phase, apoptotic cells contain less DNA than healthy cells and are identified by low PI staining). $1\times10^6$ splenocytes were used per sample, with four replicates per condition. Cells were collected into a tube with PBS and centrifuged (200 r.p.m. for 5 minutes). Pellet was resuspended in 500 μl PBS and 500 μl ice cold 100% ethanol was slowly added with gentle vortexing of sample. Cell suspension was stored at 4° C. for at least 2 hours (up to two weeks). Next, the suspension was centrifuged at 200 r.p.m. for 3 minutes, pellet was resuspended in PBS and suspension was centrifuged at 200 r.p.m for 10 minutes at 4° C. Pellet was resuspended in 350 μl of PI staining buffer (50 μg/ml propidium iodide, 0.1% TritonX100, 0.2 mg Dnase free Rnase A in PBS) and incubated for 30-45 minutes at room temperature. Suspension was transferred to a FACs tube and analyzed. Annexin V/Propidium iodide staining was detected using the Annexin V FITC apoptosis detection kit (BD Biosciences, #556547), which was performed according to manufacturer's instructions.

Bone Marrow-Derived Macrophage (BMDM) Cultures

Femurs were carefully removed from euthanized female C57BI/6 mice, and marrow was flushed into a culture plate with cold complete bone marrow growth medium (DMEM, 10% fetal bovine serum, and the supplements 1% penicillin/streptomycin, 1% glutamine, 1% non-essential amino acids, and 10% supernatant from L929 cell-line enriched in macrophage-colony stimulating factor). Cells were spun at 1100 rpm for 10 minutes, resuspended in fresh growth medium and plated at $10\times10^6$ cells/ml in a 10 cm culture dish. Cells were grown in DMEM with supplements and L929 supernatant for 5 days, then half the medium was replaced with fresh growth medium. On day 7 growth medium was replaced with DMEM with 10% FBS and supplements. Cells were used on day 8, and experiments were conducted in DMEM with 1% FBS and supplements unless otherwise specified.

TNFα ELISA

BMDM were plated at 25,000 cells in 96-well plates in DMEM+L929 media. After 24 hours media was changed to DMEM+1% FBS. One hour later, cells were treated with 25 μM compounds or PBS. After 1 hour LPS (final concentration 100 ng/ml) was added. Following 24 hours, conditioned media was harvested for TNFα ELISA (Thermo Scientific), which was performed according to manufacturer's instructions.

Human Neuron Cell Cultures and the ATP Assay

Human fetal neurons were plated at $10\times10^4$ cells/well in 96 well plates as previously described [Vecil, G. G. et al. Interleukin-1 is a key regulator of matrix metalloproteinase-9 expression in human neurons in culture and following mouse brain trauma in vivo. Journal of Neuroscience Research 61, 212-224 (2000)]. After 24 hours neurons were treated with 100 μM compounds and incubated for 24 hours. The ATP assay (CellTiter-Glo Luminescent Cell Viability Assay; Promega, Madison, WI, USA) was then performed to test for toxicity according to manufacturer's instructions.

Propidium Iodide/Calcein AM Immunocytochemistry

A mixture was created containing propidium iodide (10 μg/ml) to stain dead cells, 10 μM Calcein AM (ThermoFisher, #C3100MP) to identify live cells, and 2 drops per ml of media of NucBlue™ Live ReadyProbes™ Reagent (ThermoFisher, #R37605) to identify nuclei. The mixture was added to plate media and incubated for 20-30 minutes at 37° C. and 5% $CO_2$ before imaging. Excitation/emission of calcein-AM ($\lambda_{ex}$ 490 nm, $\lambda_{em}$ 515 nm), propidium iodide ($\lambda_{ex}$ 535 nm, $\lambda_{em}$ 617 nm), and nuclear blue ($\lambda_{ex}$ 350 nm, $\lambda_{em}$ 461 nm) was performed using ImageXpress® Micro Cellular Imaging and Analysis System (Molecular Devices, Sunnyvale, CA) and analyzed by MetaExpress multiwavelength cell scoring program.

Experimental Autoimmune Encephalomyelitis (EAE)

All procedures were in accordance with guidelines of the Canadian Council of Animal Care and have received approval by local ethics committee. EAE experiments used seven to ten-week-old female C57Bl/6 female mice (Charles River, Montreal, Canada). Mice were anaesthetized with ketamine (200 mg/kg) and xylosine (10 mg/kg) and then injected with 50 μl (200 μg) of $MOG_{35-50}$ (peptide 35-55, synthesized by the Peptide Facility of the University of Calgary), emulsified in complete Freud's adjuvant (CFA) containing 10 mg/ml of heat inactivated *Mycobacterium tuberculosis* H37RA (Difco) injected subcutaneously into each hind flank. At time of $MOG_{35-55}$ immunization and again 2 days later, each animal received 300 ng of pertussis toxin. Mice were evaluated daily for weight loss, and scored daily for clinical signs of EAE with a 15-point scale [Weaver, A. et al. An elevated matrix metalloproteinase (MMP) in an animal model of multiple sclerosis is protective by affecting Th1/Th2 polarization. FASEB journal: official publication of the Federation of American Societies for Experimental Biology 19, 1668-1670 (2005)].

For treatment regimen 1, mice were randomized into two groups of eight mice on day of $MOG_{35-55}$ immunization. Intraperitoneal treatment with either Ac-4,4-diF-GlcNAc (25 mg/kg, dissolved in saline) or vehicle (saline) was done blinded, and began on day 7 and continued once a day until sacrifice on day 15. Following lethal anaesthesia with intraperitoneal ketamine/xylosine (10 mg/kg), blood was taken for FACs analysis and mice were then PBS-perfused. Lumbar/thoracic spinal cord were dissected and placed in PBS for FACs analysis. Cervical spinal cord and the cerebellum were taken for immunohistochemistry. Sections taken for immunohistochemistry were placed in 4% paraformaldehyde (PFA) at 4° C. for 24 hours, and then placed in (30%) sucrose for at least 72 hours in 4° C. Tissues were then washed in PBS, dried, and frozen in Optimal cutting temperature compound (OCT) in moulds, and stored in −80° C. until sectioning with a cryostat.

For treatment regimen 2, mice were randomized into two groups of nine on day of $MOG_{35-55}$ immunization. One mouse from the Ac-4,4-diF-GlcNAc group was removed due to an unrelated skin lesion. Intraperitoneal treatment with either Ac-4,4-diF-GlcNAc (25 mg/kg, dissolved in saline) or vehicle (saline) was done blinded, and began on day 15 and continued once a day until sacrifice on day 24. Mice and tissue were processed in the same manner as regimen 1.

Treatment with 50 mg/kg of Ac-4-F-GlcNAc, 50 mg/kg Ac-4,4-diF-GlcNAc, or saline was intraperitoneal and conducted as treatment regimen 1. Thirty mice were immunized for EAE and then randomized into three groups of ten. Treatments were given blinded, and administered daily from pre-onset (day 7) until peak (day 15). Mice and tissue were processed in the same manner as regimen 1.

Flow Cytometry of Spinal Cord and Circulating Leukocytes

To assess the inflammatory profile of circulating leukocytes, we performed flow cytometry using a modified protocol published previously [Bellavance, M. A., Gosselin, D., Yong, V. W., Stys, P. K. & Rivest, S. Patrolling monocytes play a critical role in CX3CR1-mediated neuroprotection during excitotoxicity. Brain Struct Funct 220, 1759-76 (2015)]. Briefly, mice were anaesthetized using ketamine/xylazine, after which blood was drawn via cardiac puncture. Heparin-coated syringes were used to draw approximately 130 μL of blood, which was then subsequently diluted with 70 μL of Hanks' Balanced Salt Solution (HBSS; Gibco) without calcium and magnesium. Fc receptors were then blocked by addition of Mouse BD Fc Block (1:100; BD Pharmingen) for 30 minutes at 4° C. Primary antibodies (1:50) were then added and incubated for 45 minutes at 4° C. The primary antibodies used were CD45-PerCP (BD Pharmingen; Clone 30-F11), CD11b-FITC (BD Pharmingen; Clone M1/70), Ly6G-APC-Cy7 (BD Pharmingen; Clone 1A8), Ly6C-V450 (BD Horizon; Clone AL-21), and CD3-PE (BD Pharmingen; Clone 17A2). Red blood cells were then lysed by rocking samples at room temperature for 12 minutes with 1 mL of BD FACS Lysing Solution (BD Biosciences). Samples were then washed at 1200 rpm for 10 minutes at 4° C., followed by two more washes at 2000 rpm for 3 minutes at 4° C. Prior to acquisition on a flow cytometer (BD LSRII), cells were then fixed in 1% formalin for 10 minutes and then resuspended in HBSS without calcium and magnesium.

For flow cytometry of the spinal cord, spinal cords were dissected following a PBS perfusion. The thoracic and lumber sacral part of isolated spinal cords were separated into neural and leucocyte populations by density gradient centrifugation using isotonic Percoll (GE Healthcare). The leukocytes samples were prepared at 4° C. in fluorescence-activated cell sorting (FACS) buffer solution (BD Biosciences) and Fc receptors were then blocked by addition of Mouse BD Fc Block (1:100; BD Pharmingen) for 30 minutes at 4° C. The cells were stained with antibodies against CD45-PerCP (BD Pharmingen; Clone 30-F11), CD11b-FITC (BD Pharmingen; Clone M1/70) and CD3-APC-Cy7 (BD Pharmingen; Clone 17A2) for 45 minutes and then washed three times with FACS buffer. The cells were fixed in 1% buffered formalin for 10 min and resuspended in the 200 μl of the FACS buffer.

Data acquisition was performed on a flow cytometer (BD FACSAria; BD Biosciences) and analysed with FlowJo software (version 8.6, TreeStar). To ensure proper compensation and gating, unstained samples, appropriate isotype controls, and single-stain controls were included. All data was analyzed using FlowJo software.

Quantification of Number of Perivascular Cuffs Per Spinal Cord and Imaris Quantification of CD45+ Cells Perivascular cuffs were identified with pan-laminin staining of two basement membranes with CD45+ cells clustered within the perivascular space. To obtain the average number of perivascular cuffs per spinal cord, perivascular cuffs were counted on 4 cervical spinal cord sections (each >200 μm apart), and then averaged to obtain the average perivascular cuffs per spinal cord per mouse. The Imaris software (Bitplane, Switzerland) was used to quantify the number and distance of CD45+ cells around perivascular cuffs. CD45+ cells were registered as spots and the laminin-positive membranes were registered as surfaces. The Xtension component in Imaris 'distance transformation' calculated the distance of every CD45+ cell from the perivascular cuff.

Statistical Analysis

Where multiple groups were compared, a one-way ANOVA with Tukey-Kramer's post hoc test for multiple comparisons was used. If the multiple comparisons were against a control group, a Dunnett's post hoc test was used. For comparisons between two groups, unpaired two-tailed Student's t-tests were applied. EAE disease scores were analyzed with two-way repeated-measures ANOVA with Sidak's post-hoc test. $P<0.05$ was considered statistically significant. All graphs presented are mean with standard deviation, unless otherwise specified. A linear regression analysis was also used for FIG. 11. All the statistical analyses were performed with Prism 6.0 software (GraphPad).

Safety Statement

No unexpected or unusually high safety hazards were encountered.

Chemical Synthesis

Benzyl 2-acetamido-2,4-dideoxy-4-fluoro-3,6-di-O-methyl-α-D-glucopyranoside (30) and benzyl 2-acetamido-2,4-dideoxy-4-fluoro-3-O-methyl-α-D-glucopyranoside (31)

Compound 29 (100 mg, 0.319 mmol) was dissolved in anhydrous DMF (2.0 ml) to 0° C.; sodium hydride (60% in mineral oil, 20.4 mg, 0.51 mmol) was then added followed by methyl iodine (32 μl, 0.51 mmol). After stirring the mixture for 1 h at room temperature, MeOH (100 μl) was added to quench the reaction. The mixture was diluted with EtOAc (~30 ml), and washed with 10% brine (~30 ml) and water (30 ml). The organic solution was dried over anhydrous $Na_2SO_4$, and evaporated under reduced pressure. The residue was purified by column chromatography on silica gel using 15% acetone-hexanes as an eluent to afford compound 30 (59.4 mg, 55% yield). Further increasing the polarity of the eluent to 20% acetone-hexanes afforded the compound 31 (28.2 mg, 27% yield). Data for 30: $R_f$=0.40 ($MeOH/CH_2Cl_2$, 3:97). $^1H$ NMR (400 MHz, $CDCl_3$) $\delta_H$ 7.46-7.29 (m, 5H, Bn), 5.66 (d, J=9.2 Hz, 1H, NH), 4.92 (dd, J=3.4, 3.4 Hz, 1H, H-1), 4.74 (d, J=11.8 Hz, 1H, Bn), 4.52 (ddd, J=9.9, 8.6 Hz, $J_{H-F}$=50.6 Hz, 1H, H-4), 4.48 (d, J=11.8 Hz, 1H, Bn), 4.21 (m, 1H, H-2), 3.91 (m, 1H, H-5), 3.67-3.48 (m, 6H, H-3+H-6a+H-6b+OMe), 3.43 (s, 3H, OMe), 1.98 (s, 3H, Ac). $^{13}C$ NMR (101 MHz, $CDCl_3$) $\delta_C$ 169.82 (CO), 136.88, 128.61, 128.24, 128.16 (Ar), 96.86 (C-1), 89.87 (d, $J_{C-F}$=182.8 Hz, C-4), 79.34 (d, $J_{C-F}$=17.1 Hz, C-3), 70.62 (C-6), 69.93 ($CH_2Ph$), 69.00 (d, $J_{C-F}$=23.8 Hz, C-5), 59.54 (OMe-6), 59.45 (d, $J_{C-F}$=2.3 Hz, OMe-3), 51.49 (d, $J_{C-F}$=9.3 Hz, C-2), 23.28 (Ac). HRMS (ESI, positive) m/z calc'd for $C_{17}H_{25}O_5FN$ $[M+H]^+$: 342.1711; found: 342.1714. Data for 31: $R_f$=0.13 (3% $MeOH/CH_2Cl_2$). $^1H$ NMR (400 MHz, $CDCl_3$) $\delta_H$ 7.44-7.30 (m, 5H, Bn), 5.64 (d, J=8.9 Hz, 1H, NH), 4.94 (dd, J=3.4, 3.4 Hz, 1H, H-1), 4.71 (d, J=11.3 Hz, 1H, Bn), 4.56 (ddd, J=9.0, 9.0 Hz, $J_{H-F}$=50.8 Hz, 1H, H-4), 4.49 (d, J=11.3 Hz, 1H, Bn), 4.18 (m, 1H, H-2), 3.93-3.72 (m, 3H, H-6a+H-6b+H-5), 3.60 (ddd, J=8.6, 10.7 Hz, $J_{H-F}$=14.3 Hz, 1H, H-3), 3.52 (d, $J_{H-F}$=1.2 Hz, 3H, OMe), 1.98 (s, 3H, Ac). $^{13}C$ NMR (101 MHz, $CDCl_3$) $\delta_C$ 169.98 (CO), 136.76, 128.66, 128.66, 128.34, 128.16 (Ar), 96.83 (C-1), 89.69 (d, $J_{C-F}$=181.5 Hz, C-4), 79.06 (d, $J_{C-F}$=17.6 Hz, C-3), 70.13 ($CH_2Ph$), 69.82 (d, $J_{C-F}$=25.6 Hz, C-5), 61.10 (C-6), 59.54 (d, $J_{C-F}$=2.5 Hz, OMe), 51.64 (d, $J_{C-F}$=9.0 Hz, C-2), 23.29 (Ac). HRMS (ESI, positive) m/z calc'd for $C_{16}H_{23}O_5FN$ $[M+H]^+$: 328.1555; found: 328.1556.

2-Acetamido-1-O-acetyl-2,4-dideoxy-4-fluoro-3,6-di-O-methyl-α/β-D-glucopyranose (5)

Compound 30 (50 mg, 146 μmol) was dissolved in a mixture of MeOH (5.0 ml) and $CH_2Cl_2$ (2.0 ml). To the solution, was added 20% $Pd(OH)_2$ on charcoal (~30 mg) and AcOH (2 drops), and the mixture was purged with hydrogen gas and stirred under the hydrogen atmosphere for 24 h. The insoluble solid was filtered off with a 0.22 μM membrane syringe filter, and the solution was evaporated under reduced pressure to affor crude compound 32 (35 mg, 95% yield). The residue was dissolved in pyridine (1.0 ml) and $Ac_2O$ (0.5 ml) was added, and the reaction was stirred at room temperature for 2 h. The solution was evaporated to dryness and the residue was purified by column chromatography on silica gel using 4% methanol-$CH_2Cl_2$ as an eluent to afford compound 5 (α/β: 95.7/4.3) (38 mg, 94% yield). $R_f$=0.15 ($MeOH/CH_2Cl_2$, 5:95). $^1H$ NMR (400 MHz, $CDCl_3$) for α-anomer: $\delta_H$ 6.15 (dd, J=3.3, 3.3 Hz, 1H, H-1), 5.98 (d, J=8.3 Hz, 1H, NH), 4.58 (ddd, J=9.8, 8.7 Hz, $J_{H-F}$=50.4 Hz, 1H, H-4), 4.26 (m, 1H, H-2), 3.88 (m, 1H, H-5), 3.67-3.50 (m, 6H, H-3+H-6a+H-6b+OMe), 3.38 (s, 3H, OMe), 2.14 (s, 3H, Ac), 1.99 (s, 3H, Ac). $^{13}C$ NMR (101 MHz, $CDCl_3$) for α-anomer: $\delta_C$ 170.34 (CO), 168.87 (CO), 90.81 (C-1), 89.47 (d, $J_{C-F}$=182.6 Hz, C-4), 78.40 (d, $J_{C-F}$=17.6 Hz, C-3), 71.03 (d, $J_{C-F}$=24.4 Hz, C-5), 70.22 (C-6), 59.54 (OMe), 59.37 (d, $J_{C-F}$=1.7 Hz, OMe), 50.78 (d, $J_{C-F}$=9.5 Hz, C-2), 23.06 (Ac), 20.86 (Ac). Selected $^1H$ NMR (400 MHz, $CDCl_3$) for β-anomer: $\delta_H$ 5.83 (d, J=8.4 Hz, 1H, H-1), 5.61 (d, J=10.7 Hz, 1H, NH), 4.50 (ddd, J=9.7, 8.2 Hz, $J_{H-F}$=50.4 Hz, 1H, H-4), 3.38 (s, 3H, OMe), 2.06 (s, 3H, Ac), 1.97 (s, 3H, Ac). Selected $^{13}C$ NMR (101 MHz, $CDCl_3$) for β-anomer: $\delta_C$ 92.08 (C-1), 89.47 (d, $J_{C-F}$=182.6 Hz, C-4), 80.40 (d, $J_{C-F}$=17.0 Hz, C-3), 73.48 (d, $J_{C-F}$=25.6 Hz, C-5), 69.65 (C-6), 54.2 (d, $J_{C-F}$=9.4 Hz, C-2). HRMS (ESI, positive) m/z calc'd for $C_{12}H_{20}O_6FNNa$ [M+Na]+: 316.1167; found: 316.1159.

2-Acetamido-1,6-di-O-acetyl-2,4-dideoxy-4-fluoro-3-O-methyl-α/β-D-glucopyranose (6)

Compound 31 (30 mg, 91.6 μmol) was hydrogenated in a mixture of MeOH (8.0 mL), $CH_2Cl_2$ (2.0 mL) and AcOH (2 drops) in the presence of 20% $Pd(OH)_2$ on charcoal (~20 mg) for 24 h. The reaction mixture was filtered off with a 0.22 μM membrane syringe filter, and the filtrate was evaporated to dryness. The residue was acetylated in a mixture of pyridine (1.0 mL) and $Ac_2O$ (0.5 mL) for 2 h at room temperature. The solution was evaporated to dry mixture and the residue was purified by column chromatography on silica gel using 4% methanol-$CH_2Cl_2$ as an eluent to afford compound 6 (α/β: 84.7/15.3, 26 mg, 88% yield). $R_f$=0.18 ($MeOH/CH_2Cl_2$, 5:95). $^1H$ NMR (400 MHz, $CDCl_3$) for α-anomer: $\delta_H$ 6.15 (dd, J=3.3, 3.3 Hz, 1H, H-1), 5.62 (d, J=8.5 Hz, 1H, NH), 4.56 (ddd, J=9.8, 8.5 Hz, $J_{H-F}$=50.1 Hz, 1H, H-4), 4.38-4.21 (m, 3H, H-2+H-6a+H-6b), 3.99 (m, 1H, H-5), 3.61 (ddd, J=10.9, 8.5 Hz, $J_{H-F}$=13.6 Hz, 1H, H-3), 3.58 (d, J=1.4 Hz, 3H, OMe), 3.55 (t, J=2.0 Hz, 1H), 2.18 (s, 3H, Ac), 2.09 (s, 3H, Ac), 2.03 (s, 3H, Ac). $^{13}C$ NMR (101 MHz, $CDCl_3$) for α-anomer: $\delta_C$ 170.62 (CO), 170.19 (CO), 168.63 (CO), 90.70 (d, $J_{C-F}$=1.3 Hz, C-1), 89.7 (d, $J_{C-F}$=183.5 Hz, C-4), 78.48 (d, $J_{C-F}$=17.33 Hz, C-3), 69.25 (d, $J_{C-F}$=24.6 Hz, C-5), 61.84 (C-6), 59.76 (d, $J_{C-F}$=1.3 Hz, OMe), 50.70 (d, $J_{C-F}$=9.0 Hz, C-2), 23.16 (Ac), 20.86 (Ac), 20.68 (Ac). $^1$H NMR (400 MHz, $CDCl_3$) for β-anomer: $\delta_H$ 5.99 (d, J=7.3 Hz, NH), 5.89 (high order d, J=8.2 Hz, 1H, H-1), 4.45 (overlapped, 1H, H-4), 3.92-3.73 (m, 3H, H-2+H-3+H-5), 3.56 (d, J=~1 Hz, 3H, OMe). Selected $^{13}$C NMR (101 MHz, $CDCl_3$) for β-anomer: $\delta_C$ 91.86 (C-1), 71.99 (d, $J_{C-F}$=24.6 Hz, C-5), 62.15 (C-6), 53.96 (d, $J_{C-F}$=8.6 Hz, C-2). HRMS (ESI, positive) m/z calc'd for $C_{13}H_{21}FNO_7$ $[M+H]^+$: 322.1297; found: 322.1289.

Benzyl 3,6-di-O-acetyl-2,4-dideoxy-4-fluoro-2-trifluroacetamido-α-D-glucopyranoside (35)

Compound 29 (50 mg, 159.6 μmol) was dissolved in 2N HCl (3.0 ml), and the mixture was refluxed for 4 h, the mixture was evaporated to dryness. The residue was redissolved in MeOH, and neutralized with Amberlite IRA-400 ($CO_3^{2-}$) resin. After stirring for 1 h, methyl trifluoroacetate (0.5 ml) was added, and reaction was stirred for 30 min. The resin was filtrated off and concentrated under reduced pressure. The residue containing crude 34 was acetylated in a mixture of pyridine (1.5 ml) and $Ac_2O$ (1.0 ml) for 2 h, and concentrated under reduced pressure. The residue was purified by column chromatography on silica gel using 15% EtOAc-hexanes as the eluent to afford compound 35 (41 mg, 57% yield). $R_f$=0.55 (EtOAc/hexanes, 30:70). $^1$H NMR (400 MHz, $CDCl_3$): $\delta_H$ 7.46-7.30 (m, 5H, Bn), 6.62 (d, J=9.1 Hz, 1H, NH), 5.45 (ddd, J=10.7, 8.9 Hz, $J_{H-F}$=13.9 Hz, 1H, H-3), 4.96 (dd, J=3.3, 3.3 Hz, 1H, H-1), 4.77 (d, J=11.9 Hz, 1H, Bn), 4.58 (d, J=11.9 Hz, 1H, Bn), 4.57 (ddd, J=9.5, 9.5 Hz, $J_{H-F}$=50.6 Hz, 1H, H-4), 4.38 (ddd, J=12.3, 1.9 Hz, $J_{H-F}$=1.9 Hz, 1H, H-6a), 4.33-4.20 (m, 2H, H-6b+H-2), 4.08 (m, 1H, H-5), 2.16 (s, 3H, Ac), 2.11 (s, 3H, Ac). $^{13}$C NMR (101 MHz, $CDCl_3$): $\delta_C$ 171.13 (CO), 170.45 (CO), 128.86, 128.76, 128.38 (Ar), 95.23 (C-1), 86.22 (d, $J_{C-F}$=187.4 Hz, C-4), 70.69 (d, $J_{C-F}$=19.8 Hz, C-3), 70.40 ($PhCH_2$), 67.63 (d, $J_{C-F}$=23.39 Hz, C-5), 61.72 (C-6), 52.37 (d, $J_{C-F}$=7.2 Hz, C-2), 20.71 (Ac), 20.50 (Ac). HRMS (ESI, positive) m/z calc'd for $C_{19}H_{21}O_7F_4NNa$ $[M+Na]^+$: 474.1146; found: 474.1167.

1,3,6-Tri-O-acetyl-2,4-dideoxy-4-fluoro-2-trifluroacetamido-α/β-D-glucopyranose (9)

Compound 35 (30 mg, 66.5 μmol) was dissolved in a mixture of MeOH (5.0 ml), $CH_2Cl_2$ (1.0 ml) and AcOH (1 drop), and 20% $Pd(OH)_2$ on charcoal (~30 mg) was added to the solution. The reaction flask was purged with hydrogen gas and stirred under an atmosphere of hydrogen for 24 h. The reaction mixture was filtered off through a 0.22 μM membrane syringe filter, and the solution was concentrated under reduced pressure. The residue containing crude compound 36 was acetylated in a mixture of pyridine (1.5 ml) and $Ac_2O$ (1.0 ml). After stirring at ambient temperature for 2 h, the mixture was concentrated under reduced pressure. The obtained residue was purified by column chromatography on silica gel using 20% EtOAc-hexanes as the eluent to afford 9 (α/β: 78.7/21.3) (24.6 mg, 92% yield). $R_f$=0.16 (EtOAc/hexanes, 20:80). $^1$H NMR (400 MHz, $CDCl_3$) for α-anomer: $\delta_H$ 5.98 (d, J=9.0 Hz, 1H, NH), 6.23 (dd, J=3.2, 3.2 Hz, 1H, H-1), 4.48 (ddd, J=9.0, 11 Hz, $J_{H-F}$=13.7 Hz, 1H, H-3), 4.64 (ddd, J=9.4, 9.9 Hz, $J_{H-F}$=50.3 Hz, 1H, H-4), 4.46-4.26 (m, 3H, H-2+H-6a+H-6b), 3.87 (m, 1H, H-5), 2.19 (s, 3H, Ac), 2.16 (s, 3H, Ac), 2.13 (s, 3H, Ac). $^{13}$C NMR (101 MHz, $CDCl_3$) for α-anomer: $\delta_C$ 171.89 (CO), 170.44 (CO), 168.32 (CO), 89.42 (C-1), 86.78 (d, $J_{C-F}$=187.2 Hz, C-4), 70.20 (d, $J_{C-F}$=19.4 Hz, C-3), 69.18 (d, $J_{C-F}$=23.4 Hz, C-5), 61.46 (C-6), 51.60 (d, $J_{C-F}$=7.3 Hz, C-4), 20.63 (Ac), 20.60 (Ac), 20.50 (Ac). Selected $^1$H NMR (400 MHz, $CDCl_3$) for β-anomer: $\delta_H$ 7.20 (d, J=9.5 Hz, 1H, NH), 5.77 (d, J=8.7 Hz, 1H, H-1), 5.44 (ddd, J=9.1, 10.9 Hz, $J_{H-F}$=19.9 Hz, 1H, H-3), 4.59 (ddd, J=9.4, 9.4 Hz, $J_{H-F}$=50.3 Hz, 1H, H-4), 4.67-4.07 (m, 3H, H-2+H-6a+H-6b), 3.86 (m, 1H, H-5), 2.14 (s, 3H, Ac), 2.13 (s, 3H, Ac), 2.06 (s, 3H, Ac). Selected $^{13}$C NMR (101 MHz, $CDCl_3$) for β-anomer: $\delta_C$ 171.89 (CO), 170.44 (CO), 169.10 (CO), 91.86 (C-1), 86.1 (d, $J_{C-F}$=188.1 Hz, C-4), 72.39 (d, $J_{C-F}$=24.5 Hz, C-5), 71.85 (d, $J_{C-F}$=19.7 Hz, C-3), 61.61 (C-6), 53.07 (d, $J_{C-F}$=7.4 Hz, C-2), 20.66 (Ac), 20.56 (Ac), 20.41 (Ac). HRMS (ESI, positive) m/z calc'd for $C_{14}H_{17}O_8F_4NNa$ $[M+Na]^+$: 426.0783; found: 426.0776.

2-Acetamido-3,6-di-O-acetyl-2,4-dideoxy-4-fluoro-1-O-propanoyl-α/β-D-glucopyranose (7)

Compound 10 (70 mg, 0.23 mmol) was dissolved in a mixture of anhydrous pyridine (1.0 ml) and $CH_2Cl_2$ (1.5 ml); propionic anhydride (58 μL, 0.46 mmol) was added followed by a catalytic amount of 4-N,N-dimethylaminopyridine, and the mixture was stirred at room temeprarure overnight. A few drops of MeOH were added to quench the reaction, and the mixture was evaporated under reduced pressure. The residue was purified by column chromatography on silica gel using a mixture of 50% EtOAc-hexanes as the eluent to yield compound 7 (α/β 95.5/4.5, 73 mg, 88% yield). $R_f$=0.12 (EtOAc/hexanes, 50:50). $^1$H NMR (400 MHz, Acetone-$d_6$) for α-anomer: $\delta_H$ 7.20 (d, J=9.1 Hz, 1H, NH), 6.10 (dd, J=3.3, 3.3 Hz, 1H, H-1), 5.38 (ddd, J=8.9, 11 Hz, $J_{H-F}$=13.8 Hz, 1H, H-3), 4.67 (ddd, J=9.3, 9.3 Hz, $J_{H-F}$=50.7 Hz, 1H, H-4), 4.39 (dddd, J=3.7, 9.3, 11.2 Hz, $J_{H-F}$=1.1 Hz, 1H, H-2), 4.34 (ddd, J=1.7, 11.9, Hz, $J_{H-F}$=1.1 Hz, 1H, H-6a), 4.27-4.16 (m, 2H, H-6b+H-5), 2.51 (q, J=7.5 Hz, 2H, $CH_3CH_2CO$), 2.05 (s, 6H, 2×Ac), 1.85 (s, 3H, Ac), 1.12 (t, J=7.5 Hz, 3H, $CH_3CH_2CO$). $^{13}$C NMR (101 MHz, Acetone-$d_6$) for α-anomer: $\delta_C$ 172.20 (CO), 169.88 (×2, CO), 169.76 (CO), 89.99 (d, $J_{C-F}$=1.5 Hz, C-1), 87.06 (d, $J_{C-F}$=184.4 Hz, C-4), 70.25 (d, $J_{C-F}$=18.1 Hz, C-3), 69.22 (d, $J_{C-F}$=23.3 Hz, C-5), 61.48 (C-6), 50.36 (d, $J_{C-F}$=7.5 Hz, C-2), 26.77 ($CH_3CH_2CO$), 21.70 (Ac), 19.78 (Ac), 19.68 (Ac), 8.15 ($CH_3CH_2CO$). Selected $^1$H NMR (400 MHz, Acetone-$d_6$) for β-anomer: $\delta_H$ 7.17 (overlapped, 1H, NH), 5.87 (d, J=8.8 Hz, 1H, H-1), 5.43(ddd, partially overlapped, J=8.8, 10.7 Hz, $J_{H-F}$=~13 Hz, 1H, H-3), 4.69 (ddd, J=9.0, 9.7 Hz, $J_{H-F}$=50.6 Hz, 1H, H-4), 4.11 (m, 1H, H-2), 4.02 (m, 1H, H-5), 2.35 (q, J=7.5 Hz, 2H, $CH_3CH_2CO$), 2.04 (s, 6H, 2×Ac), 1.84 (s, 3H, Ac), 1.07 (t, J=7.5 Hz, 3H, $CH_3CH_2CO$). HRMS (ESI, positive) m/z calc'd for $C_{15}H_{22}O_8F_4NNa$ $[M+Na]^+$: 386.1222; found: 386.1218.

2-Acetamido-3,6-di-O-acetyl-1-O-butanoyl-2,4-dideoxy-4-fluoro-α/β-D-glucopyranose (8)

Compound 10 (31 mg, 0.10 mmol) was dissolved in a mixture of anhydrous pyridine (1.0 ml); butyric anhydride (48 μL, 0.30 mmol) was added followed by a catalytic amount of 4-N,N-dimethylaminopyridine, and the mixture was stirret at room temeprarure overnight. A few drops of MeOH were added to quench the reaction, and the mixture was evaporated under reduce pressure. The residue was purified by column chromatography on silica gel using a mixture of 50% EtOAc-hexanes as the eluent to yield compound 8 (α/β 94/6, 30 mg, 78% yield). $R_f$=0.15 (EtOAc/hexanes, 50:50). $^1$H NMR (400 MHz, Acetone-$d_6$) for α-anomer: $\delta_H$ 7.19 (d, J=8.9 Hz, 1H, NH), 6.11 (dd, J=3.3, 3.3 Hz, 1H, H-1), 5.38 (ddd, J=9.0, 11.1 Hz, $J_{H-F}$=13.8 Hz, 1H, H-3), 4.66 (ddd, J=9.0, 9.6 Hz, $J_{H-F}$=50.6 Hz, 1H, H-4), 4.39 (dddd, J=3.8, 9.1, 11.4 Hz, $J_{H-F}$=1.1 Hz, 1H, H-2), 4.34 (m, 1H, H-6a), 4.26-4.15 (m, 2H, H-6b+H-5), 2.54-2.39 (m, 2H, $COCH_2CH_2CH_3$), 2.05 (s, 3H, Ac), 2.05 (s, 3H, Ac), 1.85 (s, 3H, Ac), 1.73-1.62 (m, 2H, $COCH_2CH_2CH_3$), 0.95 (t, J=7.4 Hz, 3H, $COCH_2CH_2CH_3$). $^{13}$C NMR (101 MHz, Acetone-$d_6$) for α-anomer: $\delta_C$ 171.26 (CO), 169.83 (CO), 169.82 (CO), 169.67 (CO), 89.82 (d, $J_{C-F}$=1.3 Hz, C-1), 87.12 (d, $J_{C-F}$=184.5 Hz, C-4), 70.18 (d, $J_{C-F}$=18.4 Hz, C-3), 69.25 (d, $J_{C-F}$=23.4 Hz, C-5), 61.51 (C-6), 50.31 (d, $J_{C-F}$=7.5 Hz, C-2), 35.28 ($COCH_2CH_2CH_3$), 21.65 (Ac), 19.74 (Ac), 19.64 (Ac), 17.87 ($COCH_2CH_2CH_3$), 12.81 ($COCH_2CH_2CH_3$). Selected $^1$H NMR (400 MHz, Acetone-$d_6$) for β-anomer: $\delta_H$ 7.19 (overlapped, 1H, NH), 5.87 (d, J=8.8 Hz, 1H, H-1), 5.43(ddd, partially overlapped, J=8.9, 10.7 Hz, $J_{H-F}$=~13 Hz, 1H, H-3), 4.58 (ddd, J=8.9, 9.8 Hz, $J_{H-F}$=50.7 Hz, 1H, H-4), 4.11 (m, 1H, H-2), 4.01 (m, 1H, H-5), 2.32 (t, J=7.4, 1H, $COCH_aH_bCH_2CH_3$), 2.31 (t, J=7.4, 1H, $COCH_aH_bCH_2CH_3$), 1.65-1.55 (m, 2H, $COCH_aH_bCH_2CH_3$), 0.91 (t, J=7.4 Hz, 3H, $COCH_2CH_2CH_3$). HRMS (ESI, positive) m/z calc'd for $C_{16}H_{24}O_8F_4NNa$ $[M+Na]^+$: 400.1378; found: 400.1370.

Benzyl 2-acetamido-2,4-dideoxy-4-fluoro-3,6-di-O-propanoyl-α-D-glucopyranoside (38)

Compound 29 (50 mg, 159.58 μmol) was dissolved in a mixture of $CH_2Cl_2$(1.0 ml) and pyridine (1.0 ml) at 0° C., and propionic anhydride (122 μL, 957 μmol) was added. The reaction was stirred at room temperature for 2 h. The solution was evaporated to dryness and the residue was purified by column chromatography on silica gel using 20% EtOAc-hexanes as an eluent to afford compound 38 (37.9 mg, 56% yield). $R_f$=0.13 (EtOAc/Toluene, 30:70). $[\alpha]^{25}_D$+58° (c9.2 mg/ml, $CHCl_3$). $^1$H NMR (400 MHz, $CDCl_3$): $\delta_H$ 7.44-7.30 (m, 5H, Bn), 5.75 (d, J=9.5 Hz, 1H, NH), 5.39 (ddd, J=10.9, 9.0 Hz, $J_{H-F}$=14.1 Hz, 1H, H-3), 4.90 (dd, J=3.4, 3.4 Hz, 1H, H-1), 4.74 (d, J=11.8 Hz, 1H, Bn), 4.60 (ddd, 1H, J=9.4, 9.4 Hz, $J_{H-F}$=50.9 Hz, 1H, H-4), 4.53 (d, J=11.8 Hz, 1H, Bn), 4.50-4.43 (m, 1H), 4.38 (ddd, J=12.2, 2.0 Hz, $J_{H-F}$ =2.0 Hz, 1H, H-6a), 4.34-4.22 (m, 2H, H-6b+H-2), 4.04 (m, 1H, H-5), 2.47-2.33 (m, 4H, $2\times CH_3CH_2CO$), 1.90 (s, 3H, Ac), 1.18 (t, J=7.4 Hz, 3H, $CH_3CH_2CO$), 1.14 (t, J=7.6 Hz, 3H, $CH_3CH_2CO$). $^{13}$C NMR (101 MHz, $CDCl_3$): $\delta_C$ 174.76 (CO), 173.99 (CO), 169.95 (CO), 136.42, 128.71, 128.43, 128.20 (Ar), 96.50 (C-1), 86.71 (d, $J_{C-F}$=186.4 Hz, C-4) 71.02 (d, $J_{C-F}$=18.7 Hz, C-3), 70.21 ($CH_2Ph$), 67.64 (d, $J_{C-F}$=23.2 Hz, C-5), 61.82 (C-2), 51.67 (d, $J_{C-F}$=7.2 Hz, C-2), 27.54 ($CH_3CH_2CO$), 27.37 ($CH_3CH_2CO$), 23.04 (Ac), 9.11 ($CH_3CH_2CO$), 9.04 ($CH_3CH_2CO$). HRMS (ESI, positive) m/z calc'd for $C_{21}H_{29}O_7FN$ $[M+H]^+$: 426.1923; found: 426.1932.

2-Acetamido-2,4-dideoxy-4-fluoro-3,6-di-O-propanoyl-α/β-D-glucopyranose (11)

Compound 38 (30 mg, 70.5 μmol) was hydrogenated in a mixture of MeOH (5.0 ml) and $CH_2Cl_2$ (1.0 ml) in the presence of 20% $Pd(OH)_2$ on charcoal (~30 mg) and AcOH (1 drop) for 24 h. The mixture was filtered off with a 0.22 μM membrane syringe filter, and the solution was evaporated to dryness. The residue was purified by column chromatography on silica gel using 70% EtOAc-hexanes as an eluent to afford compound 11 (α/β: 93.4/6.5) (19.6 mg, 83% yield). $R_f$=0.22 (EtOAc/hexanes, 80:20). $^1$H NMR (600 MHz, $CDCl_3$) for α-anomer: $\delta_H$ 6.11 (d, J=9.4 Hz, 1H, NH), 5.45 (ddd, J=10.9, 9.0 Hz, $J_{H-F}$=14.0 Hz 1H, H-3), 5.21 (ddd, J=~3.6, 3.6, 3.2 Hz, 1H, H-1), 4.52 (ddd, J=9.5, 9.5 Hz, $J_{H-F}$=51.1 Hz, 1H, H-4), 4.45 (m, 1H, H-6a), 4.29-4.19 (m, 3H, H-6b+H-5+H-2), 2.42-2.35 (m, 4H, $2\times CH_3CH_2CO$), 1.97 (s, 3H, Ac), 1.90 (br, 1H, OH), 1.16 (t, J=7.6, 3H, $CH_3CH_2CO$), 1.14 (t, J=7.6, 3H, $CH_3CH_2CO$). $^{13}$C NMR (151 MHz, $CDCl_3$): $\delta_C$ 174.97 (CO), 174.37 (CO), 170.62 (CO), 91.51 (C-1), 86.72 (d, $J_{C-F}$=186.6 Hz, C-4), 70.64 (d, $J_{C-F}$=187.2 Hz, C-4), 70.64 (d, $J_{C-F}$=18.5 Hz, C-3), 67.13 (d, $J_{C-F}$=23.4 Hz, C-5), 61.88 (C-6), 52.07 (d, $J_{C-F}$=6.7 Hz, C-2), 27.55 ($CH_3CH_2CO$), 27.34 ($CH_3CH_2CO$), 23.04 (Ac), 9.10 ($CH_3CH_2CO$), 9.00 ($CH_3CH_2CO$). Selected $^1$H NMR (600 MHz, $CDCl_3$) for β-anomer: $\delta_H$ 6.45 (d, J=7.3 Hz, 1H, NH), 5.26 (m, 1H, H-1), 5.15 5.45 (ddd, J=10.9, 8.7 Hz, $J_{H-F}$=14.3 Hz 1H, H-3), 3.74 (m, 1H, H-5), 2.01 (s, 3H, Ac). HRMS (ESI, positive) m/z calc'd for C14$H_{23}O_7$NF $[M+H]^+$: 336.1453; found: 336.1450.

Benzyl 2-acetamido-3,6-di-O-butanoyl-2,4-dideoxy-4-fluoro-α-D-glucopyranoside (39)

To a solution of compound 29 (50 mg, 159.58 μmol) in anhydrous $CH_2Cl_2$(1.0 ml) and pyridine(1.0 ml) at 0° C., was added butyric anhydride (157 μL, 957 μmol) dropwise, and the reaction was stirred at room temperature for 2 h. The mixture was evaporated to dryness under reduced pressure. The obtained residue was purified by column chromatography on silica gel using 25% EtOAc-hexanes as the eluent to afford compound 39 (66.1 mg, 91.3% yield). $R_f$=0.25 (EtOAc/Toluene, 30:70). $[\alpha]^{25}_D$+81.7° (c 0.92, $CHCl_3$). $^1$H NMR (400 MHz, $CDCl_3$): $\delta_H$ 7.43-7.30 (m, 5H, Bn), 5.81 (d, J=9.5 Hz, 1H, NH), 5.39 (ddd, J=10.9, 9.0 Hz, $J_{H-F}$=14.1 Hz, 1H, H-3), 4.90 (dd, J=3.3, 3.3 Hz, 1H, H-1), 4.73 (d, J=11.9 Hz, 1H, Bn), 4.52 (d, J=11.9 Hz, 1H, Bn), 4.51 (ddd, J=9.4, 9.4 Hz, $J_{H-F}$=51.0 Hz, 1H, H-4), 4.37 (ddd, J=12.2, 1.9 Hz, $J_{H-F}$=1.9 Hz, 1H, H-6a), 4.34-4.21 (m, 2H, H-6b+H-2), 4.04 (m, 1H, H-5), 2.42-2.29 (m, 4H, $2\times CH_3CH_2CH_2CO$), 1.89 (s, 3H, Ac), 1.76-1.54 (m, 4H, $2\times CH_3CH_2CH_2CO$), 0.98 (t, J=7.5 Hz, 3H, $CH_3CH_2CH_2CO$), 0.94 (t, J=7.5 Hz, 3H, $CH_3CH_2CH_2CO$). $^{13}$C NMR (101 MHz, $CDCl_3$): $\delta_C$ 173.87 (CO), 173.16 (CO), 169.93 (CO), 136.44, 128.68, 128.40, 128.18 (Ar), 96.47 (C-1), 86.76 (d, $J_{C-F}$=186.8 Hz, C-4), 70.81 (d, $J_{C-F}$=18.6 Hz, C-3), 70.16 ($CH_2Ph$), 67.63 (d, $J_{C-F}$=23.0 Hz, C-5), 61.73 (C-6), 51.64 (d, $J_{C-F}$=6.9 Hz, C-2), 36.04 ($CH_3CH_2CH_2CO$), 35.95 ($CH_3CH_2CH_2CO$), 23.03(Ac), 18.40 ($CH_3CH_2CH_2CO$), 18.37 ($CH_3CH_2CH_2CO$), 13.63 ($CH_3CH_2CH_2CO$), 13.45 ($CH_3CH_2CH_2CO$). HRMS (ESI, positive) m/z calc'd for $C_{23}H_{33}O_7FN$ $[M+H]^+$: 454.2236; found: 454.2245.

2-Acetamido-3,6-di-O-butanoyl-2,4-dideoxy-4-fluoro-α/β-3-D-glucopyranose (12)

Compound 39 (50 mg, 110 μmol) was dissolved in a mixture of MeOH (5.0 ml) and $CH_2Cl_2$ (1.0 ml); to this solution was added 20% $Pd(OH)_2$ on charcoal (~30 mg) and AcOH (1 drop). The reaction flask was purged with hydrogen gas, and the reaction was stirred in the presence of hydrogen atmosphere for 24 h. The mixture was filtered off through a 0.22 μM membrane syringe filter and the solution was evaporated under reduced pressure. The residue was purified by column chromatography on silica gel using 70% EtOAc-hexanes as the eluent to provide compound 12 (α/β: 96.2/3.8) (35.9 mg, 89.8% yield). $R_f$=0.31 (EtOAc/hexanes, 80:20). $^1$H NMR (600 MHz, $CDCl_3$) for α-anomer: $\delta_H$ 6.23 (d, J=9.4 Hz, 1H, NH), 5.46 (ddd, J=10.9, 9.0 Hz, $J_{H-F}$=13.9 Hz, 1H, H-3), 5.19 (ddd, J=~3.4, ~3.4, ~3.4 Hz, 1H, H-1), 4.91 (dd, J=4.0, 1.1 Hz, 1H, OH), 4.51 (ddd, J=9.3, 9.3 Hz, $J_{H-F}$=51.0 Hz, 1H, H-4), 4.43 (dd, J=11.9, 1.8 Hz, $J_{H-F}$=1.8 Hz, 1H, H-6a), 4.27-4.17 (m, 3H, H-2+H-5+H-6b), 2.36-2.30 (m, 4H, 2×$CH_3CH_2CH_2CO$), 1.95 (s, 3H, Ac), 1.70-1.59 (m, 4H, 2×$CH_3CH_2CH_2CO$), 0.95 (t, J=7.4 Hz, 3H, $CH_3CH_2CH_2CO$), 0.93 (t, J=7.4 Hz, 3H, $CH_3CH_2CH_2CO$). $^{13}$C NMR (151 MHz, $CDCl_3$): $\delta_C$174.10 (CO), 173.62 (CO), 170.77 (CO), 91.43 (C-1), 86.78 (d, $J_{C-F}$=186.1 Hz, C-4), 70.50 (d, $J_{C-F}$=18.2 Hz, C-3), 67.00 (d, $J_{C-F}$=23.1 Hz, C-5), 61.79 (C-6), 52.10 (d, $J_{C-F}$=7.0 Hz, C-2), 36.04 ($CH_3CH_2CH_2CO$), 35.92 ($CH_3CH_2CH_2CO$), 22.98 (Ac), 18.37 ($CH_3CH_2CH_2CO$), 18.33 ($CH_3CH_2CH_2CO$), 13.57 ($CH_3CH_2CH_2CO$), 13.43 ($CH_3CH_2CH_2CO$). Selected $^1$H NMR (600 MHz, $CDCl_3$) data for β-anomer: $\delta_H$ 6.51 (d, J=7.3 Hz, 1H, NH), 5.24 (m, 1H, H-1), 3.73 (m, 1H, H-5), 1.99 (s, 3H, Ac). HRMS (ESI, positive) m/z calc'd for $C_{16}H_{27}O_7NF$ $[M+H]^+$: 364.1766; found: 364.1751.

Benzyl 2-acetamido-3,6-di-O-acetyl-2,4-dideoxy-4-fluoro-α-D-galactopyranoside (41)

A solution of compound 40 (600 mg, 1.51 mmol) in a mixture of anhydrous $CH_2Cl_2$ (2.5 ml) and anhydrous pyridine (2.5 ml) was cooled to −10° C.; $Tf_2O$ (789 μL, 4.53 mmol) was added. After 1 h at −10° C., MeOH (250 μl) was added to quench the reaction. The mixture was diluted with EtOAc (~30 ml), and the solution was washed with 2N HCl (~30 ml), 10% $NaHCO_3$ (~30 ml) and 10% NaCl (~30 ml), dried over anhydrous $Na_2SO_4$, and concentrated under reduced pressure to afford crude 4-triflate, which was redissolved in a solution of n-$Bu_4NF$ in acetone solution (0.2 g/ml, 5.0 ml). After stirring at room temperature overnight, the mixture was concentrated to dryness. The obtained residue was purified by column chromatography on silica gel using 30% EtOAc-toluene as the eluent to afford compound 41 (320 mg, 53% yield). $R_f$=0.17 (EtOAc/hexanes, 50:50). $^1$H NMR (400 MHz, $CDCl_3$): $\delta_H$ 7.42-7.26 (m, 5H, Bn), 5.69 (d, J=9.6 Hz, 1H, NH), 5.13 (ddd, J=11.4, 2.3 Hz, $J_{H-F}$=27.6 Hz, 1H, H-3), 4.98 (d, J=3.5 Hz, 1H, H-1), 4.81 (ddd, J=<1, 2.5 Hz, $J_{H-F}$=50.6 Hz, 1H), 4.71 (d, J=11.7 Hz, 1H, $CH_aH_bPh$), 4.63 (ddd, J=3.7, 9.8 11.4 Hz, 1H, H-2), 4.51 (d, J=11.7 Hz, 1H, $CH_aH_bPh$), 4.28 (ddd, J=11.3, 6.8 Hz, $J_{H-F}$=0.7 Hz, 1H, H-6a), 4.22 (dd, J=11.3, 6.3 Hz, 1H, H-6b), 4.08 (dddd, J=~6.5, ~6.5, <1 Hz, $J_{H-F}$=28.3 Hz, 1H, H-5), 2.09 (s, 3H, Ac), 2.08 (s, 3H, Ac), 1.90 (s, 3H, Ac). $^{13}$C NMR (101 MHz, $CDCl_3$): $\delta_C$ 171.12 (CO), 170.40 (CO), 169.89 (CO), 136.53, 128.67, 128.36, 128.21 (Ar), 96.90 (C-1), 86.36 (d, $J_{C-F}$=186.0 Hz, C-4), 70.14 ($CH_2Ph$), 68.77 (d, $J_{C-F}$=7.8 Hz, C-3), 67.28 (d, $J_{C-F}$=18.0 Hz, C-5), 61.90 (d, $J_{C-F}$=5.9 Hz, C-6), 47.58 (d, $J_{C-F}$=2.3 Hz, C-2), 23.16 (Ac), 20.79 (Ac), 20.72 (Ac). HRMS (ESI, positive) m/z calc'd for $C_{19}H_{25}O_7NF$ $[M+H]^+$: 398.1610; found: 398.1619.

2-Acetamido-1,3,6-tri-O-acetyl-2,4-dideoxy-4-fluoro-α/β-D-galactopyranose (13)

Compound compound 41 (165 mg, 415 μmol) was dissolved in a mixture of MeOH (10.0 mL), $CH_2Cl_2$ (3.0 mL) and $H_2O$ (4 drops); 20% $Pd(OH)_2$ on charcoal (50 mg) was added, and the flask was purged with hydrogen gas and the reaction was continued under an atmosphere of hydrogen gas for 24 h. The reaction mixture was filtered off through a 0.22 μm membrane syringe filter, and the solution was concentrated under reduced pressure. The obtained residue containing crude hemiacetal 42 was acetylated in a mixture of pyridine (3.0 mL) and $Ac_2O$ (2.0 mL). After stirring at room temperature for 1 h, the mixture was concentrated. The mixture was purified by column chromatography on silica gel using 40% EtOAc-toluene as the eluent to afford compound 13 (α/β: 88/12) (135 mg, 93% yield). $R_f$=0.05 (50% EtOAc/hexanes). $^1$H NMR (400 MHz, $CDCl_3$) data for α-anomer: δ 6.21 (d, J=3.6 Hz, 1H, H-1), 5.70 (d, J=9.1 Hz, 1H, NH), 5.17 (ddd, J=11.7, 2.3 Hz, $J_{H-F}$=26.7 Hz, 1H, H-3), 4.86 (ddd, J=<1, 2.3 Hz, $J_{H-F}$=50.4 Hz, 1H, H-4), 4.75 (ddd, J=3.7, 9.4, 11.4 Hz, 1H, H-2), 4.27 (ddd, J=6.5, 11.2 Hz, $J_{H-F}$=1.1 Hz, 1H, H-6a), 4.20 (dd, J=11.1, 6.4 Hz, 1H, H-6b), 4.11 (ddd, J=6.6, 6.6 Hz, $J_{H-F}$=27.8 Hz, 1H, H-5), 2.16 (s, 3H, Ac), 2.13 (s, 3H, Ac), 2.06 (s, 3H, Ac), 1.94 (s, 3H, Ac). $^{13}$C NMR (101 MHz, $CDCl_3$) δ 171.38 (Ac), 170.42 (Ac), 170.08 (Ac), 168.79 (Ac), 91.13 (C-1), 85.85 (d, $J_{C-F}$=187.4 Hz, C-4), 68.85 (d, $J_{C-F}$=18.4 Hz, C-3), 68.03 (d, $J_{C-F}$=17.9 Hz, C-5), 61.37 (d, $J_{C-F}$=6.4 Hz, C-6), 46.84 (d, $J_{C-F}$=3.0 Hz, C-2), 23.05 (Ac), 20.89 (Ac), 20.77 (Ac), 20.67 (Ac). Selected $^1$H NMR (400 MHz, $CDCl_3$) data for β-anomer: δ 5.94 (d, J=9.3 Hz, 1H, NH), 6.78 (dd, J=8.8 Hz, $J_{H-F}$=0.8 Hz, 1H, H-1), 3.94 (ddd, J=6.4, 6.4 Hz, $J_{H-F}$=26.3 Hz, 1H, H-5), 2.12 (s, 3H, Ac), 2.11 (s, 3H, Ac), 2.07 (s, 3H, Ac), 1.93 (s, 3H, Ac). HRMS (ESI, positive) m/z calculated for $C_{14}H_{20}O_8NFNa$ $[M+Na]^+$: 372.1065; found: 372.1071.

2-Acetamido-1,3,6-tri-O-acetyl-2,4-dideoxy-4-chloro-α/β-D-galactopyranoside (15)

Compound 14 (30 mg, 92.7 μmol) was acetylated in a mixture of pyridine (3.0 ml) and $Ac_2O$ (2.0 ml). After stirring at room temperature for 1 h, the mixture was concentrated. The mixture was purified by column chromatography on silica gel using a 1→5% gradient of methanol-dichloromethane as the eluent to afford the α-anomer of compound 15 (15 mg, 44% yield). $[\alpha]^{25}_D$+96.4° (c0.12, $CHCl_3$). $^1$H NMR (400 MHz, $CDCl_3$): $\delta_H$ 6.20 (d, J=3.6 Hz, 1H, H-1), 5.61 (d, J=9.1 Hz, 1H, NH), 5.27 (dd, J=10.8, 9.5 Hz, 1H, H-3), 4.45 (ddd, J=10.8, 9.2, 3.6 Hz, 1H, H-2), 4.43-4.36 (m, 2H, H-6a+H-6b), 4.08 (ddd, J=2.3, 2.3, 10.5 Hz, 1H, H-5), 4.03 (dd, J=9.6, 10.6 Hz, 1H, H-4), 2.23 (s, 3H, Ac), 2.16 (s, 3H, Ac), 2.13 (s, 3H, Ac), 1.96 (s, 3H, Ac). $^{13}$C NMR (101 MHz, $CDCl_3$): $\delta_C$ 171.48 (CO), 170.42 (CO), 169.98 (CO), 168.57 (CO), 90.75 (C-1), 72.35 (C-3), 71.94 (C-5), 62.33 (C-6), 54.63 (C-4), 51.79 (C-2), 23.04 (Ac), 20.93 (Ac), 20.69 (Ac), 20.64 (Ac). HRMS (ESI, positive) m/z calc'd for $C_{14}H_{20}{}^{35}ClNO_8Na$ $[M+Na]^+$: 388.0770; found: 388.0768; calculated for $C_{14}H_{20}{}^{37}ClNO_8Na$ $[M+Na]^+$: 390.0740; found: 390.0750.

Benzyl 2-acetamido-3,6-di-O-benzyl-2-deoxy-α-D-glucopyranoside (44)

To a solution of compound 43 (9.0 g, 18.4 mmol) in anhydrous $CH_2Cl_2$ (100 ml) at 0° C., $Et_3SiH$ (14.7 ml, 92 mmol) was added, followed by $BF_3{\cdot}Et_2O$ (3.5 mL, 27.6 mmol), and the mixture was stirred at 0° C. for 2 h. After neutralizing the reaction mixture with $NEt_3$, the mixture was evaporated under reduced pressure and the crude mixture was purified by column chromatography on silica gel using a mixture of 60% ethyl acetate-hexanes as the eluent to afford the desired compound 44 (6.51 g, 72% yield). $R_f$=0.44 (AcOEt/hexanes, 60:40). $[\alpha]^{25}_D$+92.8° (c 0.80, $CHCl_3$). $^1$H NMR ($CDCl_3$, 400 MHz): $\delta_H$ 7.42-7.26 (m, 15H, Ph), 5.53 (d, J=5.2 Hz, 1H, NH), 4.91 (d, J=3.6 Hz, 1H, H-1), 4.83-4.22 (m, 6H, $CH_2$), 4.29 (td, J=9.6, 3.6 Hz, 1H, H-2), 3.90-3.61 (m, 5H, H-3, H-4, H-5, H-6), 3.13 (d, J=2.8 Hz, 1H, OH), 1.85 (s, 3H, $CH_3$). $^{13}C$ NMR ($CDCl_3$, 100 MHz): $\delta_C$ 169.86 (CO), 138.63 (C), 137.96, 137.24, 128.54, 128.49, 128.42, 128.05, 128.01, 127.97, 127.75, 127.72, 127.64 (Ar), 97.17 (C-1), 79.92 (C-3), 73.80 ($CH_2$), 73.64 ($CH_2$), 71.97 (C-5), 70.73 (C-4), 70.15 (C-6), 69.58 ($CH_2$), 51.95 (C-2), 23.31 (Ac). HRMS (ESI, positive) m/z calc'd for for $C_{29}H_{34}NO_6[M+H]^+$: 492.2381, found 492.2386.

Benzyl 2-acetamido-3,6-di-O-benzyl-2-deoxy-α-D-xylo-hexopyranosid-4-ulose (45)

Acetic anhydrous (25.0 ml) was added to anhydrous DMSO (50.0 ml) at 0° C., and the mixture was stirred for 10 minutes. Compound 44 (5.3 g, 10.78 mmol) was then added, and the mixture was stirred at room temperature overnight. The reaction was diluted with EtOAc (~300 ml) and the solution was extracted with 10% brine (2×400 ml), and the organic layer was dried over anhydrous $Na_2SO_4$ and evaporated under reduced pressure. The solid was purified by column chromatography on silica gel using a mixture of 20% EtOAc-toluene as the eluent to afford the desired compound 45 (3.48 g, 66% yield). $R_f$=0.40 (EtOAc/hexanes, 50:50). $[\alpha]^{25}_D$+154° (c0.76, $CHCl_3$). $^1H$ NMR ($CD_3COCD_3$, 400 MHz): $\delta_H$ 7.42-7.27 (m, 15H, Ph), 5.56-5.46 (m, 1H, NH), 5.15 (d, J=3.6 Hz, 1H, H-1), 4.93 (d, J=12.0 Hz, 1H, $CH_2$-a), 4.79 (d, J=12.0 Hz, 1H, $CH_2$-b), 4.70-4.43 (m, 5H, H-2, $CH_2$), 4.39 (dd, J=6.0, 3.6 Hz, 1H, H-5), 4.14 (t, J=11.2 Hz, 1H, H-3), 3.96 (dd, J=10.8, 3.6 Hz, 1H, H-6a), 3.96 (dd, J=10.8, 6.0 Hz, 1H, H-6b), 1.90 (s, 3H, $CH_3$). $^{13}C$ NMR ($CD_3COCD_3$, 100 MHz): $\delta_C$ 201.59 (C-4), 169.57 (CO), 137.98, 137.67, 136.62, 128.74, 128.50, 128.48, 128.44, 128.23, 128.12, 128.06, 127.79, 127.79 (Ar), 96.72 (C-1), 79.54 (C-3), 73.87 (C-5), 73.78 ($CH_2$), 72.65 ($CH_2$), 70.44 ($CH_2$), 67.73 (C-6), 54.25 (C-2), 23.30 (Ac). HRMS (ESI, positive) m/z calc'd for for $C_{29}H_{32}NO_6$ $[M+H]^+$: 490.2224, found 490.2236.

Benzyl 2-acetamido-3,6-di-O-benzyl-2,4-dideoxy-4,4-difluoro-α-D-xylo-hexopyranoside (46)

To a cold solution of compound 45 (2.5 g, 5.1 mmol) in anhydrous dichloromethane (20.0 ml) at 0° C., was added DAST (2.0 ml, 15.3 mmol), and the mixture was stirred at 0° C. for 10 minute. The reaction was then stirred at ambient temperature overnight. MeOH (1.0 ml) was added to quench the reaction, and the mixture was diluted with EtOAc (~150 ml), washed with 10% brine (~100 ml) and water (~100 ml), and the organic solution was dried over anhydrous $Na_2SO_4$, and evaporated. The crude mixture was purified by column chromatography on silica gel using 20% EtOAc-hexanes as the eluent to afford compound 46 (1.38 g, 53% yield). $R_f$=0.27 (EtOAc/toluene, 30:70). $[\alpha]^{25}_D$+108.6° (c 0.7, $CHCl_3$). $^1H$ NMR (400 MHz, $CDCl_3$): $\delta_H$ 7.48-7.25 (m, 15H, Bn), 5.41 (d, J=9.1 Hz, 1H, NH), 4.97 (m, 2H, H-1+PhCHaHb), 4.79 (d, J=11.2 Hz, 1H, PhCHaHb), 4.69 (d, J=12.0 Hz, 1H, PhCHaHb), 4.65-4.56 (m, 2H, 2×PhCHaHb), 4.55-4.41 (m, 2H, H-2+PhCHaHb), 4.19 (ddd, J=24.7, 7.4, 2.5 Hz, 1H, H-3), 4.04-3.94 (m, 1H, H-6a), 3.90-3.71 (m, 2H, H-3+H-6b), 1.86 (s, 3H, Ac). $^{13}C$ NMR ($CDCl_3$, 150 MHz): $\delta_C$ 169.71 (CO), 137.91, 137.56, 136.57, 128.65, 128.50, 128.46, 128.31, 128.16, 128.09, 127.77, 127.58 (Ar), 118.62 (dd, $J_{C-F}$=250.9, 255.2 Hz, C-4), 96.29 (C-1), 75.33 (dd, $J_{C-F}$=19.5, 19.5 Hz, C-3), 74.69 ($PhCH_2$), 73.64 ($PhCH_2$), 70.05 (dd, $J_{C-F}$=22.8, 28.3 Hz, C-5), 69.85 ($PhCH_2$), 66.49 (d, $J_{C-F}$=4.6 Hz, C-6), 51.07

($J_{C-F}$=7.9 Hz, C-2), 23.21 (Ac). HRMS (ESI, positive) m/z calc'd for for $C_{29}H_{32}F_2NO_5$ $[M+H]^+$: 512.2243, found 512.2228.

2-Acetamido-1,3,6-tri-O-acetyl-2,4-dideoxy-4,4-difluoro-α/β-D-xylo-hexopyranose (16)

To a solution of compound 46 (1.5 g, 2.93 mmol) in a mixture of MeOH (10.0 ml) and $CH_2Cl_2$ (5.0 ml) was added 20% $Pd(OH)_2$ on charcoal (~150 mg) and AcOH (2 drops), and the mixture was purged with hydrogen gas and stirred under a hydrogen atmosphere for two days. The solution was filtered off with a 0.22 μM membrane syringe filter, and the solution was concentrated under reduced pressure to afford the intermediate 47 (721 mg, 90% yield). $R_f$=0.19 (10% $MeOH/CH_2Cl_2$). Compound 47 (900 mg, 3.7 mmol) was dissolved in pyridine (10.0 ml) and acetic anhydride (8.0 ml) was added. After stirring the reaction for 2 hours at room temperature, the solution was concentrated under reduced pressure. The residue was purified by column chromatography on silica gel using a mixture of 45% EtOAc-hexanes as the eluent to provide desired compound 16 (α/β, 87:13) (1.32 g, 96% yield). $R_f$: =0.20 (EtOAc/toluene, 60:40). $^1H$ NMR (400 MHz, $CDCl_3$) for α-anomer: $\delta_H$ 6.21 (dd, J=2.3, 3.3 Hz, 1H, H-1), 5.57 (d, J=9.1 Hz, 1H, NH), 5.36 (ddd, J=5.1, 11.5 Hz, $J_{H-F}$=19.3 Hz, 1H, H-3), 4.68 (m, 1H, H-2), 4.47 (dd, J=3.2, 11.8 Hz, 1H, H-6a), 4.28 (dd, J=7.2, 12.0 Hz, H-6b), 4.20 (m, 1H, H-5), 2.20 (s, 3H, Ac), 2.19 (s, 3H, Ac), 2.08 (s, 3H, Ac), 1.96 (s, 3H, Ac). $^{13}C$ NMR ($CDCl_3$, 101 MHz) for α-anomer: $\delta_C$ 171.27 (CO), 170.54 (CO), 169.87 (CO), 168.31 (CO), 115.51 (dd, $J_{C-F}$=253.4, 255 Hz, C-4), 90.25 (C-1), 69.63 (dd, $J_{C-F}$=23.2, 27.9 Hz, C-5), 68.21 (dd, $J_{C-F}$=20.0, 20.0 Hz, C-3), 59.80, (d, $J_{C-F}$=5.7 Hz, C-6), 49.94 (d, $J_{C-F}$=6.4 Hz, C-2), 23.00 (Ac), 20.83 (Ac), 20.64 (Ac), 20.54 (Ac). Selected $^1H$ NMR (400 MHz, $CDCl_3$) for β-anomer: $\delta_H$ 5.85 (d, J=8.7 Hz, 1H, H-1), 5.66 (d, J=9.3 Hz, 1H, NH), 5.36 (overlapped, 1H, H-3), 4.50 (overlapped, 1H, H-6a), 4.36 (m, 1H, H-2), 4.03 (ddd, J=3.2, 4.5 Hz, $J_{H-F}$=21.9 Hz, C-5), 2.17 (s, 3H, Ac), 2.14 (s, 3H, Ac), 2.09 (s, 3H, Ac), 1.94 (s, 3H, Ac). Selected $^{13}C$ NMR ($CDCl_3$, 101 MHz) for β-anomer: $\delta_C$ 170.45 (CO), 170.10 (CO), 169.22 (CO), 167.03 (CO), 91.98 (C-1), 59.86 (d, $J_{C-F}$=6.4 Hz, C-6), 52.26 (d, $J_{C-F}$=6.9 Hz, C-2), 23.13 (Ac), 20.78 (Ac), 20.66 (Ac), 20.43 (Ac). HRMS (ESI, positive) m/z calc'd for $C_{14}H_{20}F_2NO_3$ $(M+H^+)$: 368.1151; found: 368.1147.

Benzyl 2-acetamido-3-O-acetyl-6-O-t-butyldimethylsilyl-2,4-dideoxy-4-fluoro-α-D-glucopyranoside (49)

To a solution of compound 29 (103 mg, 328.7 μmol) in anhydrous pyridine (3.0 mL), was added t-butyldimethylsilyl chloride (54.5 mg, 361.6 μmol), and the mixture was stirred at ambient temperature for 3 h. MeOH (100 μl) was added to quench the reaction, and the mixture was evaporated under reduced pressure. The residue was purified by column chromatography on silica gel using 20% acetone-toluene as the eluent to obtain compound 48 (117.3 mg, 83.5% yield). $R_f$=0.62 (Acetone/toluene: 60:40). A portion of compound 48 (111 mg, 259.6 μmol) was acetylated in a mixture of pyridine (2.0 mL) and $Ac_2O$ (1.0 mL) for 2 h at ambient temperature. The mixture was concentrated under reduced pressure and co-evaporated with toluene (2×20 mL) obtain compound 49 (117.3 mg) without further purification. $^1H$ NMR (400 MHz, $CDCl_3$): $\delta_H$ 7.47-7.30 (m, 5H, Ph), 5.74 (d, J=9.5 Hz, 1H, NH), 5.37 (ddd, J=10.8, 9.0 Hz, $J_{H-F}$=14.3

Hz, 1H, H-3), 4.91 (dd, J=3.4, 3.4 Hz, 1H, H-1), 4.74 (d, J=11.8 Hz, 1H, Bn), 4.56 (high order ddd, J=9.2, 9.2 Hz, $J_{H-F}$=51 Hz, 1H, H-4), 4.51 (d, J=11.8 Hz, 2H), 4.26 (m, 1H, H-2), 3.91-3.79 (m, 3H, H-5+H-6a+H-6b), 2.10 (s, 3H, Ac), 1.91 (s, 3H, Ac), 0.93 (s, 9H, t-butyl), 0.11 (s, 3H, MeSi), 0.10 (s, 3H, MeSi). $^{13}$C NMR (101 MHz, $CDCl_3$): $\delta_C$ 171.32 (Ac), 169.93 (Ac), 136.69, 128.62, 128.27, 128.18, 96.37 (d, $J_{C-F}$=1.2 Hz, C-1), 86.3 (d, $J_{C-F}$=185.0 Hz, C-4), 71.70 (d, $J_{C-F}$=18.9 Hz, C-3), 70.23 (d, $J_{C-F}$=23.3 Hz, C-5), 69.79 ($PhCH_2$), 61.40 (C-6), 51.83 (d, $J_{C-F}$=7.1 Hz, C-1), 25.91 ($C(CH_3)_3$), 23.11 (Ac), 20.85 (Ac), 18.42 ($C(CH_3)_3$), −5.31 (SiMe), −5.41 (SiMe). HRMS (ESI, positive) m/z calc'd for $C_{23}H_{37}FNO_6Si$ ($M+H^+$): 470.2369; found: 470.2378.

Benzyl 2-acetamido-3-O-acetyl-2,4-dideoxy-4-fluoro-α-D-glucopyranoside (50)

Compound 49 (110 mg, 234 μmol) was dissolved in a mixture of $CH_2Cl_2$ (2.0 mL) and MeOH (1.0 mL); a solution of HCl (1.0 N) was added to adjust pH to 1. After stirring for 2 h, the reaction mixture was evaporated under reduced pressure. The obtained residue was purified by column chromatography on silica gel using 25% acetone-toluene as the eluent to afford the alcohol 50 (70 mg, 84% yield). $R_f$=0.43 (Acetone/toluene, 30:70). $^1$H NMR (400 MHz, $CDCl_3$): $\delta_H$ 7.42-7.28 (m, 5H, Ph), 5.83 (d, J=9.4 Hz, 1H, NH), 5.36 (ddd, J=10.9, 9.0 Hz, $J_{H-F}$=14.3 Hz, 1H, H-3), 4.90 (dd, J=3.4, 3.4 Hz, 1H, H-1), 4.73 (d, J=11.9 Hz, 1H, Bn), 4.59 (ddd, J=9.4, 9.4 Hz, $J_{H-F}$=50.5 Hz, 1H, H-4), 4.51 (d, J=11.8 Hz, Bn), 4.25 (m, 1H, H-2), 3.92-3.73 (m, H-5+H-6a+H-6b), 2.35 (dd, J=7.4, 5.7 Hz, 1H, OH-6), 2.08 (s, 3H, Ac), 1.89 (s, 3H, Ac). $^{13}$C NMR (101 MHz, $CDCl_3$): $\delta_C$ 171.36 (Ac), 170.14 (Ac), 136.47, 128.63, 128.34, 128.15, 128.14, 128.13, 128.11, 128.11, 128.10, 96.41 (d, $J_{H-F}$=1.5 Hz, C-1), 86.21 (d, $J_{C-F}$=185.0 Hz, C-1), 71.27 (d, $J_{C-F}$=18.9 Hz, C-3), 70.08 ($PhCH_2$), 69.78 (d, $J_{C-F}$=24.4 Hz, C-1), 60.74 (C-6), 51.81 (d, $J_{H-F}$=7.2 Hz, C-2), 23.01 (Ac), 20.78 (Ac). HRMS (ESI, positive) m/z calc'd for $C_{17}H_{22}FNO_6$($M+H^+$): 356.1504; found: 356.1510.

Benzyl 2-acetamido-3-O-acetyl-2,4,6-trideoxy-4,6-difluoro-α-D-glucopyranoside (51)

To a solution of compound 50 (80 mg, 225 μmol) in $CH_2Cl_2$ (2.0 mL) at 0° C., was added DAST (59 μL, 450 μmol), and the reaction was allowed to warm up to ambient temperature and stirred overnight. MeOH (50 μL) was added to quench the reaction. The mixture was evaporated under reduced pressure and the residue was purified by column chromatography on silica gel using 10% acetone-toluene as the eluent to afford 51 (42.8 mg, 53% yield). $R_f$=0.31 (Acetone/toluene, 20:80). $[\alpha]^{25}_D$+122° (c 0.2, $CHCl_3$). $^1$H NMR (400 MHz, $CDCl_3$): $\delta_H$ 7.46-7.31 (m, 5H, Ph), 5.72 (d, J=9.3 Hz, 1H, NH), 5.39 (ddd, J=10.8, 9.1 Hz, $J_{H-F}$=14.3 Hz, 1H, H-3), 4.95 (dd, J=3.3, 3.3 Hz, 1H, H-1), 4.74 (d, J=11.9 Hz, 1H, Bn), 4.72-4.47 (m, 4H, H-4+H-6a+H-6b+Bn), 4.35-4.24 (m, 1H, H-2), 3.99 (m, 1H, H-5), 2.11 (s, 3H, Ac), 1.91 (s, 3H, Ac). $^{13}$C NMR (101 MHz, $CDCl_3$): $\delta_C$ 171.27 (Ac), 169.93 (Ac), 136.42, 128.70, 128.45, 128.26, 96.61 (d, $J_{C-F}$=1.3 Hz, C-1), 85.56 (dd, $J_{C-F}$=186.0, 7.5 Hz, C-4), 80.75 (d, $J_{C-F}$=175.0 Hz, C-6), 71.20 (d, $J_{C-F}$=18.8 Hz, C-3), 70.43 ($PhCH_2$), 68.65 ((dd, $J_{C-F}$=18.8, 23.4 Hz, C-5), 51.67 (d, $J_{C-F}$=7.1 Hz, C-2), 23.07 (Ac), 20.79 (Ac). HRMS (ESI, positive) m/z calc'd for $C_{17}H_{22}F_2NO_5$ ($M+H^+$): 358.1461; found: 358.1456.

2-Acetamido-1,3-di-O-acetyl-2,4,6-trideoxy-4,6-difluoro-α/β-D-glucopyranose (17)

The 4,6-difluroride 51 (30 mg, 84 μmol) was dissolved in a mixture of MeOH (5.0 mL), $CH_2Cl_2$ (1.0 mL) and $H_2O$ (2 drops). To this solution, was added 20% $Pd(OH)_2$ on charcoal (30 mg), and the flask was purged with hydrogen gas; the mixture was then stirred under a hydrogen atmosphere for 24 h. The reaction mixture was filtered off through a 0.22 μM membrane syringe filter, and the solution was concentrated under reduced pressure to afford the crude compound 52, which was acetylated in a mixture of pyridine (1.0 mL) and $Ac_2O$ (0.5 mL) at room temperature for 2 h. The reaction mixture was evaporated to dryness and the residue was purified by column chromatography on silica gel using 20% acetone-toluene as the eluent to afford compound 17 (24 mg, 92% yield). $R_f$=0.09 (Acetone/toluene, 20:80). $^1$H NMR (400 MHz, $CDCl_3$) for α-anomer: $\delta_H$ 6.18 (dd, J=3.3, 3.3 Hz, 1H, H-1), 5.63 (d, J=8.9 Hz, 1H, NH), 5.38 (ddd, J=8.9, 11.2 Hz, $J_{H-F}$=14.1 Hz, 1H, H-3), 4.68 (ddd, J=9.2, 10.0 Hz, $J_{H-F}$=50.5 Hz, 1H, H-4), 4.71-4.57 (m, 2H, H-6a+H-6b), 4.42 (dddd, J=3.7, 8.9, 11.4 Hz, $J_{H-F}$=1.1 Hz, 1H, H-2), 3.99 (m, 1H, H-5), 2.21 (s, 3H, Ac), 2.15 (s, 3H, Ac), 1.95 (s, 3H, Ac). $^{13}$C NMR (101 MHz, $CDCl_3$) for α-anomer: $\delta_C$ 171.67 (Ac), 170.10 (Ac), 168.63 (Ac), 90.47 (d, $J_{C-F}$=1.1 Hz, C-1), 85.03 (dd, $J_{F-C}$=7.8, 186.2 Hz, C-4), 80.22 (d, $J_{C-F}$=176.3 Hz, C-6), 70.61 (d, $J_{C-F}$=19.3 Hz, C-3), 70.32 (dd, $J_{F-C}$=18.6, 23.9 Hz, C-5), 50.81 (d, $J_{C-F}$=7.2 Hz, C-2), 22.93 (Ac), 20.82 (Ac), 20.78 (Ac). Selected $^1$H NMR (400 MHz, $CDCl_3$) for the β-anomer: $\delta_H$ 5.71 (d, J=8.7 Hz, 1H, H-1), 5.59 (d, J=8.9 Hz, 1H, NH), 5.31 (ddd, J=9.0, 10.6 Hz, $J_{H-F}$=14.3 Hz, 1H, H-3), 4.73-4.53 (m, 3H, H-4+H-6a+H-6b), 4.27 (m, 1H, H-2), 3.82 (m, 1H, H-5), 2.14 (s, 2H), 2.12 (s, 2H). Selected $^{13}$C NMR (101 MHz, $CDCl_3$) for β-anomer: $\delta_C$ 170.97 (Ac), 170.24 (Ac), 169.43 (Ac), 92.42 (d, $J_{C-F}$=1.1 Hz, C-1), 85.22 (dd, $J_{C-F}$=186.5, 7.2 Hz, C-4), 73.06 (dd, $J_{C-F}$=19.1, 24.6 Hz, C-5), 72.43 (d, $J_{C-F}$=19.3 Hz, C-3), 52.58 (d, $J_{C-F}$=7.2 Hz, C-2), 23.08 (Ac), 21.41 (Ac), 20.69 (Ac). HRMS (ESI, positive) m/z calc'd for $C_{12}H_{17}F_2NO_6Na$ ($M+Na^+$): 332.0916; found: 332.0910.

Benzyl 2-acetamido-3,4-di-O-benzyl-2-deoxy-α-D-gluco-hexodialdo-1,5-pyranoside (54)

A suspension of pyridinium chlorochromate (65 mg, 300 μmol), sodium acetate (50 mg, 600 μmol) and 4 Å molecular sieves (200 mg) in dichloromethane (20.0 mL) was stirred for 1 h. To this mixture was added drop-wise a solution of compound 53 (49.2 mg, 100 μmol) [Sharma, M., Petrie, C. R. & Korytnyk, W. General methods for modification of sialic acid at C-9. Synthesis of N-acetyl-9-deoxy-9-fluoroneuraminic acid. Carbohydrate Research 175, 25-34 (1988)] in dry dichloromethane (10.0 mL). The reaction mixture was stirred for 2 h before a 1:1 mixture of hexanes and ether (25 mL) was added. The solution was filtered through a bed of silica and the filtrate was concentrated to give the crude aldehyde. The residue was purified by column chromatography on silica gel using 60% EtOAc-hexanes as eluent to afford the desired aldehyde 54 (15.7 mg, 32%) as a colorless solid. $^1$H NMR ($CDCl_3$, 400 MHz): $\delta_H$ 9.63 (d, J=1.0 Hz, 1H, CHO), 7.40-7.26 (m, 15H, Ph), 5.35 (d, J=9.6 Hz, 1H, NH), 4.99 (d, J=3.6 Hz, 1H, H-1), 4.86-4.46 (m, 6H, $CH_2$), 4.26 (ddd, J=9.7, 9.7, 3.6 Hz, 1H, H-2), 4.19 (dd, J=~1.0, 9.6 Hz, 1H, H-5), 3.83 (dd, J=9.6, 8.4 Hz, 1H, H-3), 3.74 (dd, J=9.6, 8.4 Hz, 1H, H-4), 1.79 (s, 3H, $CH_3$). $^{13}$C NMR ($CDCl_3$, 100 MHz): $\delta_C$ 197.26 (CHO), 169.85 (CO), 138.06, 137.27, 136.82, 128.73, 128.68, 128.66, 128.43, 128.37, 128.32, 128.25, 128.12, 128.09, 97.19 (C-1), 79.56 (C-3), 78.01 (C-4), 75.52 (C-5), 75.13 ($PhCH_2$), 75.00 ($PhCH_2$), 70.46 ($PhCH_2$), 51.89 (C-2), 23.38 (Ac). HRMS (ESI, positive) m/z calc'd for for $C_{29}H_{32}NO_6[M+H]^+$: 490.2224, found 490.2242.

Benzyl 2-acetamido-3,4-di-O-benzyl-2,6-dideoxy-6,6-difluoro-α-D-glucopyranoside (55)

To a solution of compound 54 (15.7 mg, 32 μmol) in dry dichloromethane (10 mL), cooled to 0° C., was added DAST (42.3 μL, 320 μmol) by small portions, and the mixture was stirred at room temperature overnight. The reaction was then quenched with MeOH (5.0 mL), diluted with dichloromethane (100 mL), and washed with $H_2O$ (2×30 mL). The organic solution was dried over anhydrous $Na_2SO_4$ and evaporated. The residue was purified by column chromatography on silica gel using 30% EtOAc-hexanes as eluent to afford the 6,6-difluoride 55 (15.9 mg, 95% yield) as a colorless oil. $^1H$ NMR ($CDCl_3$, 400 MHz): $\delta_H$ 7.42-7.26 (m, 15H, Ph), 5.92 (td, J=54.2, 1.1 Hz, 1H, H-6), 5.29 (d, J=9.6 Hz, 1H, NH), 4.94 (d, J=4.0 Hz, 1H, H-1), 4.89-4.44 (m, 6H, $CH_2$), 4.29 (ddd, J=9.8, 9.8, 3.7 Hz, 1H, H-2), 4.00-3.86 (m, 1H, H-5), 3.82-3.70 (m, 2H, H-3, H-4), 1.80 (s, 3H, $CH_3$). $^{13}C$ NMR ($CDCl_3$, 100 MHz): $\delta_C$ 169.81 (CO), 138.18 (C), 137.47 (C), 136.75 (C), 128.75 (CH), 128.70 (CH), 128.65 (CH), 128.40 (CH), 128.29 (CH), 128.26 (CH), 128.26 (CH), 128.23 (CH), 128.06 (CH), 113.93 (t, $J_{C-F}$=243.6 Hz, C-6), 97.14 (C-1), 80.12 (C-3), 77.66 (C-4), 75.37 ($PhCH_2$), 75.20 ($PhCH_2$), 70.07 ($PhCH_2$), 69.93 (t, J=20.8 Hz, C-5), 52.29 (C-2), 23.41 (Ac). HRMS (ESI, positive) m/z calc'd for for $C_{29}H_{32}F_2NO_5[M+H]^+$: 512.2243, found 512.2239.

2-acetamido-1,3,4-tri-O-acetyl-2,6-dideoxy-6,6-difluoro-α/β-D-glucopyranose (18)

Compound 55 (15.9 mg, 31.1 μmol) was dissolved in a mixture of methanol:dichloromethane (v/v 9:1, 10 mL) and a catalytic amount of $Pd(OH)_2$ (20% on charcoal) was added. The reaction mixture was stirred under hydrogen for 48 h at room temperature. The catalyst was filtered off and the filtrate was concentrated to afford the crude compound 56 (α/β=8/1) without further purification. $^1H$ NMR ($CD_3OD$, 400 MHz) for the α-anomer: $\delta_H$ 6.04 (dt, J=1.1 Hz, $J_{H-F}$=54.1 Hz, H-6), 5.14 (d, J=3.4 Hz, 1H, H-1), 3.98 (m, 1H, H-5), 3.85 (dd, J=3.5, 10.5 Hz, 1H, H-2), 3.71 (dd, J=7.5, 10.5 Hz, 1H, H-3), 3.46 (m, 1H, H-4), 1.99 (s, 3H, Ac). $^{13}C$ NMR ($CD_3OD$, 100 MHz) for the α-anomer: $\delta_C$ 115.8 (d, $J_{C-F}$=242.1, C-6), 92.75 (C-1), 72.44 (C-3), 71.67 (dd, $J_{C-F}$=5.4, ~1 Hz, C-4), 70.08 (t, $J_{C-F}$=19.4 Hz, C-5), 55.52 (C-2), 22.59 (Ac). Selected $^1H$ NMR ($CD_3OD$, 400 MHz) for the β-anomer: $\delta_H$ 6.06 (dt, J=1.1 Hz, $J_{H-F}$=53.9 Hz, H-6), 4.65 (d, J=8.2 Hz, H-1). $^{13}C$ NMR ($CD_3OD$, 100 MHz) for the β-anomer: $\delta_C$ 97.33 (C-1), 58.58 (C-2). To a solution of crude 56 in pyridine (2 mL) was added acetic anhydride (1 mL) and the reaction mixture was stirred at room temperature overnight. The reaction was evaporated and the residue was purified by column chromatography on silica gel using to afford the desired target 18 (6.6 mg, 58% yield in two steps) as a colorless oil. $^1H$ NMR ($CDCl_3$, 400 MHz): $\delta_H$ 5.77 (dt, J=3.6 Hz, $J_{H-F}$=54.5 Hz, H-6), 5.59 (d, J=9.6 Hz, NH), 5.24-5.19 (m, 2H, H-3+H-4), 4.87(d, J=3.6 Hz, 1H, H-1), 4.31 (m, 1H, H-2), 3.92 (m, 1H, H-5), 2.04 (s, 3H, Ac), 2.03 (s, 3H, $CH_3$), 1.95 (s, 3H, $CH_3$). HRMS (ESI, positive) m/z calc'd for $C_{14}H_{20}F_2NO_8(M+H^+)$: 368.1151; found: 368.1146.

2-Hydroxyethyl 2,3,4-tri-O-acetyl-β-D-xylopyranoside (20)

Compound 57 (1.0 g, 3.14 mmol) and ethylene glycol (0.26 ml, 4.71 mmol) were dissolved in anhydrous $CH_2Cl_2$ (10.0 ml), and $BF_3 \cdot Et_2O$ (0.78 ml, 6.28 mmol) was added. After stirring at ambient temperature for 4 h. $Et_3N$ (3.0 ml) was added to quench the reaction. The mixture was evaporated to dryness under reduced pressure. The residue was purified by column chromatography on silica gel using a 40→60% gradient of EtOAc-hexanes to afford the desired compound 20 (473 mg, 47%). $^1H$ NMR (400 MHz, $CDCl_3$): $\delta_H$ 5.18 (dd, J=8.9, 8.9 Hz, 1H, H-3), 5.00-4.91 (m, 2H, H-2+H-4), 4.52 (d, J=7.1 Hz, 1H, H-1), 4.14 (dd, J=11.8, 5.2 Hz, 1H, H-5a), 3.88-3.67 (m, 4H, $OCH_aH_bCH_cH_dO$), 3.36 (td, J=11.7, 5.7 Hz, 1H, H-5b), 2.31 (t, J=6.1 Hz, 1H, OH), 2.06 (s, 3H, Ac), 2.04 (s, 3H, Ac), 2.04 (s, 3H, Ac). $^{13}C$ NMR (101 MHz, $CDCl_3$): $\delta_C$ 170.05 (Ac), 169.81 (Ac), 169.57 (Ac), 101.23 (C-1), 71.81 ($OCH_aH_b$), 71.50 (C-3), 70.99 (C-2), 68.79 (C-4), 62.24 (C-5), 61.72 ($OCH_aH_bCH_cH_dOH$), 20.69 (×3, 3×Ac). HRMS (ESI, positive) m/z calc'd for $C_{13}H_{24}NO_9$ $(M+NH_4^+)$: 338.1446; found: 338.1440.

2-(2-(2-(2-Hydroxyethoxy)ethoxy)ethoxy)ethyl 2,3,4-tri-O-acetyl-β-D-xylopyranoside (21)

Compound 57 (0.5 g, 1.57 mmol) and tetraethylene glycol (0.41 ml, 2.26 mmol) were dissolved in anhydrous $CH_2Cl_2$ (5.0 ml), and $BF_3 \cdot Et_2O$ (0.38 ml, 3.14 mmol) was added. After stirring at ambient temperature for 4 h. $Et_3N$ (1.0 ml) was added to quench the reaction. The mixture was evaporated to dryness under reduced pressure. The residue was purified by column chromatography on silica gel using a 0→5% gradient of MeOH—$CH_2Cl_2$ as the eluent to afford the desired compound 21 (404 mg, 57%). $[\alpha]^{20}_D$ −36.6° (c 0.58, $CHCl_3$). $^1H$ NMR (400 MHz, $CDCl_3$): $\delta_H$ 5.17 (dd, J=8.5, 8.5 Hz, 1H, H-3), 4.99-4.90 (m, 2H, H-2+H-4), 4.58 (d, J=6.8 Hz, 1H, H-1), 4.14 (dd, J=11.8, 5.1 Hz, 1H, H-5a), 3.91 (ddd, J=9.1, 5.2, 4.2 Hz, 1H, OCHaHb), 3.78-3.59 (m, 15H, $OCHaHbCH_cH_d(OCH_2CH_2)_3$), 3.38 (dd, J=11.8, 8.8 Hz, 1H, H-5b), 2.57 (s, 1H, OH), 2.07 (s, 2H, Ac), 2.06 (s, 2H, Ac), 2.04 (s, 2H, Ac). $^{13}C$ NMR (101 MHz, $CDCl_3$): $\delta_C$ 170.04 (Ac), 169.81 (Ac), 169.43 (Ac), 100.69 (C-1), 72.49 ($OCH_aH_b$), 71.44 (C-3), 70.78 (C-2), 70.65, 70.57, 70.56, 70.32, 70.25, 68.91 (C-4), 68.65, 61.96 (C-5), 61.65 ($CH_2OH$), 20.68 (Ac), 20.66 (×2, 2×Ac). HRMS (ESI, positive) m/z calc'd for $C_{19}H_{32}O_{12}Na$ $(M+Na^+)$: 475.1786; found: 475.1801.

2-Bromoethyl 2,3,4-tri-O-acetyl-β-D-xylopyranoside (58)

Compound 57 (1.0 g, 3.14 mmol), 2-bromoethanol (0.45 mL, 6.28 mmol) and $BF_3 \cdot Et_2O$ (0.78 mL, 6.28 mmol) were reacted in anhydrous $CH_2Cl_2$ (10.0 ml) according literature procedure [Holmqvist, K. et al. Synthesis and biology of oligoethylene glycol linked naphthoxylosides. Bioorganic & Medicinal Chemistry 21, 3310-3317 (2013).]. The desired compound 58 (634 mg,) was obtained by column chromatography on silica gel using a 20%→35% gradient of EtOAc-hexanes as an eluent.

2-Sulfoethyl 2,3,4-tri-O-acetyl-β-D-xylopyranoside, sodium salt (22)

Compound 58 (100 mg, 0.261 mmol) was dissolved in a 1:1 mixture of ethanol-water (5 ml); the solution was then heated to 70° C., and a solution of $Na_2SO_3$ (100 mg, 0.794 mmol) in water (0.7 ml) was added dropwise, and the mixture was heated to reflux for 24 h. The mixture was cooled to room temperature and evaporated under reduced pressure. The residue was acetylated using a mixture of 1:1 acetic anhydride-pyridine (2 ml) at 50° C. for 4 h, and the solution was evaporated under reduced pressure, and co-evaporated with toluene several times. The residue was purified by column chromatography on reverse phase C18 silica gel using a 0%→30% gradient of water-methanol as the eluent to afford the desired compound 22 (81 mg, 76% yield). $[\alpha]^{20}_D$ −44.5° (c 0.37, $H_2O$). $^1H$ NMR (400 MHz, $D_2O$): $\delta_H$ 5.19 (dd, J=7.9, 7.9 Hz, 1H, H-3), 4.98 (ddd, J=8.1, 8.1, 4.8 Hz, 1H, H-4), 4.88 (dd, J=6.2, 8.0 Hz, 1H, H-2), 4.80 (d, J=6.3 Hz, 1H, H-1), 4.21-4.07 (m, 2H, H-5a+OCHaHb), 3.94 (ddd, J=6.4, 6.4, 11.2 Hz, 1H, $OCH_aH_b$), 3.58 (dd, J=12.2, 8.3 Hz, 1H, H-5b), 3.17 (t, J=6.5 Hz, 2H, $CH_2SO_3^-Na^+$), 2.09 (s, 3H, Ac), 2.06 (s, 6H, 2× Ac). $^{13}C$ NMR (101 MHz, $D_2O$): $\delta_C$ 173.10 (Ac), 172.94 (Ac), 172.74 (Ac), 99.81 (C-1), 71.18 (C-3), 70.39 (C-2), 68.61 (C-4), 64.81 ($OCH_aH_b$), 61.09 (C-5), 50.61 ($CH_2SO_3^-Na^+$), 20.21 (×3, 3×Ac). HRMS (ESI, negative) m/z calc'd for $C_{13}H_{19}NaO_{11}S$ $C_{17}H_{27}O_{11}S$ ($M^-$): 383.0648; found: 383.0650.

6-Chlorohexyl 2,3,4-tri-O-acetyl-β-D-xylopyranoside (59) and 6-chlorohexyl 2,3,4-tri-O-acetyl-α-D-xylopyranoside (60)

Compound 57 (1.0 g, 3.14 mmol) and 6-chlorohexanol (0.35 ml, 6.28 mmol) were dissolved in anhydrous $CH_2Cl_2$ (10.0 ml); the mixture was then cooled to 0° C., and $BF_3{\cdot}Et_2O$ (0.78 ml, 6.28 mmol) was added. After stirring at 0° C. for 4 h. $Et_3N$ (3.0 ml) was added to quench the reaction. The mixture was diluted with EtOAc (~50 ml) and the organic solution was worked up as above. The residue was purified by column chromatography on silica gel using a 5→20% gradient of EtOAc-toluene to afford the desired compound 60 (351 mg, 28.3%) and compound 59 (588 mg, 47% yield) in pure forms. Data for 59: $[\alpha]^{20}_D$+8.7° (c 0.39, $CHCl_3$). $^1H$ NMR (400 MHz, $CDCl_3$): $\delta_H$ 5.17 (dd, J=8.6, 8.6 Hz, 1H, H-3), 4.96 (ddd, J=5.1, 8.8, 8.8 Hz, 1H, H-4), 4.92 (dd, J=6.8, 8.8 Hz, 1H, H-2), 4.48 (d, J=6.8 Hz, 1H, H-1), 4.13 (dd, J=11.8, 5.1 Hz, 1H, H-5a), 3.82 (ddd, J=9.6, 6.4, 6.4 Hz, 1H, $OCH_aH_b$), 3.54 (t, J=6.7 Hz, 2H, $CH_2Cl$), 3.48 (ddd, J=9.6, 6.4, 6.4 Hz, 1H, $OCH_aH_b$), 3.37 (dd, J=11.8, 8.9 Hz, 1H, H-5b), 2.07 (s, 3H, Ac), 2.06 (s, 3H, Ac), 2.05 (s, 3H, Ac), 1.82-1.74 (m, 2H, $OCH_aH_bCH_2$), 1.64-1.56 (m, 2H, $CH_2CH_2Cl$), 1.50-1.33 (m, 4H, $CH_2CH_2$). $^{13}C$ NMR (101 MHz, $CDCl_3$): $\delta_C$ 170.08 (Ac), 169.82 (Ac), 169.35 (Ac), 100.70 (C-1), 71.54 (C-3), 70.90 (C-2), 69.37 (C-4), 68.95 ($OCH_aH_b$), 62.05 (C-5), 44.93 ($CH_2Cl$), 32.49 ($OCH_aH_bCH_2$), 29.29 ($CH_2CH_2Cl$), 26.52 ($CH_2$), 25.21 ($CH_2$), 20.69 (×3, 3×Ac). HRMS (ESI, positive) m/z calc'd for $C_{17}H_{27}ClO_3Na$ (M+$Na^+$): 417.1287; found: 485.1280. Data for 60: $[\alpha]^{20}_D$+113.6° (c 0.28, $CHCl_3$). $^1H$ NMR (400 MHz, $CDCl_3$): $\delta_H$ 5.51-5.43 (dd, J=9.8, 9.8 Hz, 1H, H-3), 4.98 (d, J=3.5 Hz, 1H, H-1), 4.95 (ddd, J=6.0, 9.5, 10.8 Hz, 1H, H-4), 4.79 (dd, J=3.6, 10.1 Hz, 1H, H-2), 3.77 (dd, J=6.0, 10.8 Hz, 1H, H-5a), 3.69 (ddd, J=9.8, 6.5, 6.5 Hz, 1H, $OCH_aH_b$), 3.61 (dd, J=10.8, 10.8 Hz, 1H, H-5b), 3.54 (t, J=6.7 Hz, 2H, $CH_2Cl$), 3.39 (ddd, J=9.8, 6.5, 6.5 Hz, 1H, $OCH_aH_b$), 2.05 (s, 3H, Ac), 2.02 (s, 6H, 2× Ac), 1.83-1.75 (m, 2H, $OCH_aH_bCH_2$), 1.67-1.57 (m, 2H, $CH_2CH_2Cl$), 1.53-1.34 (m, 4H, $CH_2CH_2$). $^{13}C$ NMR (101 MHz, $CDCl_3$): $\delta_C$ 170.18 (Ac), 170.01 (Ac), 169.92 (Ac), 95.69 (C-1), 71.16 (C-2), 69.68 (C-3), 69.46 (C-4), 68.26 (OCHaHb), 58.27 (C-5), 44.91 ($CH_2Cl$), 32.49 ($OCH_aH_bCH_2$), 29.11 ($CH_2CH_2Cl$), 26.55 ($CH_2$), 25.37 ($CH_2$), 20.74 (Ac), 20.68 (×2, 2×Ac). HRMS (ESI, positive) m/z calc'd for $C_{17}H_{27}ClO_8Na$ (M+$Na^+$): 417.1287; found: 417.1283.

6-Sulfohexyl 2,3,4-tri-O-acetyl-β-D-xylopyranoside, sodium salt (23)

Compound 59 (70 mg, 0.13 mmol) was dissolved in a 1:1 mixture of ethanol-water (10 ml), and tetra-n-butylammonium iodide (34 mg, 0.09 mmol) was added. The solution was then heated to 70° C., and a solution of $Na_2SO_3$ (46 mg, 0.37 mmol) in water (0.5 ml) was added dropwise. After refluxing for 40 h, the mixture was cooled to room temperature and evaporated under reduced pressure. The residue was acetylated using a mixture of 1:1 acetic anhydride-pyridine (3 ml) at 50° C. for 4 h, and the solution was evaporated under reduced pressure, and co-evaporated with toluene several times. The residue was purified by column chromatography on reverse phase C18 silica gel using a 0→30% gradient of water-methanol as the eluent to afford the desired compound 23 (50 mg, 61% yield). $[\alpha]^{20}_D$ −34.5° (c 0.22, $H_2O$). $^1H$ NMR (400 MHz, $D_2O$): $\delta_H$ 5.17 (dd, J=8.4, 8.4 Hz, 1H, H-3), 4.96 (ddd, J=5.2, 8.7, 8.7 Hz, 1H, H-4), 4.81 (dd, J=7.0, 8.4 Hz, 1H, H-2), 4.70 (overlapped, 1H, H-1), 4.07 (dd, J=12.2, 5.0 Hz, 1H, H-5a), 3.79 (ddd, J=6.3, 6.3, 10.0 Hz, 1H, $OCH_aH_b$), 3.57 (ddd, J=10.2, 6.5, 6.5 Hz, 1H, $OCH_aH_b$)), 3.51 (dd, 1H, J=~12.1, 8.9, 1H, H-5b), 2.82 (high order t, J=7.7 Hz, 2H, $CH_2SO_3^-Na^+$), 2.05 (s, 3H, Ac), 2.01 (s, 3H, Ac), 2.00 (s, 3H, Ac), 1.65 (m, 2H, $OCH_aH_bCH_2$), 52 (m, 2H, $CH_2CH_2SO_3^-Na^+$), 1.41-1.22 (m, 4H, $CH_2CH_2$). $^{13}C$ NMR (101 MHz, $D_2O$): $\delta_C$ 173.03 (Ac), 172.85 (Ac), 172.61 (Ac), 99.86 (C-1), 71.44 (C-3), 70.75 (C-2), 70.19 ($OCH_aH_b$), 68.65 (C-4), 61.16 (C-5), 50.90 ($CH_2SO_3^-Na^+$), 28.24 ($OCH_aH_bCH_2$), 27.23 ($CH_2CH_2SO_3^-Na^+$), 24.56 ($CH_2$), 23.88 ($CH_2$), 20.12 (×3, 3×Ac). HRMS (ESI, positive) m/z calc'd for $C_{17}H_{27}Na_2O_{11}S$ (M+$Na^+$): 485.1064; found: 485.1077.

6-Sulfohexyl 2,3,4-tri-O-acetyl-α-D-xylopyranoside, sodium salt (24)

Compound 60 (70 mg, 0.18 mmol) was dissolved in a 1:1 mixture of ethanol-water (10 ml), and tetra-n-butylammonium iodide (33 mg, 0.09 mmol) was added. The solution was then heated to 70° C., and a solution of $Na_2SO_3$ (89 mg, 0.71 mmol) in water (0.5 ml) was added dropwise. After refluxing for 40 h, the mixture was cooled to room temperature and evaporated under reduced pressure. The residue was acetylated using a mixture of 1:1 acetic anhydride-pyridine (3 ml) at 50° C. for 4 h, and the solution was evaporated under reduced pressure, and co-evaporated with toluene several times. The residue was purified by column chromatography on reverse phase C18 silica gel using a 0%→30% gradient of water-methanol as the eluent to afford the desired compound 24 (30 mg, 34% yield). $[\alpha]^{20}_D$: +80.9° (c 43, $H_2O$). $^1H$ NMR (400 MHz, $D_2O$): $\delta_H$ 5.37 (dd, J=9.3, 9.3 Hz, 1H, H-3), 5.11 (d, J=3.6 Hz, 1H, H-1), 5.04 (ddd, J=5.6, 9.2, 10.2 Hz, 1H, H-4), 4.99 (dd, J=3.7, 9.8 Hz, 1H, H-2), 3.88 (dd, J=11.4, 5.7 Hz, 1H, H-5a), 3.75 (ddd, J=6.7, 6.7, 10.2 Hz, 1H, $OCH_aH_b$), 3.72 (dd, 1H, J=~11.2, 11.2 Hz, 1H, H-5b), 3.56 (ddd, J=10.2, 6.3, 6.3 Hz, 1H, $OCH_aH_b$)), 2.92-2.86 (high order t, J=7.9 Hz, 2H, $CH_2SO_3^-Na^+$), 2.10 (s, 3H, Ac), 2.07 (s, 3H, Ac), 2.06 (s, 3H, Ac), 1.73 (m, 2H, $OCH_aH_bCH_2$), 1.69-1.58 (m, 2H, $CH_2CH_2SO_3^-Na^+$), 1.50-1.34 (m, 4H, $CH_2CH_2$). $^{13}C$ NMR (101 MHz, $D_2O$): $\delta_C$ 173.24 (Ac), 172.98 (Ac), 172.80 (Ac), 95.30 (C-1), 70.53

(C-3), 70.34 (C-2), 69.06 (C-4), 68.49 ($OCH_aH_b$), 58.23 (C-5), 51.04 ($CH_2SO_3^-Na^+$), 28.11 ($OCH_aH_bCH_2$), 27.48 ($CH_2CH_2SO_3^-Na^+$), 24.92 ($CH_2$), 24.02 ($CH_2$), 20.21 (×2, 2×Ac), 20.13 (Ac). HRMS (ESI, positive) m/z calc'd for $C_{17}H_{27}Na_2O_{11}S$ ($M+Na^+$): 485.1064; found: 485.1071.

2-N,N-Dimethylaminoethyl 2,3,4-tri-O-acetyl-β-D-xylopyranoside (25)

Compound 58 (100 mg, 0.261 mmol) was dissolved in methanol (5 ml); a solution of dimethylamine in methanol (2.0 M, 1.0 mL) was added, and the solution was stirred at room temperature for 48 h. The mixture was concentrated under reduced pressure. The residue was acetylated using a mixture of 1:1 acetic anhydride-pyridine (2 ml) at 50° C. for 4 h, and the solution was evaporated under reduced pressure, and co-evaporated with toluene several times. The residue was dissolved in AcOEt (~20 mL), the organic solution was washed with 10% $NaHCO_3$ (20 mL), 10% brine, dried over anhydrous $Na_2SO_4$, and evaporated under reduced pressure. The residue was purified by column chromatography on reverse phase C18 silica gel using a 0→30% gradient of water-methanol as the eluent to afford the desired compound 25 (74 mg, 82% yield). $[\alpha]^{20}_D$ −40° (c 0.29, $CHCl_3$). $^1H$ NMR (400 MHz, $CDCl_3$): $\delta_H$ 5.18 (dd, J=9.1, 9.1 Hz, 1H, H-3), 4.99-4.87 (m, 2H, H-2+H-4), 4.52 (d, J=7.3 Hz, 1H, H-1), 4.25 (ddd, J=3.5, 5.2, 12.0 Hz, 1H, OCHaHb), 4.17 (ddd, J=3.7, 6.1, 12.0 Hz, 1H, OCHaHb), 4.11 (dd, J=11.8, 5.4 Hz, 1H, H-5a), 3.36 (dd, J=11.8, 9.7 Hz, 1H, H-5b), 3.33-3.27 (m, 2H, $Me_2NCHcHd$), 2.83 (s, 6H, $Me_2N$), 2.06 (s, 3H, Ac), 2.04 (s, 3H, Ac), 2.02 (s, 3H, Ac). $^{13}C$ NMR (101 MHz, $CDCl_3$): $\delta_C$ 169.86 (×2, Ac), 169.58 (Ac), 100.65 (C-1), 71.47 (C-3), 70.85 (C-2), 68.72 (C-4), 63.85 (OCHaHb), 62.53 (C-5), 57.06 ($Me_2NCHcHd$), 43.77 ($Me_2N$), 20.78 (Ac), 20.67 (Ac), 20.63 (Ac). HRMS (ESI, positive) m/z calc'd for $C_{15}H_{25}NO_3$ ($M+H^+$): 348.1653; found: 348.1667.

4-Deoxy-4-fluoro-D-xylopyranose (26)

To a solution of 1,2,3-tri-O-benzoyl-4-deoxy-4-fluoro-α-D-xylopyranose 61 (227 mg, 0.49 mmol) [Tsuzuki, Y., Nguyen, T. K. N., Garud, D. R., Kuberan, B. & Koketsu, M. 4-Deoxy-4-fluoro-xyloside derivatives as inhibitors of glycosaminoglycan biosynthesis. Bioorganic & Medicinal Chemistry Letters 20, 7269-7273 (2010)] in dry methanol (10 mL) was added 2 drops of a freshly prepared 0.1 M sodium methoxide solution. The mixture was stirred and monitored by TLC at room temperature for 0.5 h. The reaction was quenched by adding Amberlite IR120 ($H^+$) resin. Once the pH reached 6-7, the mixture was filtered and the filtrate was concentrated to dryness. The crude product was purified by HPLC chromatography (C18) using a gradient of MeOH-water (5:95→10:90) to afford compound 26 (34 mg, 48%). $R_f$=0.57 ($CH_2Cl_2$/MeOH, 8:2). $^1H$ NMR ($D_2O$, 400 MHz) for α-anomer: $\delta_H$ 5.23 (dd, J=3.6 Hz, $J_{H-F}$=3.6 Hz, 1H, H-1), 4.66-4.43 (dm, $J_{H-F}$=50.3 Hz, 1H, H-4), 3.99 (ddd, J=9.2, 7.4 Hz, $J_{H-F}$=15.1 Hz, 1H, H-3), 3.93 (m, 2H, H-5), 3.61 (ddd, J=3.6, 9.2 Hz, $J_{H-F}$=1 Hz, 1H, H-2). $^{13}C$ NMR ($D_2O$, 100 MHz) for α-anomer: $\delta_C$ 91.9 (d, $J_{C-F}$=1.4 Hz, C-1), 89.1 (d, $J_{C-F}$=177.9 Hz, C-4), 71.1 (d, $J_{C-F}$=18.2 Hz, C-3), 70.8 (d, $J_{2-F}$=7.7 Hz, C-2), 58.6 (d, $J_{5-F}$=27.8 Hz, C-5). $^1H$ NMR ($D_2O$, 400 MHz) for β-anomer: $\delta_H$ 4.67 (d, J=7.8 Hz, 1H, H-1), 4.66-4.43 (dm, $J_{H-F}$=50.3 Hz, 1H, H-4), 4.16 (ddd, J=5.6, 11.6 Hz, $J_{H-F}$=1.3 Hz, 1H, H-5a), 3.79 (ddd, J=9.3, 9.3 Hz, $J_{H-F}$=15.7 Hz, 1H, H-3), 3.56 (ddd, J=3.9, 11.6 Hz, $J_{H-F}$=10.2 Hz, 1H, H-5b), 3.33 (ddd, J=7.8, 9.3 Hz, $J_{H-F}$=1 Hz, 1H, H-2). $^{13}C$ NMR ($D_2O$, 100 MHz) for β-anomer: $\delta_C$ 96.5 (d, $J_{C-F}$=1.2 Hz, C-1), 89.2 (d, $J_{C-F}$=177.9 Hz, C-4), 74.0 (d, $J_{C-F}$=18 Hz, C-3), 73.3 (d, $J_{C-F}$=9.1 Hz, C-2), 62.3 (d, $J_{C-F}$=28.7 Hz, C-5). HRMS (ESI, positive) m/z calc'd for for $C_5H_9O_4FNa$ $[M+Na]^+$: 175.0377, found 175.0370.

1,2,3-Tri-O-acetyl-4-deoxy-4-fluoro-α-D-xylopyranose (27) and 1,2,3-tri-O-acetyl-4-deoxy-4-fluoro-β-D-xylopyranose (28)

To a solution of 26 (21 mg, 0.14 mmol) in dry pyridine (5 mL) was added acetic anhydride (0.18 mL, 1.38 mmol, 10 eq) at 0° C. under inert atmosphere. The mixture was stirred for 6 h at room temperature, cooled to 0° C. and quenched with methanol. The mixture was concentrated to dryness and the residue was dissolved in EtOAc. The organic layer was successfully washed with an aqueous solution of 1 M HCl, saturated aqueous $NaHCO_3$ and brine before been dried over $Na_2SO_4$, filtered, and concentrated to dryness. The crude product was purified by chromatography (hexane/EtOAc, 9:1) to afford compound 27 (18.5 mg, 49%) and 28 (18.7 mg, 49%). Data for 27: $R_f$=0.41 (EtOAc/hexanes, 3:7). $[\alpha]^{20}_D$+46° (c 0.5, $CHCl_3$). $^1H$ NMR ($CDCl_3$, 400 MHz): $\delta_H$ 6.22 (dd, J=3.6 Hz, $J_{H-F}$=3.5 Hz, 1H, H-1), 5.52 (ddd, J=10.1, 8.9 Hz, $J_{H-F}$=13.3 Hz, 1H, H-3), 4.97 (ddd, J=3.6, 10.1 Hz, $J_{H-F}$=0.9 Hz, 1H, H-2), 4.61 (dddd, J=8.9, 6, 10.9 Hz, $J_{H-F}$=49.9 Hz, 1H, H-4), 4.01 (dd, J=6.0, 11.3 Hz, 1H, H-5a), 3.85 (ddd, J=10.9, 11.3 Hz, $J_{H-F}$=4.8 Hz, 1H, H-5b), 2.18 (s, 3H, Ac), 2.10 (s, 3H, Ac), 2.02 (s, 3H, Ac). $^{13}C$ NMR ($CDCl_3$, 100 MHz): $\delta_C$ 170.0 (Ac), 169.9 (Ac), 169.0 (Ac), 89.1 (d, $J_{C-F}$=1 Hz, C-1), 86.5 (d, $J_{C-F}$=185.8 Hz, C-4), 70.2 (d, $J_{C-F}$=20 Hz, C-3), 69.1 (d, $J_{C-F}$=8.1 Hz, C-2), 61.0 (d, $J_{C-F}$=27.7 Hz, C-5), 21.0 (Ac), 20.9 (Ac), 20.6 (Ac). HRMS (ESI, positive) m/z calc'd for $C_{11}H_{15}O_7FNa$ $[M+Na]^+$: 301.0694, found, 301.0698. Data for 28: $R_f$=0.38 (EtOAc/hexanes, 3:7). $[\alpha]^{20}_D$ −56° (c 0.86, $CHCl_3$). $^1H$ NMR ($CDCl_3$, 400 MHz): $\delta_H$ 5.76 (d, J=6.3 Hz, 1H, H-1), 5.25 (ddd, J=7.8, 7.4 Hz, $J_{H-F}$=13.4 Hz, 1H, H-3), 4.97 (ddd, J=6.3, 7.8 Hz, $J_{H-F}$=0.5 Hz, 1H, H-2), 4.6 (dddd, J=7.4, 4.6, 7.8 Hz, $J_{H-F}$=48.5 Hz, H-4), 4.18 (ddd, J=4.6, 12.4 Hz, $J_{H-F}$=12.9 Hz, 1H, H-5a), 3.73 (ddd, J=7.8, 12.4 Hz, $J_{H-F}$=7.8 Hz, 1H, H-5b), 2.1 (s, 3H, Ac), 2.09 (s, 3H, Ac), 2.06 (s, 3H, Ac). $^{13}C$ NMR ($CDCl_3$, 100 MHz): $\delta_C$ 169.5 (Ac), 169.4 (Ac), 168.9 (Ac), 91.8 (C-1), 85.7 (d, $J_{C-F}$=185 Hz, C-4), 70.8 (d, $J_{C-F}$=23.3 Hz, C-3), 68.9 (d, $J_{C-F}$=6.1 Hz, C-2), 62.6 (d, $J_{C-F}$=26.2 Hz, C-5), 20.7 (Ac), 20.6 (Ac), 20.5 (Ac). HRMS (ESI, positive) m/z calc'd for $C_{11}H_{15}O_7FNa$ $[M+Na]^+$: 301.0694, found, 301.0698.

TABLE 1

Compounds used in the study

| Compound short-form | # | Reduce CSPG production | Enhance OPC outgrowth | Reduce T cell proliferation |
|---|---|---|---|---|
| Ac-4,4-diF-GlcNAc (16) | 16 | **** | *** | **** |
| Ac-4-F-GlcNAcOH (10) | 10 | *** | ** | **** |
| Ac-4-F-GalNAc (13) | 13 | ** | * | **** |
| Ac-4-F-GalNAcOPr (7) | 7 | ** | * | **** |
| Ac-bXyl-TEG (21) | 21 | ** | n.s. | n.s. |
| Ac-4-FGlcNAc (3) | 3 | *** | ** | **** |
| Ac-4-F-GalNAcOBu (8) | 8 | * | * | **** |
| Ac-6,6-diF-GlcNAc (18) | 18 | n.s. | * | n.s. |
| Ac-bXyl-C6S (23) | 23 | n.s. | * | * |
| Pr-4-F-GlcNAcOH (11) | 1 | n.s. | n.s. | **** |

TABLE 1-continued

Compounds used in the study

| Compound short-form | # | Reduce CSPG production | Enhance OPC outgrowth | Reduce T cell prolif-eration |
|---|---|---|---|---|
| Ac-GlcNAc (1) | 11 | n.s. | n.s. | **** |
| Bu-4-F-GlcNAcOH (12) | 12 | n.s. | n.s. | ** |
| Ac-4-F-GlcNTFA (9) | 9 | n.s. | — | *** |
| Ac-4-Cl-GlcNAcOH (14) | 14 | n.s. | — | ** |
| Ac-4-Cl-GlcNAc (15) | 15 | n.s. | — | * |
| Ac-4-Me-GlcNAc (2) | 2 | n.s. | n.s. | * |
| Ac-4-F-aXyl (28) | 28 | n.s. | n.s. | n.s. |
| Ac-4-F-bXyl (27) | 27 | n.s. | n.s. | n.s. |
| 4-F-Xyl (26) | 26 | n.s. | n.s. | n.s. |
| Ac-bXyl-MEG (20) | 20 | n.s. | — | n.s. |
| Ac-4,6-diF-GlcNAc (17) | 17 | n.s. | — | n.s. |
| Me-4-F-GlcNAc (5) | 5 | n.s. | — | n.s. |
| Ac-aXyl-C6S (24) | 24 | n.s. | — | n.s. |
| MeAc-4-F-GlcNAc (6) | 6 | n.s. | — | n.s. |
| bXyl-OBn (19) | 19 | n.s. | — | n.s. |
| Ac-bXyl-C2S (22) | 22 | n.s. | — | n.s. |

****$p < 0.0001$,
***$p < 0.001$,
**$p < 0.01$,
*$p < 0.05$,
'n.s.' = non-significant,
'—' = not tested In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention claimed is:

1. A compound of formula (65) or a pharmaceutically acceptable salt thereof:

65

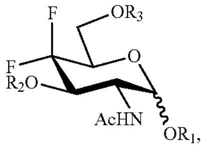

wherein $R_1$, $R_2$ and $R_3$ are independently H or an acyl group and at least one of $R_1$, $R_2$ and $R_3$ is an acyl group defined as R'CO— or R"XCO", wherein:

R' is a substituted or unsubstituted, branched or linear alkyl or heteroalkyl containing up to 20 carbons;

R" is a substituted or unsubstituted, branched or linear alkyl or heteroalkyl containing up to 20 carbons; and X is a heteroatom selected from the group consisting of O, N, and S; and $R_1$, $R_2$, and $R_3$ are not an acetyl group at the same time.

2. The compound of claim 1, wherein both $R_1$ and $R_2$ are an acetyl group.

3. The compound of claim 1, wherein both $R_1$ and $R_3$ are an acetyl group.

4. The compound of claim 1, wherein both $R_2$ and $R_3$ are an acetyl group.

5. The compound of claim 1, wherein the heteroatoms of R' are O.

6. The compound of claim 1, wherein the substituents of R' are halogen.

7. The compound of claim 1, wherein X is O.

8. The compound of claim 1, wherein X is N.

9. The compound of claim 1, wherein X is S.

10. A pharmaceutical composition comprising a compound of claim 1 and a pharmaceutically acceptable excipient.

11. A method for treating multiple sclerosis, a neurological disease or disorder associated with up-regulation of an extracellular matrix or chondroitin sulfate proteoglycans, an autoimmune disorder associated with up-regulation of an extracellular matrix or chondroitin sulfate proteoglycans, or a tumour associated with up-regulation of an extracellular matrix or chondroitin sulfate proteoglycans, said method comprising administering to a subject in need thereof a therapeutically effective amount of the compound of claim 1.

12. The method of claim 11, wherein both $R_1$ and $R_2$ are an acetyl group.

13. The method of claim 11, wherein both $R_1$ and $R_3$ are an acetyl group.

14. The method of claim 11, wherein both $R_2$ and $R_3$ are an acetyl group.

15. The method of claim 11, wherein the heteroatoms of R' are O.

16. The method of claim 11, wherein the substituents of R' are halogen.

17. The method of claim 11, wherein X is O.

18. The method of claim 11, wherein X is N.

19. The method of claim 11, wherein X is S.

* * * * *